(12) United States Patent
Klein et al.

(10) Patent No.: US 9,656,949 B2
(45) Date of Patent: May 23, 2017

(54) SUBSTITUTED CARBOXYLIC ACID DERIVATIVES AS AGGRECANASE INHIBITORS FOR THE TREATMENT OF OSTEOARTHRITIS

(71) Applicant: MERCK PATENT GMBH, Darmstadt (DE)

(72) Inventors: Markus Klein, Darmstadt (DE); Sven Lindemann, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/765,913

(22) PCT Filed: Jan. 16, 2014

(86) PCT No.: PCT/EP2014/000100
§ 371 (c)(1),
(2) Date: Aug. 5, 2015

(87) PCT Pub. No.: WO2014/121884
PCT Pub. Date: Aug. 14, 2014

(65) Prior Publication Data
US 2015/0368188 A1    Dec. 24, 2015

(30) Foreign Application Priority Data

Feb. 6, 2013   (EP) ..................... 13000592

(51) Int. Cl.
| | | |
|---|---|---|
| *A61K 31/519* | (2006.01) | |
| *A61K 31/337* | (2006.01) | |
| *A61K 31/415* | (2006.01) | |
| *A61K 31/426* | (2006.01) | |
| *A61K 31/4406* | (2006.01) | |
| *A61K 31/451* | (2006.01) | |
| *A61K 31/495* | (2006.01) | |
| *A61K 31/4965* | (2006.01) | |
| *C07C 237/22* | (2006.01) | |
| *C07D 213/81* | (2006.01) | |
| *C07D 213/82* | (2006.01) | |
| *C07D 233/64* | (2006.01) | |
| *C07D 241/12* | (2006.01) | |
| *C07D 241/24* | (2006.01) | |
| *C07C 233/83* | (2006.01) | |
| *C07D 277/30* | (2006.01) | |
| *C07D 277/56* | (2006.01) | |

(Continued)

(52) U.S. Cl.
CPC .......... *C07C 237/22* (2013.01); *A61K 31/197* (2013.01); *A61K 31/337* (2013.01); *A61K 31/415* (2013.01); *A61K 31/426* (2013.01); *A61K 31/4406* (2013.01); *A61K 31/451* (2013.01); *A61K 31/495* (2013.01); *A61K 31/4965* (2013.01); *C07C 233/83* (2013.01); *C07D 211/34* (2013.01); *C07D 211/66* (2013.01); *C07D 213/40* (2013.01); *C07D 213/56* (2013.01); *C07D 213/81* (2013.01); *C07D 213/82* (2013.01); *C07D 231/12* (2013.01); *C07D 233/64* (2013.01); *C07D 241/12* (2013.01); *C07D 241/24* (2013.01); *C07D 277/30* (2013.01); *C07D 277/56* (2013.01); *C07D 295/215* (2013.01); *C07D 305/08* (2013.01)

(58) Field of Classification Search
CPC ... C07C 233/83; C07C 237/22; C07D 211/34; C07D 211/66; C07D 213/40; C07D 213/56; C07D 213/81–213/82; C07D 231/12; C07D 233/64; C07D 241/12; C07D 241/24; C07D 277/30; C07D 277/56; C07D 295/18; C07D 295/215; C07D 305/08; A61K 31/197; A61K 31/337; A61K 31/415; A61K 31/426; A61K 31/4406; A61K 31/451; A61K 31/495; A61K 31/4965
See application file for complete search history.

(56) References Cited

U.S. PATENT DOCUMENTS

2007/0043066 A1 *   2/2007  Sum ..................... C07D 409/04
                                                      514/275

OTHER PUBLICATIONS

West, Anthony R., Solid State Chemistry and Its Applications, Wiley, New York, 1988, 358.*

(Continued)

*Primary Examiner* — Erich A Leeser
(74) *Attorney, Agent, or Firm* — Millen, White, Zelano and Branigan, P.C.

(57) ABSTRACT

The present invention relates to compounds of the formula I and in particular medicaments comprising at least one compound of the formula I for use in the treatment and/or prophylaxis of physiological and/or pathophysiological states in the triggering of which ADAMTS5 is involved, in particular for use in the treatment and/or prophylaxis of osteoarthritis, hepatocirrhosis, traumatic cartilage injuries, pain, allodynia or hyperalgesia.

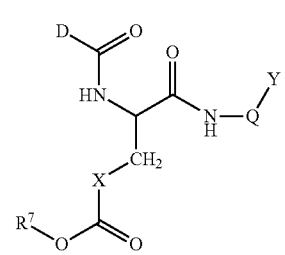

11 Claims, No Drawings

(51) Int. Cl.
  *C07D 211/34*   (2006.01)
  *C07D 213/40*   (2006.01)
  *C07D 213/56*   (2006.01)
  *C07D 305/08*   (2006.01)
  *A61K 31/197*   (2006.01)
  *C07D 211/66*   (2006.01)
  *C07D 231/12*   (2006.01)
  *C07D 295/215*  (2006.01)

(56) References Cited

OTHER PUBLICATIONS

International Search Report dated May 28, 2014 issued in corresponding PCT/EP2014/000100 application (pp. 1-2).

* cited by examiner

SUBSTITUTED CARBOXYLIC ACID DERIVATIVES AS AGGRECANASE INHIBITORS FOR THE TREATMENT OF OSTEOARTHRITIS

The present invention relates to compounds of the formula I and in particular medicaments comprising at least one compound of the formula I for use in the treatment and/or prophylaxis of physiological and/or pathophysiological states in the triggering of which ADAMTS5 is involved, in particular for use in the treatment and/or prophylaxis of osteoarthritis, traumatic cartilage injuries, pain, allodynia or hyperalgesia.

BACKGROUND OF THE INVENTION

Osteoarthritis (OA) is one of the most disabling diseases in developed countries. The prevalence of OA is estimated to one in ten men and one in five women aged over 60 years worldwide. As such, the disease accounts for considerable health care expenditure and therefore represents a significant socio-economic burden. To date, no disease modifying treatment is available. Current treatment is therefore entirely symptomatic up to the point when total joint replacement may be indicated.

In spite of this significant importance for the health system, the causes of OA remain unclear to date and effective preventative measures furthermore remain a distant aim. A reduction in the joint gap (caused by destruction of the joint cartilage), together with changes in the subchondral bone and osteophyte formation, are the radiological characteristics of the disease. For the patient, however, pain (load-dependent and nocturnal rest pain) with subsequent function impairments are to the fore. It is also these which force the patient into social isolation with corresponding secondary diseases.

The term osteoarthritis according to an unofficial definition denotes "joint wear" which exceeds the usual extent for the age. The causes are regarded as being excessive load (for example increased body weight), connatal or traumatic causes, such as malposition of the joint, or also bone deformations due to bone diseases, such as osteoporosis. Osteoarthritis can likewise arise as a consequence of another disease, for example joint inflammation (arthritis) (secondary osteoarthritis), or accompany overload-induced effusion (secondary inflammation reaction) (activated osteoarthritis). The Anglo-American specialist literature differentiates between osteoarthritis (OA), in which the destruction of the joint surfaces can probably be attributed principally to the effects of load, and arthritis (rheumatoid arthritis, RA), in which joint degeneration due to an inflammatory component is to the fore.

In principle, osteoarthritis is also differentiated according to its cause. Arthrosis alcaptonurica is based on increased deposition of homogentisic acid in joints in the case of previously existing alcaptonuria. In the case of haemophilic arthrosis, regular intra-articular bleeding occurs in the case of haemophilia (haemophilic joint). Arthrosis urica is caused by the mechanical influence of urate crystals (uric acid) on the healthy cartilage (Pschyrembel W. et al.: Klinisches Wörterbuch, Verlag Walter de Gruyter & Co, 253rd Edition, 1977).

The classical cause of osteoarthritis is dysplasia of joints. Using the example of the hip, it becomes clear that the zone with the greatest mechanical stress in the case of a physiological hip position represents a significantly larger area than in the case of a dysplastic hip. However, the stresses caused by the forces acting on the joint are substantially independent of the joint shape. They are essentially distributed over the main stress zone(s). A greater pressure will thus arise in the case of a relatively small zone than in the case of a larger one. The biomechanical pressure on the joint cartilage is thus greater in the case of a dysplastic hip than in the case of a physiological hip position. This rule is generally regarded as the cause of the increased occurrence of arthritic changes in supporting joints which differ from the ideal anatomical shape.

If the consequences of an injury are responsible for premature wear, the term post-traumatic arthrosis is used. Further causes of secondary arthrosis or osteoarthritis that are being discussed are mechanical, inflammatory, metabolic, chemical (quinolones), trophic, hormonal, neurological and genetic reasons. In most cases, however, the diagnosis given is idiopathic arthrosis, by which the doctor means an apparent absence of a causal disease (H. I. Roach and S. Tilley, Bone and Osteoarthritis, F. Bronner and M. C. Farach-Carson (Editors), Verlag Springer, Volume 4, 2007).

Medicinal causes of osteoarthritis can be, for example, antibiotics of the gyrase inhibitor type (fluoroquinolones, such as ciprofloxacin, levofloxacin). These medicaments result in complexing of magnesium ions in poorly vascularised tissues (hyaline joint cartilage, tendon tissue), which has the consequence that irreversible damage occurs to connective tissue. This damage is generally more pronounced in the growth phase in children and juveniles. Tendinopathies and arthropathies are known side effects of this class of medicaments. In adults, these antibiotics result in accelerated physiological degradation of the hyaline joint cartilage according to information from independent pharmacologists and rheumatologists (Menschik M. et al., Antimicrob. Agents Chemother. 41, pp. 2562-2565, 1997; Egerbacher M. et al., Arch. Toxicol. 73, pp. 557-563, 2000; Chang H. et al., Scand. J. Infect. Dis. 28, pp. 641-643, 1996; Chaslerie A. et al., Therapie 47, p. 80, 1992). Extended treatment with phenprocoumone can also favour arthrosis by decreasing bone density in the case of stresses of the joint internal structure.

Besides age, known risk factors for osteoarthrosis are mechanical overload, (micro)traumas, joint destabilisation caused by loss of the securing mechanisms, and genetic factors. However, neither the occurrence nor possible interventions have been fully explained (H. I. Roach and S. Tilley, Bone and Osteoarthritis, F. Bronner and M. C. Farach-Carson (Editors), Verlag Springer, Volume 4, 2007).

In a joint affected by osteoarthritis, the content of nitrogen monoxide is increased in some cases. A similar situation has been observed due to high mechanical irritation of cartilage tissue (Das P. et al., Journal of Orthopaedic Research 15, pp. 87-93, 1997; Farrell A. J. et al., Annals of the Rheumatic Diseases 51, pp. 1219-1222, 1992; Fermor B. et al., Journal of Orthopaedic Research 19, pp. 729-737, 2001), whereas moderate mechanical stimulation tends to have a positive effect. The action of mechanical forces is thus causally involved in the progress of osteoarthritis (Liu X. et al., Biorheology 43, pp. 183-190, 2006).

In principle, osteoarthritis therapy follows two aims: firstly freedom from pain under normal load and secondly the prevention of mechanical restrictions or changes in a joint. These aims cannot be achieved in the long term by pain treatment as a purely symptomatic therapy approach, since this cannot halt the progress of the disease. If the latter is to be achieved, the cartilage destruction must be stopped. Since the joint cartilage in adult patients cannot regenerate, the elimination of pathogenetic factors, such as joint dysplasia or malpositions, which result in increased point pressure on the joint cartilage, is in addition enormously important.

Finally, it is attempted to prevent or stop the degeneration processes in the cartilage tissue with the aid of medicaments.

An essential factor for the functioning state and thus the resistance of the joint cartilage to stress is the extracellular matrix, which primarily consists of collagens, proteoglycans and water. The enzymes involved in degradation of the extracellular matrix include, in particular the metalloproteases, aggrecanases and cathepsin enzymes.

Aggrecan is a main proteoglycan in cartilage, and decomposition of its core protein by protease is one of the early signs of a joint disorder associated with arthrodial cartilage destruction, such as rheumatoid arthritis and osteoarthritis. This process of decomposition leading to the cartilage destruction begins with the disappearance of aggrecan on the surface of cartilage, and progresses to the decomposition of collagen type II fiber (Sandy J. D. et al., J. Clin. Invest. 89, 1512-1516, 1992; Lohmander L. S. et al., Arthritis Rheum. 36, 1214-1222, 1993).

MMPs (matrix metalloproteinases) that cleave Asn 341-Phe 342 and aggrecanase that cleaves Glu 373-Ala 374 are known as enzymes involved in this decomposition of aggrecan, and both are metal-pro/eases having zinc in the catalytic active center. The latter was determined to be ADAMTS (A Disintegrin and Metalloproteinase with Thrombospondin Motifs) in 1999. ADAMTS 1 to 20 have been identified so far, and ADAMTS 4 and 5 to aggrecanase-1 and aggrecanase-2, respectively (Abbaszade I. et al, J. Biol. Chem. 274 (33): 23443-23450, 1999, Hurskainen T. L. et al., J. Biol. Chem. 274 (36): 25555-25563, 1999). Conventionally, MMPs have been considered to mainly cause cartilage destruction, but many reports have documented that the aggrecan fragments found in the joint of osteoarthritis (OA) patients are predominantly the fragments cleaved by aggrecanases. Thus, aggrecanase is also considered to be a significant vicious factor for these disease states.

Aggrecanases have been shown to be involved in cleaving aggrecan, procollagen processing (Colige A et al., Proc. Natl Acad. Sd. USA, 94, 2374-2379, 1997), inflammation (Kuno K. et al., J. Biol. Chem., 272, 556-562, 1997), angiogenesis (Vazquez F. et al., J. Biol. Chem. 1999, 274, 23349-23357) and tumor invasion (Masui T. et al., J. Bio. I Chem., 272, 556-562, 1997).

ADAMTS5 is a member of the ADAMTS (a disintegrin and metalloproteinase with thrombospondin motifs) protein family. Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains. The enzyme encoded by this gene contains two C-terminal TS motifs and functions as aggrecanase to cleave aggrecan, a major proteoglycan of cartilage.

Genetically modified mice in which the catalytic domain of ADAMTS5 was deleted are resistant to cartilage destruction in an experimental model of osteoarthritis (Glasson S. S. et al., Nature 434 (7033): 644-648, 2005) and ADAMTS5 is the major aggrecanase in mouse cartilage in a mouse model of inflammatory arthritis (Stanton H. et al., Nature 434 (7033): 648-652, 2005).

Additionally, aggrecanases like MMPs are suggested to be involved in metastasis or tissue infiltration of tumor cells and thus aggrecanase inhibitors are expected to be effective antitumor agents. Furthermore, the following documents disclose, that aggrecanase inhibitors are also effective in the treatment and/or prophylaxis of physiological and/or pathophysiological states, selected from the group consisting of osteoarthritis, traumatic cartilage injuries, pain, allodynia, hyperalgesia, rheumatoid arthritis, joint injury, reactive arthritis, cirrhosis, inflammatory diseases as inflammatory bowel disease, ulceratice colitis, gastritis, psoriasis, eczema and dermatitis, asthma, allergic reaction, chronic obstructive pulmonary disease, fibroid lung, acute respiratory distress (ARDS), lung infection, interstitial pneumonia, atherosclerosis, osteoporosis, age-related macular degeneration, myocardial infarction, corneal ulceration cancer, tumor metastasis and invasion, uncontrolled degradation of the extracellular matrix as in osteoarthritis, central nervous system diseases, abnormal wound healing, multiple sclerosis angiogenesis and restenosis.

The U.S. Pat. Nos. 7,030,242, 6,566,384 and the WO9805635 disclose hydroxamic and carboxylic acid derivatives as aggrecanase and MMP-13 inhibitors for the treatment of osteoarthritis. The US20080096918 discloses cyclic urea derivatives as aggrecanase inhibitors for the treatment of rheumatoid arthritis and osteoarthritis.

The WO2001062750 and the WO2000012478 disclose arylpiperazines as MMP inhibitors for the treatment of various diseases. The WO2009109230 aryl- and heteroaryl-benzopyranoneamidino derivatives for the treatment of osteoarthritis and cancer-related pain and the WO2008024922 hydroxyquinoline derivatives for the treatment of metalloproteinase related disorders.

The WO2005058884 discloses cyclopropane compounds as aggrecanase and MMP-13 inhibitors for the treatment of disorders such as rheumatoid arthritis and osteoarthritis, joint injury, reactive arthritis, bone resorption disorder, cancer, asthma, allergic reaction, chronic pulmonary emphysema, fibroid lung, acute respiratory distress (ARDS), lung infection and interstitial pneumonia.

The WO2007008994 and the WO2008058278 disclose glutamate derivatives as aggrecanase inhibitors for the treatment of arthritic disorders, osteoarthritis, cancer, rheumatoid arthritis, asthma, chronic obstructive pulmonary disease, atherosclerosis, age-related macular degeneration, myocardial infarction, corneal ulceration and other ocular surface diseases, hepatitis, aortic aneurysms, tendonitis, central nervous system diseases, abnormal wound healing, angiogenesis, restenosis, cirrhosis, multiple sclerosis, glomerulonephritis, graft versus host disease, diabetes, inflammatory bowel disease, shock, invertebral disc degeneration, stroke, osteopenia and periodontal diseases.

The invention was based on the object of finding novel compounds having valuable properties, in particular those which can be used for the preparation of medicaments.

The aim of the present invention was, in particular, to find novel active compounds and particularly preferably novel ADAMTS5 inhibitors which can be employed for the prevention and treatment of osteoarthritis and have, in particular, high selectivity for ADAMTS5. In addition, the aim was to find novel ADAMTS5 inhibitors which are sufficiently stable, at least on local or intra-articular administration.

SUMMARY OF THE INVENTION

Surprisingly, it has been found that the compounds of formula I according to the invention inhibit ADAMTS5 or both, ADAMTS4 and ADATMS5, highly effectively, which play a crucial role in the development of osteoarthritis. Furthermore, the compounds of the present invention are highly selective inhibitors of ADAMTS5 or both, ADAMTS4 and ADATMS5 without inhibiting other MMPs as MMP1 and MMP14 which can lead to undesirable side effects. In addition, the compounds according to the invention have adequately good stability in synovial fluid, meaning that they are suitable for intra-articular administration and thus for the treatment of osteoarthritis or rheumatoid arthritis.

Surprisingly, in comparison to the similar compounds of the WO2007008994 compounds of the present invention, which are substituted in the alpha position to the carboxylic acid, show a higher selectivity for ADAMTS5 or both, ADAMTS4 and ADAMTS5, whereas the compounds of the WO2007008994 are disclosed to also inhibit other MMPs (matrix metalloproteinases) leading to undesirable side effects. Additionally, the compounds of the present invention are more potent ADAMTS5 inhibitors than the compounds of the WO2007008994. Furthermore, aliphatic carboxylic acids are metabolically eliminated under formation of reactive metabolites, in the present case acylglucuronides. This formation of reactive metabolites in combination with a high dosing, e.g. described for the compound (S)-4-[(Biphenyl-4-carbonyl)-amino]-4-[2-(4-fluoro-phenyl)-1,1-dimethyl-ethylcarbamoyl]-butyric acid of the WO2007008994, leads to a higher risk of idiosyncratic toxicity (Smith G. F., Designing drugs to avoid toxicity, 2011). In contrast to the compounds of the WO2007008994, due to the substitution in the alpha position to the carboxylic acid the compounds of the present invention show a significantly reduced glucuronidation leading to less toxicity. Finally, the compounds of the present invention show a significantly increased plasma protein binding (human protein) in comparison with the compounds of the WO2007008994.

The invention relates to compounds of the formula I,

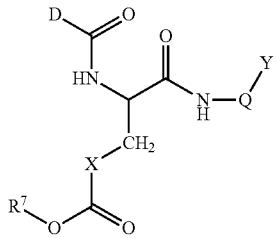

I wherein

X is $CHR^1$ or $CR^1R^2$, wherein optionally $R^1$ and $R^2$ with the C-atom they are bound to form a cycloalkyl or heterocyclyl containing 3 to 7 C-atoms wherein optionally 1 to 3 $CH_2$-groups are substituted by —O—, —S—, —SO—, —SO$_2$—, —NR—, —OCO—, —NRCONR'—, —NRCO—, —NRSO$_2$R'—, —COO—, —CONR— or —CH═CH— and wherein optionally 1 to 11 H-atoms are substituted by F or Cl, D -E-G-K or -L, E, K are independently from one another a saturated, unsaturated or aromatic hydrocarboncycle which is unsubstituted or 1 to 4 substituted by $R^1$ or $R^2$, or a monocyclic saturated, unsaturated or aromatic heterocycle with 1 to 4 heteroatoms selected from N, O and S which is unsubstituted or mono-, di- or trisubstituted by $R^1$, $R^2$, ═S, ═$NR^1$ or ═O, G is a single bond, L is -E-G-K, wherein E and K in addition to the single bond G are linked via an additional alkyl linker containing 1 to 3 C-atoms wherein optionally one $CH_2$-group is substituted by —$CR^1R^2$—, —O—, —S—, —SO—, —SO$_2$—, —$NR^1$—, —OCO—, —$NR^1CONR^2$—, —$NR^1CO$—, —$NR^1SO_2R^2$—, —COO—, —$CONR^1$— or —CH═CH—, Y is H, $R^1$ or a saturated, unsaturated or aromatic hydrocarboncycle which is unsubstituted or 1 to 4 times substituted by $R^1$ or a monocyclic saturated, unsaturated or aromatic heterocycle with 1 to 4 heteroatoms selected from N, O and S which is unsubstituted or mono-, di- or trisubstituted by $R^1$, ═S, ═$NR^1$ or ═O, Q is a single bond or a linear, branched or mono- or bicyclic alkyl linker containing 1 to 10 C-atoms wherein optionally 1 to 5 $CH_2$-groups are substituted by —$CR^3R^4$—, —S—, —SO—, —SO$_2$—, —$NR^3$—, —OCO—, —$NR^3CONR^4$—, —$NR^3CO$—, —$NR^3SO_2R^4$—, —COO— or —$CONR^3$— and wherein optionally 1 to 20 H-atoms are substituted by F or Cl, wherein $R^3$ und $R^4$ with the atoms they are bound to optionally form a cycloalkyl or heterocyclyl containing 3 to 7 C-atoms wherein optionally 1 to 3 $CH_2$-groups are substituted by —O—, —S—, —SO—, —SO$_2$—, —NR—, —OCO—, —NRCONR'—, —NRCO—, —NRSO$_2$R'—, —COO—, —CONR— or —CH═CH— and wherein optionally 1 to 11 H-atoms are substituted by F or Cl, $R^1$, $R^2$, $R^3$, $R^4$ are independently from one another selected from the group consisting of Hal, E, OR, NRR', SOR, SO$_2$R, SO$_2$NRR', CN, COOR, CONRR', NRCONR'R", NRSO$_2$R', NRCOR', a linear or branched alkyl containing 1 to 10 C-atoms which is unsubstituted or mono-, di- or trisubstituted by ═S, ═NR, ═O, E, OR, NRR', SOR, SO$_2$R, SO$_2$NRR', CN, COOR, CONRR', NRCONR'R", NRSO$_2$R' or NRCOR', wherein optionally 1 to 3 $CH_2$-groups are substituted by —O—, —S—, —SO—, —SO$_2$—, —NR—, —OCO—, —NRCONR'—, —NRCO—, —NRSO$_2$R'—, —COO—, —CONR—, —C≡C— or —CH═CH— and wherein optionally 1 to 20 H-atoms are substituted by F or Cl, and a cycloalkyl or heterocyclyl containing 3 to 7 C-atoms which is unsubstituted or mono-, di- or trisubstituted by ═S, ═NR, ═O, E, OR, NRR', SOR, SO$_2$R, SO$_2$NRR', CN, COOR, CONRR', NRCONR'R", NRSO$_2$R' or NRCOR', wherein optionally 1 to 3 $CH_2$-groups are substituted by —O—, —S—, —SO—, —SO$_2$—, —NR—, —OCO—, —NRCONR—, —NRCO—, —NRSO$_2$R'—, —COO—, —CONR— and —CH═CH— and wherein optionally 1 to 11 H-atoms are substituted by F or Cl, R,R' independently from one another are selected from the group consisting of H, Hal, E, $R^5$, $OR^5$, $NR^5$, $SO_2R^5$, $SO_2NR^5R^6$, CN, $COOR^5$, $CONR^5R^6$, $NR^5CONR^5R^6$, $NR^5SO_2R^6$, $NR^5COR^6$, a linear or branched alkyl containing 1 to 10 C-atoms which is unsubstituted or mono-, di- or trisubstituted by ═S, ═$NR^5$, ═O, Hal, E, $R^5$, $OR^5$, $NR^5$, $SO_2R^5$, $SO_2NR^5R^6$, CN, $COOR^5$, $CONR^5R^6$, $NR^5CONR^5R^6$, $NR^5SO_2R^6$ or $NR^5COR^6$, wherein optionally 1 to 3 $CH_2$-groups are substituted by —O—, —S—, —SO—, —SO$_2$—, —$NR^5$, —OCO—, —$NR^5CONR^6$—, —$NR^5CO$—, —$NR^5SO_2R^6$—, —COO—, —$CONR^5$—, —C≡C— or —CH═CH— and wherein optionally 1 to 20 H-atoms are substituted by F or Cl, and a cycloalkyl or heterocyclyl containing 3 to 7 C-atoms which is unsubstituted or mono-, di- or trisubstituted by ═S, ═$NR^5$, ═O, Hal, E, $R^5$, $OR^5$, $NR^5$, $SO_2R^5$, $SO_2NR^5R^6$, CN, $COOR^5$, $CONR^5R^6$, $NR^5CONR^5R^6$, $NR^5SO_2R^6$ or $NR^5COR^6$, wherein optionally 1 to 3 $CH_2$-groups are substituted by —O—, —S—, —SO—, —SO$_2$—, —$NR^5$—, —OCO—, —$NR^5CONR^6$—, —$NR^5CO$—, —$NR^5SO_2R^6$—, —COO—, —CONR⁵- or —CH=CH— and wherein optionally 1 to 11 H-atoms are substituted by F or Cl, $R^5$, $R^6$ independently from one another are H, alkyl or a mono- or bicyclic saturated, unsaturated or aromatic hydrocarboncycle or heterocyle with 1 to 4 heteroatoms selected from N, O and S $R^7$ is H or alkyl containing 1 to 7 C-atoms, and Hal F, Cl, Br or I, and physiologically acceptable salts, derivatives, solvates, prodrugs and stereoisomers thereof, including mixtures thereof in all ratios.

The invention preferably relates to all above-mentioned compounds of the formula I in which E is

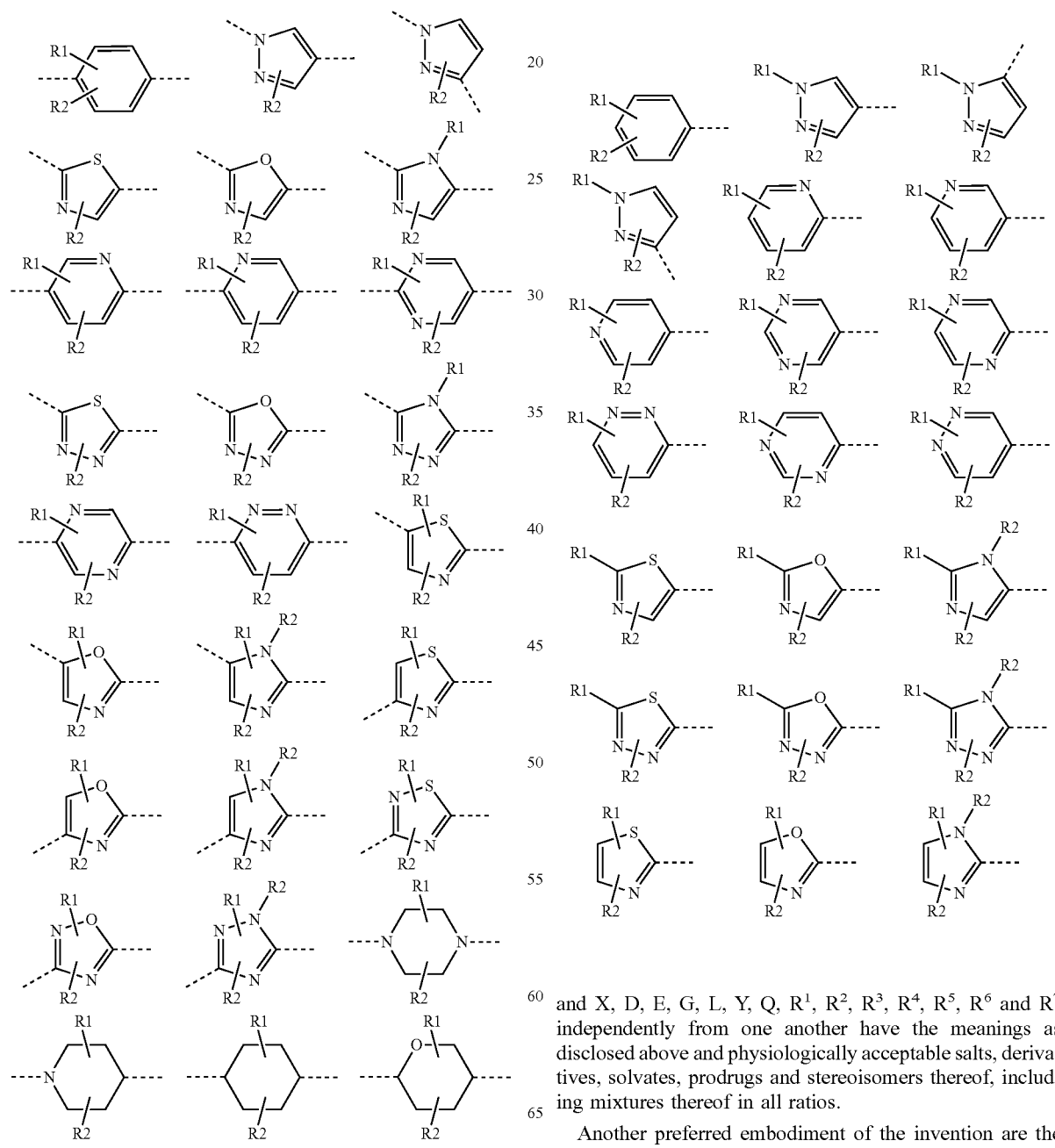

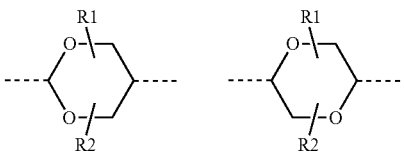

and X, D, G, K, L, Y, Q, $R^1$, $R^2$, $R^3$, $R^4$, $R^5$, $R^6$ and $R^7$ independently from one another have the meanings as disclosed above and physiologically acceptable salts, derivatives, solvates, prodrugs and stereoisomers thereof, including mixtures thereof in all ratios.

Another preferred embodiment of the invention are the above-mentioned compounds of the formula I in which K is and X, D, E, G, L, Y, Q, $R^1$, $R^2$, $R^3$, $R^4$, $R^5$, $R^6$ and $R^7$ independently from one another have the meanings as disclosed above and physiologically acceptable salts, derivatives, solvates, prodrugs and stereoisomers thereof, including mixtures thereof in all ratios.

Another preferred embodiment of the invention are the above-mentioned compounds of the formula I in which Q is

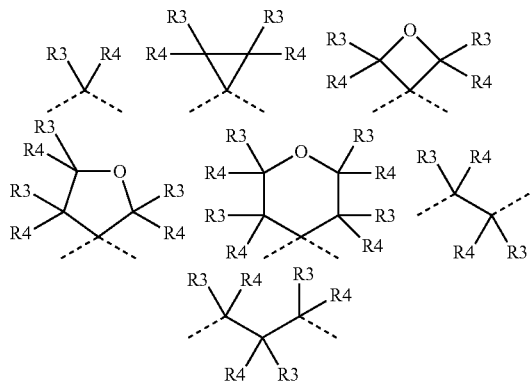

and X, D, E, G, K, L, Y, $R^1$, $R^2$, $R^3$, $R^4$, $R^5$, $R^6$ and $R^7$ independently from one another have the meanings as disclosed above and physiologically acceptable salts, derivatives, solvates, prodrugs and stereoisomers thereof, including mixtures thereof in all ratios.

Another preferred embodiment of the invention are the above-mentioned compounds of the formula I in which R1, R2 are independently from one another a linear or branched alkyl containing 1 to 5 C-atoms which is unsubstituted or mono-, di- or trisubstituted by E, OR, NRR', COOR, CONRR', NRCOR' or NRCONR'R", wherein optionally 1 to 3 are substituted by —O—, —NR—, —OCO—, —NRCONR'—, —NRCO—, —COO— or —CONR— and wherein optionally 1 to 10 H-atoms are substituted by F, or a cycloalkyl containing 3 to 6 C-atoms which is unsubstituted or mono-, di- or trisubstituted by E, OR, NRR', COOR, CONRR', NRCOR' or NRCONR'R", wherein optionally 1 to 3 $CH_2$-groups are substituted by —O—, —NR—, —OCO—, —NRCONR'—, —NRCO—, —COO— or —CONR— and wherein optionally 1 to 10 H-atoms are substituted by F, and X, D, E, G, K, L, Q, Y, $R^3$, $R^4$, $R^5$, $R^6$ and $R^7$ independently from one another have the meanings as disclosed above and physiologically acceptable salts, derivatives, solvates, prodrugs and stereoisomers thereof, including mixtures thereof in all ratios.

Another more preferred embodiment of the invention are the above-mentioned compounds of the formula I in which R1, R2 are independently from one another methyl, ethyl, propyl, cyclopropyl, isopropyl, butyl, isobutyl, 2-butyl, tert-butyl, cyclobutyl, OH or OR, which is unsubstituted or mono-, di- or trisubstituted by E or OR and wherein optionally 1 to 3 $CH_2$-groups are substituted by —O— or —NR— and wherein optionally 1 to 10 H-atoms are substituted by F, and X, D, E, G, K, L, Q, Y, $R^3$, $R^4$, $R^5$, $R^6$ and $R^7$ independently from one another have the meanings as disclosed above and physiologically acceptable salts, derivatives, solvates, prodrugs and stereoisomers thereof, including mixtures thereof in all ratios.

A particularly preferred embodiment of the present invention are compounds of the formula I in which E is

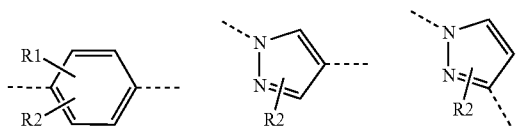

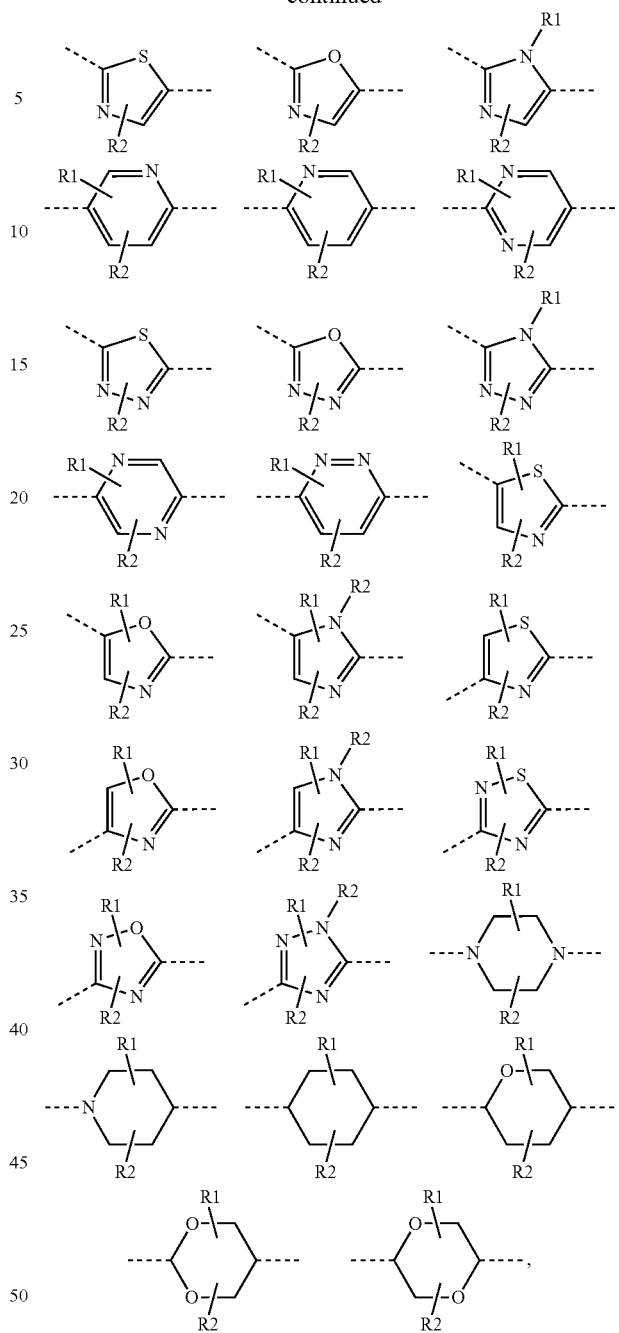

K is

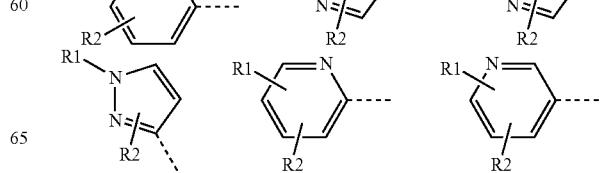

-continued

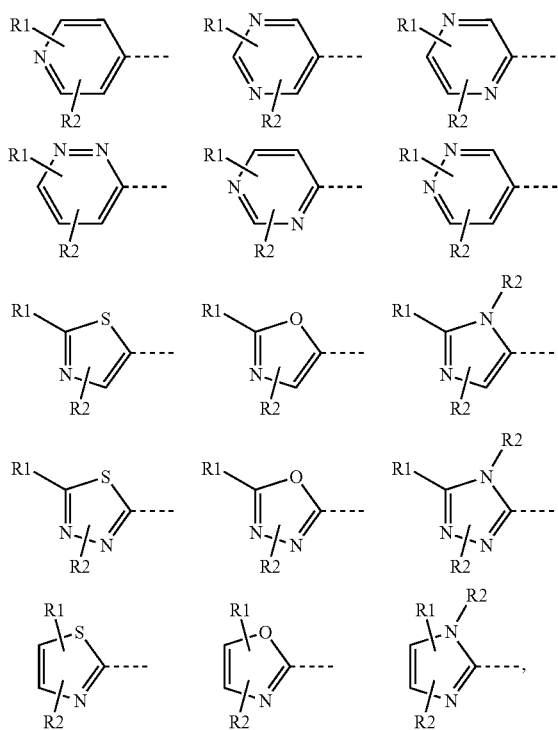

Q is

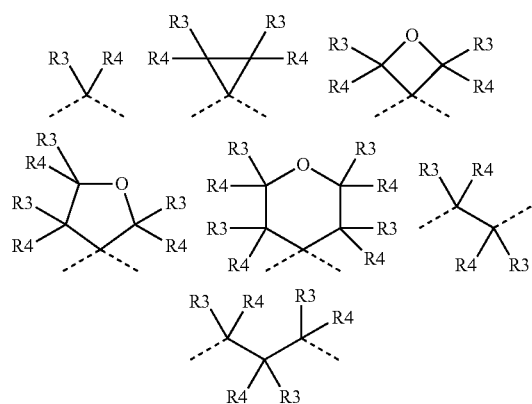

and X, D, G, L, Y, $R^1$, $R^2$, $R^3$, $R^4$, $R^5$, $R^6$ and $R^7$ independently from one another have the meanings as disclosed above and physiologically acceptable salts, derivatives, solvates, prodrugs and stereoisomers thereof, including mixtures thereof in all ratios.

Another particularly preferred embodiment of the present invention are compounds of the formula I in which E is

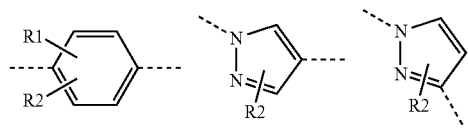

-continued

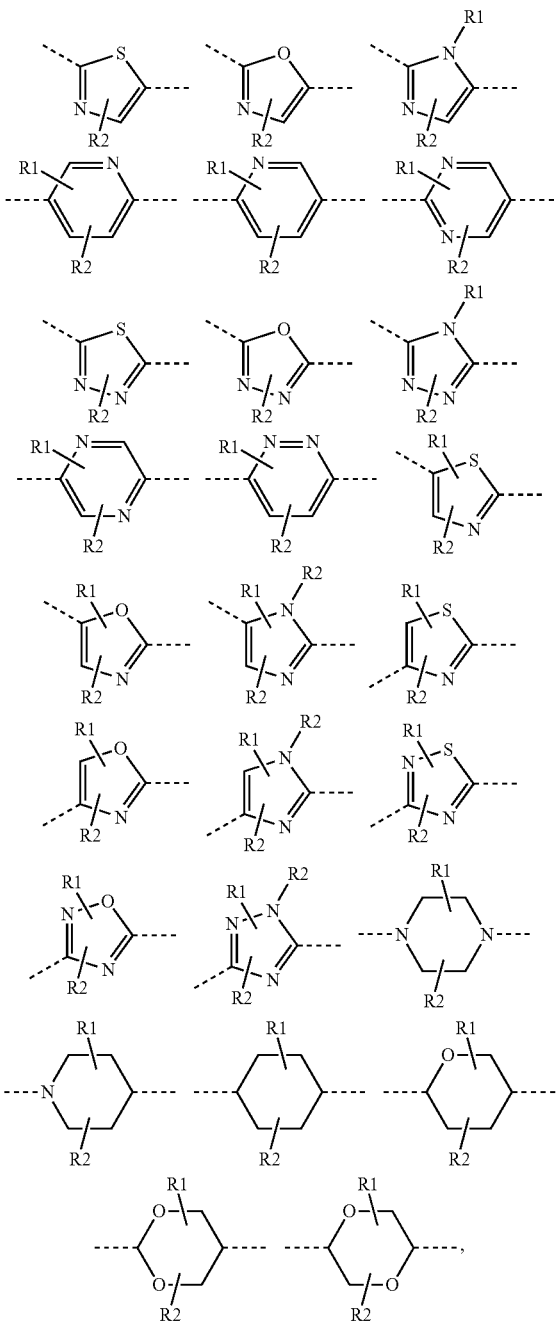

K is

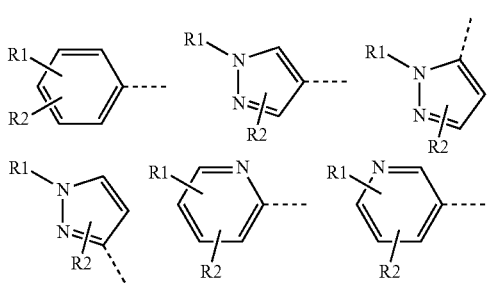

E is

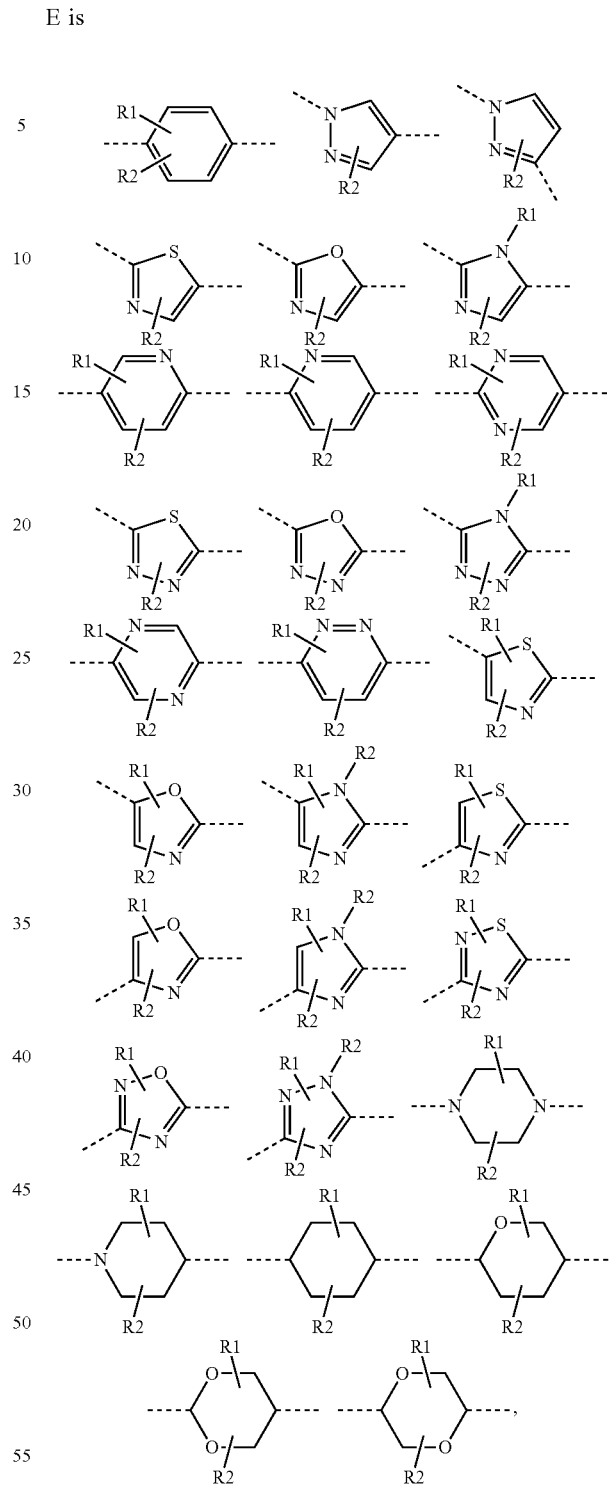

-continued

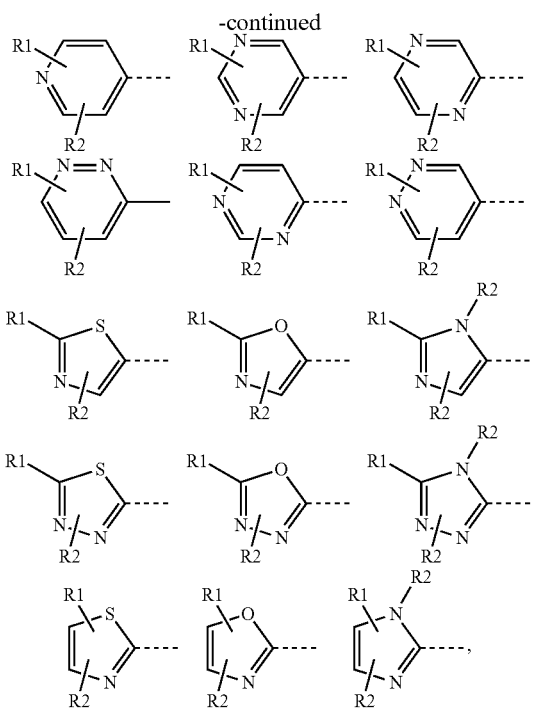

Q is

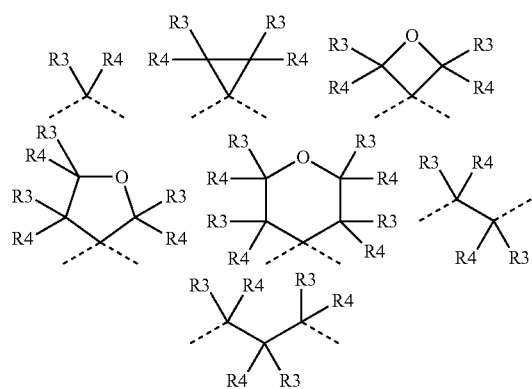

R¹, R² are independently from one another a linear or branched alkyl containing 1 to 5 C-atoms which is unsubstituted or mono-, di- or trisubstituted by E, OR, NRR', COOR, CONRR', NRCOR' or NRCONR'R", wherein optionally 1 to 3 CH₂-groups are substituted by —O—, —NR—, —OCO—, —NRCONR'—, —NRCO—, —COO— or —CONR— and wherein optionally 1 to 10 H-atoms are substituted by F, or a cycloalkyl containing 3 to 6 C-atoms which is unsubstituted or mono-, di- or trisubstituted by E, OR, NRR', COOR, CONRR', NRCOR' or NRCONR'R", wherein optionally 1 to 3 CH₂-groups are substituted by —O—, —NR—, —OCO—, —NRCONR'—, —NRCO—, —COO— or —CONR— and wherein optionally 1 to 10 H-atoms are substituted by F, and X, D, G, L, Y, R³, R⁴, R⁵, R⁶ and R⁷ independently from one another have the meanings as disclosed above and physiologically acceptable salts, derivatives, solvates, prodrugs and stereoisomers thereof, including mixtures thereof in all ratios.

Another particularly preferred embodiment of the present invention are compounds of the formula I in which K is

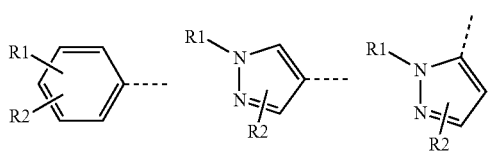

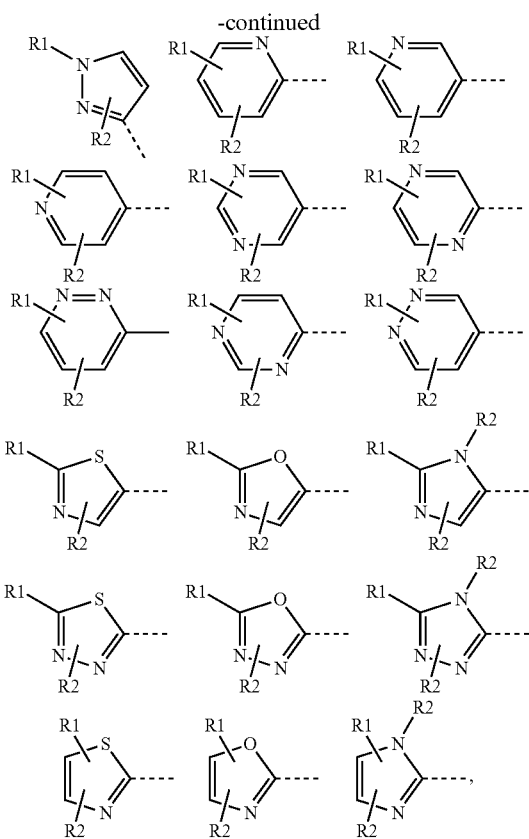

Q is

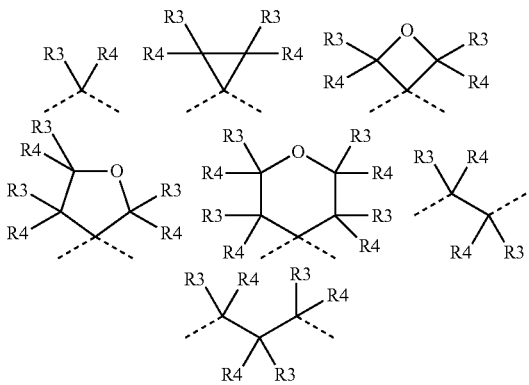

R¹, R² are independently from one another methyl, ethyl, propyl, cyclopropyl, isopropyl, butyl, isobutyl, 2-butyl, tert-butyl, cyclobutyl, OH or OR, which is unsubstituted or mono-, di- or trisubstituted by E or OR and wherein optionally 1 to 3 CH$_2$-groups are substituted by —O— or —NR— and wherein optionally 1 to 10 H-atoms are substituted by F, and X, D, G, L, Y, R³, R⁴, R⁵, R⁶ and R⁷ independently from one another have the meanings as disclosed above and physiologically acceptable salts, derivatives, solvates, prodrugs and stereoisomers thereof, including mixtures thereof in all ratios.

Very particular preference is given to the following compounds of the formula I selected from the group consisting of a) 4-[(Biphenyl-4-carbonyl)-amino]-2-methyl-4-(3,4,5-trimethoxy-benzylcarbamoyl)-butyric acid
b) (2S,4S)-4-[2-(4-Fluoro-phenyl)-1,1-dimethyl-ethylcarbamoyl]-4-{[5-(4-fluoro-phenyl)-thiazole-2-carbonyl]-amino}-2-methyl-butyric acid
c) (2S,4S)-4-[(Biphenyl-4-carbonyl)-amino]-4-[(S)-2-(4-fluoro-phenyl)-1-methyl-ethylcarbamoyl]-2-methyl-butyric acid
d) (2S,4S)-4-[(Biphenyl-4-carbonyl)-amino]-4-(1,1-dimethyl-2-pyridin-3-yl-ethylcarbamoyl)-2-methyl-butyric acid
e) (2S,4S)-4-[(Biphenyl-4-carbonyl)-amino]-4-[2-(4-fluoro-phenyl)-1,1-dimethyl-ethylcarbamoyl]-2-methyl-butyric acid
f) (2S,4S)-2-Benzyl-4-[(biphenyl-4-carbonyl)-amino]-4-[2-(4-fluoro-phenyl)-1,1-dimethyl-ethylcarbamoyl]-butyric acid
g) (2S,4S)-2-[(Biphenyl-4-carbonyl)-amino]-2-[2-(4-fluoro-phenyl)-1,1-dimethyl-ethylcarbamoyl]-ethyl}-pentanoic acid
h) (2S,4S)-4-[(Biphenyl-4-carbonyl)-amino]-4-[2-(4-fluoro-phenyl)-1,1-dimethyl-ethylcarbamoyl]-2-methoxymethyl-butyric acid
i) (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid
j) (2S,4S)-4-[2-(4-Fluoro-phenyl)-1,1-dimethyl-ethylcarbamoyl]-2-methyl-4-(4-pyridin-2-yl-benzoylamino)-butyric acid
k) (2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid
l) (2S,4S)-4-[2-(4-Fluoro-phenyl)-1,1-dimethyl-ethylcarbamoyl]-4-{[1-(4-fluoro-phenyl)-piperidine-4-carbonyl]-amino}-2-methyl-butyric acid
m) 4-[2-(4-Fluoro-phenyl)-1,1-dimethyl-ethylcarbamoyl]-2-methyl-4-[(5-phenyl-pyridine-2-carbonyl)-amino]-butyric acid
n) (2S,4S)-4-[2-(4-Fluoro-phenyl)-1,1-dimethyl-ethylcarbamoyl]-2-methyl-4-[(6-phenyl-pyridine-3-carbonyl)-amino]-butyric acid
o) (2S,4S)-4-[2-(4-Fluoro-phenyl)-1,1-dimethyl-ethylcarbamoyl]-2-methyl-4-[(4-phenyl-piperazine-1-carbonyl)-amino]-butyric acid
p) (2S,4S)-4-[2-(4-Fluoro-phenyl)-1,1-dimethyl-ethylcarbamoyl]-2-methyl-4-(4-pyridin-3-yl-benzoylamino)-butyric acid
q) (2S,4S)-4-[2-(4-Fluoro-phenyl)-1,1-dimethyl-ethylcarbamoyl]-2-methyl-4-[4-(5-methyl-thiazol-2-yl)-benzoylamino]-butyric acid
r) (2S,4S)-4-[2-(4-Fluoro-phenyl)-1,1-dimethyl-ethylcarbamoyl]-4-{[2-(4-fluoro-phenyl)-thiazole-5-carbonyl]-amino}-2-methyl-butyric acid
s) (2S,4S)-4-[2-(4-Fluoro-phenyl)-1,1-dimethyl-ethylcarbamoyl]-2-methyl-4-(4-pyrazol-1-yl-benzoylamino)-butyric acid
t) (2S,4S)-4-Amino-4-[2-(4-fluoro-phenyl)-1,1-dimethyl-ethylcarbamoyl]-2-methyl-butyric acid methyl ester
u) 2S,4S)-4-[2-(4-Fluoro-phenyl)-1,1-dimethyl-ethylcarbamoyl]-2-methyl-4-[(6-phenyl-pyridine-3-carbonyl)-amino]-butyric acid methyl ester
v) (2S,4S)-4-[2-(4-Fluoro-phenyl)-1,1-dimethyl-ethylcarbamoyl]-2-methyl-4-(4-pyridin-3-yl-benzoylamino)-butyric acid methyl ester
w) 2S,4S)-4-[2-(4-Fluoro-phenyl)-1,1-dimethyl-ethylcarbamoyl]-2-methyl-4-(4-pyridin-2-yl-benzoylamino)-butyric acid methyl ester
x) (2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid methyl ester y) (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid methyl ester
z) (2S,4S)-4-[2-(4-Fluoro-phenyl)-1,1-dimethyl-ethylcarbamoyl]-4-{[5-(4-fluoro-phenyl)-thiazole-2-carbonyl]-amino}-2-methyl-butyric acid methyl ester
aa) (2S,4S)-4-[2-(4-Fluoro-phenyl)-1,1-dimethyl-ethylcarbamoyl]-4-{[2-(4-fluoro-phenyl)-thiazole-5-carbonyl]-amino}-2-methyl-butyric acid methyl ester
bb) (2S,4S)-4-[2-(4-Fluoro-phenyl)-1,1-dimethyl-ethylcarbamoyl]-2-methyl-4-[4-(5-methyl-thiazol-2-yl)-benzoylamino]-butyric acid methyl ester
cc) (2S,4S)-4-[2-(4-Fluoro-phenyl)-1,1-dimethyl-ethylcarbamoyl]-4-{[1-(4-fluoro-phenyl)-piperidine-4-carbonyl]-amino}-2-methyl-butyric acid methyl ester
dd) (2S,4S)-4-[2-(4-Fluoro-phenyl)-1,1-dimethyl-ethylcarbamoyl]-2-methyl-4-(4-pyrazol-1-yl-benzoylamino)-butyric acid methyl ester
ee) (2S,4S)-4-[2-(4-Fluoro-phenyl)-1,1-dimethyl-ethylcarbamoyl]-2-methyl-4-[(4-phenyl-piperidine-1-carbonyl)-amino]-butyric acid methyl ester
ff) 2S,4S)-4-[2-(4-Fluoro-phenyl)-1,1-dimethyl-ethylcarbamoyl]-2-methyl-4-[(4-phenyl-piperazine-1-carbonyl)-amino]-butyric acid methyl ester
gg) (2S,4S)-4-[(Biphenyl-4-carbonyl)-amino]-2-methyl-4-(3,4,5-trimethoxy-benzylcarbamoyl)-butyric acid methyl ester
hh) (2S,4S)-4-[(Biphenyl-4-carbonyl)-amino]-4-[2-(4-fluoro-phenyl)-1-methyl-ethylcarbamoyl]-2-methyl-butyric acid methyl ester
ii) (2S,4S)-4-[(Biphenyl-4-carbonyl)-amino]-4-(1,1-dimethyl-2-pyridin-3-yl-ethylcarbamoyl)-2-methyl-butyric acid methyl ester
jj) (2S,4S)-4-[2-(4-Fluoro-phenyl)-1,1-dimethyl-ethylcarbamoyl]-2-methyl-4-(4-pyrazin-2-yl-benzoylamino)-butyric acid
kk) (2S,4S)-4-[(Biphenyl-4-carbonyl)-amino]-2-methyl-4-(1,1,3-trimethyl-butylcarbamoyl)-butyric acid
ll) (2S,4S)-4-[2-(4-Fluoro-phenyl)-1,1-dimethyl-ethylcarbamoyl]-2-methyl-4-[(5-phenyl-pyrazine-2-carbonyl)-amino]-butyric acid
mm) (2S,4S)-4-[2-(4-Fluoro-phenyl)-1,1-dimethyl-ethylcarbamoyl]-2-methyl-4-(4-pyrazol-1-yl-benzoylamino)-butyric acid
nn) (2S,4S)-4-[4-(1-Difluoromethyl-1H-pyrazol-4-yl)-benzoylamino]-4-[2-(4-fluoro-phenyl)-1,1-dimethyl-ethylcarbamoyl]-2-methyl-butyric acid
oo) (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid
pp) (S)-4-[(Biphenyl-4-carbonyl)-amino]-4-[2-(4-fluoro-phenyl)-1,1-dimethyl-ethylcarbamoyl]-2,2-dimethyl-butyric acid
qq) (2S,4S)-4-[(Biphenyl-4-carbonyl)-amino]-4-[3-(4-fluoro-benzyl)-oxetan-3-ylcarbamoyl]-2-methyl-butyric acid
rr) (2S,4S)-4-[(Biphenyl-4-carbonyl)-amino]-4-(1,1-dimethyl-propylcarbamoyl)-2-methyl-butyric acid
and physiologically acceptable salts, derivatives, solvates, prodrugs and stereoisomers thereof, including mixtures thereof in all ratios.

If the above-mentioned amino acids can occur in a plurality of enantiomeric forms, all these forms and also mixtures thereof (for example DL forms) are included above and below.

Furthermore, the abbreviations have the following meanings:
Boc tert-butoxycarbonyl
CBZ benzyloxycarbonyl
DNP 2,4-dinitrophenyl
FMOC 9-fluorenylmethoxycarbonyl
imi-DNP 2,4-dinitrophenyl in the 1-position of the imidazole ring
OMe methyl ester
POA phenoxyacetyl
DCCI dicyclohexylcarbodiimide
HOBt 1-hydroxybenzotriazole
CDI Carbonyldiimidazole
DCM Dichlormethane
DMA Dimethylacetamide
DMF Dimethylformamide
EDCI 1-Ethyl-3-(3-dimethylaminopropyl)carbodiimide Hydrochloride
MTBE Methyl-tert-butylether
PE Petrol ether
RT room temperature
TFA Trifluoro acetic acid
THF Tetrahydrofurane
NMO N-Methyl morpholine
T3P Propylphosphonic Anhydride Hal denotes fluorine, chlorine, bromine or iodine, in particular fluorine or chlorine.

A is an unbranched (linear), branched or cyclic hydrocarbon chain and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl.

Cyclic alkyl or cycloalkyl preferably denotes (if A is cyclic it denotes) cyclopropyl, cyclobutyl, cyclopentyl, cyclohexyl or cycloheptyl.

=O is cabonyloxygen,

Additionally, A denotes also alkenyl such as ethenyl, propylenyl, butenyl and the like.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Especially preferred is $C_1$-$C_5$alkyl. A $C_1$-$C_5$alkyl radical is for example a methyl, ethyl, propyl, isopropyl, butyl, isobutyl, tert-butyl or pentyl.

"Aryl", Ar" or "aromatic hydrocarbon residue" means a mono- or polycyclic aromatic ring system containing carbon ring atoms. The preferred aryls are monocyclic or bicyclic 6-10 membered aromatic ring systems. Examples of "aryl" groups include, but are not limited to Phenyl, 2-naphthyl, 1-naphthyl, biphenyl, indanyl as well as substituted derivatives thereof. The most preferred aryl is phenyl.

"Heterocycle" and "heterocyclyl" refer to saturated or unsaturated non-aromatic rings or ring systems containing at least one heteroatom selected from O. S and N. further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O. S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoxazolyl, isoindolyl, dihydrobenzothienyl, indolizinyl, cinnolinyl, phthalazinyl, quinazolinyl, naphthyridinyl, carbazolyl, benzdioxinyl, benzodioxolyl, quinoxalinyl, purinyl, furazanyl, thiophenyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

All physiologically acceptable salts, derivatives, solvates and stereoisomers of these compounds, including mixtures thereof in all ratios, are also in accordance with the invention.

The invention also relates to the optically active forms (stereoisomers), the enantiomers, the racemates, the diastereomers and hydrates and solvates of these compounds.

Compounds of the formula I according to the invention may be chiral owing to their molecular structure and may accordingly occur in various enantiomeric forms. They may therefore be in racemic or optically active form. Since the pharmaceutical efficacy of the racemates or stereoisomers of the compounds according to the invention may differ, it may be desirable to use the enantiomers. In these cases, the end product, but also even the intermediates, may be separated into enantiomeric compounds by chemical or physical measures known to the person skilled in the art or already employed as such in the synthesis.

Particularly preferred is the following stereoisomer of the compounds of formula I:

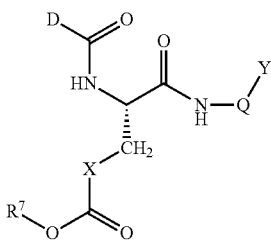

I

Pharmaceutically or physiologically acceptable derivatives are taken to mean, for example, salts of the compounds according to the invention and also so-called prodrug compounds. Prodrug compounds are taken to mean compounds of the formula I which have been modified with, for example, alkyl or acyl groups, sugars or oligopeptides and which are rapidly cleaved or liberated in the organism to form the effective compounds according to the invention. Prodrugs of the compounds of the present invention are for example the ester compounds Nos. 22-37 of table 1a, wherein the residue $R^7$ is rapidly cleaved or liberated in the organism to form the effective compound according to the invention. Prodrugs also include biodegradable polymer derivatives of the compounds according to the invention, as described, for example, in Int. J. Pharm. 115(1995), 61-67.

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates or p-toluenesulfonates.

Solvates of the compounds of the formula I are taken to mean adductions of inert solvent molecules onto the compounds of the formula I which form owing to their mutual attractive force. Solvates are, for example, hydrates, such as monohydrates or dihydrates, or alcoholates, i.e. addition compounds with alcohols, such as, for example, with methanol or ethanol.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. They are particularly preferably mixtures of two stereoisomeric compounds. Another embodiment of the present invention is a process for the preparation of the compounds of the formula I, characterized in that the compounds are prepared by stepwise reactions of building blocks (see example 2).

It is possible to carry out the reactions stepwise in each case and to modify the sequence of the linking reactions of the building blocks with adaptation of the protecting-group concept.

The starting materials or starting compounds are generally known. If they are novel, they can be prepared by methods known per se.

If desired, the starting materials can also be formed in situ by not isolating them from the reaction mixture, but instead immediately converting them further into the compounds of the formula I.

The compounds of the formula I are preferably obtained by liberating them from their functional derivatives by solvolysis, in particular by hydrolysis, or by hydrogenolysis. Preferred starting materials for the solvolysis or hydrogenolysis are those which contain correspondingly protected amino, carboxyl and/or hydroxyl groups instead of one or more free amino, carboxyl and/or hydroxyl groups, preferably those which carry an amino-protecting group instead of an H atom which is connected to an N atom. Preference is furthermore given to starting materials which carry a hydroxyl-protecting group instead of the H atom of a hydroxyl group. Preference is also given to starting materials which carry a protected carboxyl group instead of a free carboxyl group. It is also possible for a plurality of identical or different protected amino, carboxyl and/or hydroxyl groups to be present in the molecule of the starting material. If the protecting groups present are different from one another, they can in many cases be cleaved off selectively.

The functional derivatives of the compounds of the formula I to be used as starting materials can be prepared by known methods of amino-acid and peptide synthesis, as described, for example, in the said standard works and patent applications.

The compounds of the formula I are liberated from their functional derivatives, depending on the protecting group used, for example, with the aid of strong acids, advantageously using trifluoroacetic acid or perchloric acid, but also using other strong inorganic acids, such as hydrochloric acid or sulfuric acid, strong organic acids, such as trichloroacetic acid, or sulfonic acids, such as benzoyl- or p-toluenesulfonic acid. The presence of an additional inert solvent and/or a catalyst is possible, but is not always necessary.

Depending on the respective synthetic route, the starting materials can optionally be reacted in the presence of an inert solvent.

Suitable inert solvents are, for example, heptane, hexane, petroleum ether, DMSO, benzene, toluene, xylene, trichloroethylene, 1,2-dichloroethane, carbon tetrachloride, chloroform or dichloromethane; alcohols, such as methanol, ethanol, isopropanol, n-propanol, n-butanol or tert-butanol;

ethers, such as diethyl ether, diisopropyl ether (preferably for substitution on the indole nitrogen), tetrahydrofuran (THF) or dioxane; glycol ethers, such as ethylene glycol monomethyl or monoethyl ether, ethylene glycol dimethyl ether (diglyme); ketones, such as acetone or butanone; amides, such as acet-amide, dimethylacetamide, N-methylpyrrolidone (NMP) or dimethylformamide (DMF); nitriles, such as acetonitrile; esters, such as ethyl acetate, carboxylic acids or acid anhydrides, such as, for example, acetic acid or acetic anhydride, nitro compounds, such as nitromethane or nitrobenzene, optionally also mixtures of the said solvents with one another or mixtures with water.

The amount of solvent is not crucial; 10 g to 500 g of solvent can preferably be added per g of the compound of the formula I to be reacted.

It may be advantageous to add an acid-binding agent, for example an alkali or alkaline-earth metal hydroxide, carbonate or bicarbonate or other alkali or alkaline-earth metal salts of weak acids, preferably a potassium, sodium or calcium salt, or to add an organic base, such as, for example, triethylamine, dimethylamine, pyridine or quinoline, or an excess of the amine component.

The resultant compounds according to the invention can be separated from the corresponding solution in which they are prepared (for example by centrifugation and washing) and can be stored in another composition after separation, or they can remain directly in the preparation solution. The resultant compounds according to the invention can also be taken up in desired solvents for the particular use.

Suitable reaction temperatures are temperatures from 0 to 40° C., preferably 5 to 25° C.

The reaction duration depends on the reaction conditions selected. In general, the reaction duration is 0.5 hour to 10 days, preferably 1 to 24 hours. On use of a microwave, the reaction time can be reduced to values of 1 to 60 minutes.

The compounds of the formula I and also the starting materials for their preparation are, in addition, prepared by known methods, as described in the literature (for example in standard works, such as Houben-Weyl, Methoden der organischen Chemie [Methods of Organic Chemistry], Georg-Thieme-Verlag, Stuttgart), for example under reaction conditions which are known and suitable for the said reactions. Use can also be made here of variants known per se, which are not described here in greater detail.

Conventional work-up steps, such as, for example, addition of water to the reaction mixture and extraction, enable the compounds to be obtained after removal of the solvent. It may be advantageous, for further purification of the product, to follow this with a distillation or crystallisation or to carry out a chromatographic purification.

Another embodiment of the present invention is a process for the preparation of the compounds of the formula I, characterized in that
a) the base of a compound of the formula I is converted into one of its salts by treatment with an acid, or
b) an acid of a compound of the formula I is converted into one of its salts by treatment with a base.

An acid of the formula I can be converted into the associated addition salt using a base, for example by reaction of equivalent amounts of the acid and base in an inert solvent, such as ethanol, and subsequent evaporation. Suitable bases for this reaction are, in particular, those which give physiologically acceptable salts. Thus, the acid of the formula I can be converted into the corresponding metal salt, in particular alkali or alkaline-earth metal salt, using a base (for example sodium hydroxide, potassium hydroxide, sodium carbonate or potassium carbonate) or into the corresponding ammonium salt. Organic bases which give physiologically acceptable salts, such as, for example, ethanolamine, are also suitable for this reaction.

On the other hand, a base of the formula I can be converted into the associated acid-addition salt using an acid, for example by reaction of equivalent amounts of the base and acid in an inert solvent, such as ethanol, with subsequent evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic, mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, glu-conic acid, ascorbic acid, nicotinic acid, isonicotinic acid, methane- or ethanesulfonic acid, ethanedisulfonic acid, 2-hydroxysulfonic acid, benzene-sulfonic acid, p-toluenesulfonic acid, naphthalenemono- and -disulfonic acids or laurylsulfuric acid. Salts with physiologically unacceptable acids, for example picrates, can be used for the isolation and/or purification of the compounds of the formula I.

It has been found that the compounds of the formula I are well tolerated and have valuable pharmacological properties, since they selectively inhibit ADAMTS5.

The invention therefore furthermore relates to the use of compounds according to the invention for the preparation of a medicament for the treatment and/or prophylaxis of diseases which are caused, promoted and/or propagated by ADAMTS5 and/or by ADAMTS5-promoted signal transduction.

The invention thus also relates, in particular, to a medicament comprising at least one compound according to the invention and/or one of its physiologically acceptable salts, derivatives, prodrugs, solvates and stereoisomers, including mixtures thereof in all ratios, for use in the treatment and/or prophylaxis of physiological and/or pathophysiological states.

Particular preference is given, in particular, to physiological and/or pathophysiological states which are connected to ADAMTS5.

Physiological and/or pathophysiological states are taken to mean physiological and/or pathophysiological states which are medically relevant, such as, for example, diseases or illnesses and medical disorders, complaints, symptoms or complications and the like, in particular diseases.

The invention furthermore relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of osteoarthritis, rheumatoid arthritis, traumatic cartilage injuries, pain, allodynia, and hyperalgesia.

An especially preferred embodiment of the present invention is a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of osteoarthritis and pain.

The invention furthermore relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting osteoarthritis, traumatic cartilage injuries, pain, allodynia, hyperalgesia, rheumatoid arthritis, joint injury, reactive arthritis, cirrhosis, inflammatory diseases as inflammatory bowel disease, ulceratice colitis, gastritis, psoriasis, eczema and dermatitis, asthma, allergic reaction, chronic obstructive pulmonary disease, fibroid lung, acute respiratory distress (ARDS), lung infection, interstitial pneumonia, atherosclerosis, osteoporosis, age-related macular degeneration, myocardial infarction, corneal ulceration cancer, tumor metastasis and invasion, uncontrolled degradation of the extracellular matrix as in osteoarthritis, central nervous system diseases, abnormal wound healing, multiple sclerosis, angiogenesis and restenosis.

The invention furthermore preferably relates to a medicament comprising at least one compound according to the invention and/or one of its physiologically acceptable salts, derivatives, solvates and stereoisomers, including mixtures thereof in all ratios, for use in the treatment and/or prophylaxis of physiological and/or pathophysiological states, selected from the group consisting of osteoarthritis, traumatic cartilage injuries, pain, allodynia, hyperalgesia, rheumatoid arthritis, joint injury, reactive arthritis, central nervous system diseases, multiple sclerosis, angiogenesis cancer, tumor metastasis and invasion.

Especially preferred the invention relates to a medicament comprising at least one compound according to the invention comprising at least one compound according to one or more of claims 1 to 16 and/or one of its physiologically acceptable salts, derivatives, solvates and stereoisomers, including mixtures thereof in all ratios, for use in the treatment and/or prophylaxis of physiological and/or pathophysiological states, selected from the group consisting of osteoarthritis, rheumatoid arthritis, traumatic cartilage injuries, pain, allodynia, and hyperalgesia.

Pain is a complex sensory perception which, as an acute event, has the character of a warning and control signal, but as chronic pain has lost this and in this case (as chronic pain syndrome) should be regarded and treated today as an independent syndrome. Hyperalgesia is the term used in medicine for excessive sensitivity to pain and reaction to a stimulus which is usually painful. Stimuli which can trigger pain are, for example, pressure, heat, cold or inflammation. Hyperalgesia is a form of hyperaesthesia, the generic term for excessive sensitivity to a stimulus. Allodynia is the term used in medicine for the sensation of pain which is triggered by stimuli which do not usually cause pain.

It is intended that the medicaments disclosed above include a corresponding use of the compounds according to the invention for the preparation of a medicament for the treatment and/or prophylaxis of the above physiological and/or pathophysiological states.

It is additionally intended that the medicaments disclosed above include a corresponding method for the treatment and/or prophylaxis of the above physiological and/or pathophysiological states in which at least one compound according to the invention is administered to a patient in need of such a treatment.

The compounds according to the invention preferably exhibit an advantageous biological activity which can easily be demonstrated in enzyme assays and animal experiments, as described in the examples. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The compounds according to the invention can be administered to humans or animals, in particular mammals, such as apes, dogs, cats, rats or mice, and can be used in the therapeutic treatment of the human or animal body and in the combating of the above-mentioned diseases. They can furthermore be used as diagnostic agents or as reagents.

Furthermore, compounds according to the invention can be used for the isolation and investigation of the activity or expression of ADAMTS5. In addition, they are particularly suitable for use in diagnostic methods for diseases in connection with disturbed ADAMTS5 activity. The invention therefore furthermore relates to the use of the compounds according to the invention for the isolation and investigation of the activity or expression of ADAMTS5 or as binders and inhibitors of ADAMTS5.

For diagnostic purposes, the compounds according to the invention can, for example, be radioactively labelled. Examples of radioactive labels are $^3H$, $^{14}C$, $^{231}I$ and $^{125}I$. A preferred labelling method is the iodogen method (Fraker et al., 1978). In addition, the compounds according to the invention can be labelled by enzymes, fluorophores and chemophores. Examples of enzymes are alkaline phosphatase, β-galactosidase and glucose oxidase, an example of a fluorophore is fluorescein, an example of a chemophore is luminol, and automated detection systems, for example for fluorescent colorations, are described, for example, in U.S. Pat. Nos. 4,125,828 and 4,207,554.

The compounds of the formula I can be used for the preparation of pharmaceutical compositions, in particular by non-chemical methods. In this case, they are brought into a suitable dosage form together with at least one solid, liquid and/or semi-liquid excipient or adjuvant and optionally in combination with one or more further active ingredient(s).

The invention therefore furthermore relates to pharmaceutical compositions comprising at least one compound of the formula I and/or physiologically acceptable salts, derivatives, solvates, prodrugs and stereoisomers thereof, including mixtures thereof in all ratios. In particular, the invention also relates to pharmaceutical compositions which comprise further excipients and/or adjuvants, and also to pharmaceutical compositions which comprise at least one further medicament active ingredient.

In particular, the invention also relates to a process for the preparation of a pharmaceutical composition, characterised in that a compound of the formula I and/or one of its physiologically acceptable salts, derivatives, solvates, prodrugs and stereoisomers, including mixtures thereof in all ratios, is brought into a suitable dosage form together with a solid, liquid or semi-liquid excipient or adjuvant and optionally with a further medicament active ingredient.

The pharmaceutical compositions according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient carriers, it is also possible to use, for example, lubricants, stabilisers and/or wetting agents, emulsifiers, salts for influencing the osmotic pressure, antioxidants, dispersants, antifoams, buffer substances, flavours and/or aromas or flavour correctants, preservatives, solubilisers or dyes. If desired, compositions or medicaments according to the invention may comprise one or more further active ingredients, for example one or more vitamins.

The terms "pharmaceutical formulation" and "pharmaceutical composition" are used as synonyms for the purposes of the present invention.

As used here, "pharmaceutically tolerated" relates to medicaments, precipitation reagents, excipients, adjuvants, stabilisers, solvents and other agents which facilitate the administration of the pharmaceutical compositions obtained therefrom to a mammal without undesired physiological side effects, such as, for example, nausea, dizziness, digestion problems or the like.

In pharmaceutical compositions for parenteral administration, there is a requirement for isotonicity, euhydration and tolerability and safety of the formulation (low toxicity), of the adjuvants employed and of the primary pack-aging. Surprisingly, the compounds according to the invention preferably have the advantage that direct use is possible and further purification steps for the removal of toxicologically unacceptable agents, such as, for example, high concentrations of organic solvents or other toxicologically unacceptable adjuvants, are thus unnecessary before use of the compounds according to the invention in pharmaceutical formulations.

The invention particularly preferably also relates to pharmaceutical compositions comprising at least one compound according to the invention in precipitated non-crystalline, precipitated crystalline or in dissolved or suspended form, and optionally excipients and/or adjuvants and/or further pharmaceutical active ingredients.

The solid compounds according to the invention preferably enable the preparation of highly concentrated formulations without unfavourable, undesired aggregation of the compounds according to the invention occurring. Thus, ready-to-use solutions having a high active-ingredient content can be prepared with the aid of compounds according to the invention with aqueous solvents or in aqueous media.

The compounds and/or physiologically acceptable salts and solvates thereof can also be lyophilised and the resultant lyophilisates used, for example, for the preparation of injection preparations.

Aqueous compositions can be prepared by dissolving or suspending compounds according to the invention in an aqueous solution and optionally adding adjuvants. To this end, defined volumes of stock solutions comprising the said further adjuvants in defined concentration are advantageously added to a solution or suspension having a defined concentration of compounds according to the invention, and the mixture is optionally diluted with water to the pre-calculated concentration. Alternatively, the adjuvants can be added in solid form. The amounts of stock solutions and/or water which are necessary in each case can subsequently be added to the aqueous solution or suspension obtained. Compounds according to the invention can also advantageously be dissolved or suspended directly in a solution comprising all further adjuvants.

The solutions or suspensions comprising compounds according to the invention and having a pH of 4 to 10, preferably having a pH of 5 to 9, and an osmolality of 250 to 350 mOsmol/kg can advantageously be prepared. The pharmaceutical composition can thus be administered directly substantially without pain intravenously, intra-arterially, intra-articularly, subcutaneously or percutaneously. In addition, the preparation may also be added to infusion solutions, such as, for example, glucose solution, isotonic saline solution or Ringer's solution, which may also contain further active ingredients, thus also enabling relatively large amounts of active ingredient to be administered.

Pharmaceutical compositions according to the invention may also comprise mixtures of a plurality of compounds according to the invention.

The compositions according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.).

For example, the compounds according to the invention can be stored in a stable manner by drying and when necessary converted into a ready-to-use pharmaceutical composition by dissolution or suspension. Possible drying methods are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a medicament or of a pharmaceutical active ingredient which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improved treatment, healing, prevention or elimination of a disease, syndrome, disease state, complaint, disorder or prevention of side effects or also a reduction in the progress of a disease, complaint or disorder. The term "therapeutically effective amount" also encompasses the amounts which are effective for increasing normal physiological function.

On use of compositions or medicaments according to the invention, the compounds according to the invention and/or physiologically acceptable salts and solvates thereof are generally used analogously to known, commercially available compositions or preparations, preferably in dosages of between 0.1 and 500 mg, in particular 5 and 300 mg, per use unit. The daily dose is preferably between 0.001 and 250 mg/kg, in particular 0.01 and 100 mg/kg, of body weight. The composition can be administered one or more times per day, for example two, three or four times per day. However, the individual dose for a patient depends on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active ingredient in an organism is its bioavailability. If the medicament active ingredient is delivered to the organism intravenously in the form of an injection solution, its absolute bioavailability, i.e. the proportion of the pharmaceutical which reaches the systemic blood, i.e. the major circulation, in unchanged form, is 100%. In the case of oral administration of a therapeutic active ingredient, the active ingredient is generally in the form of a solid in the formulation and must therefore first be dissolved in order that it is able to overcome the entry barriers, for example the gastrointestinal tract, the oral mucous membrane, nasal membranes or the skin, in particular the stratum corneum, or can be absorbed by the body. Data on the pharmacokinetics, i.e. on the bioavailability, can be obtained analogously to the method of J. Shaffer et al., J. Pharm. Sciences, 88 (1999), 313-318.

Furthermore, medicaments of this type can be prepared by means of one of the processes generally known in the pharmaceutical art.

Medicaments can be adapted for administration via any desired suitable route, for example by the oral (including buccal or sublingual), rectal, pulmonary, nasal, topical (including buccal, sublingual or transdermal), vaginal or parenteral (including subcutaneous, intramuscular, intravenous, intradermal and in particular intra-articular) routes. Medicaments of this type can be prepared by means of all processes known in the pharmaceutical art by, for example, combining the active ingredient with the excipient(s) or adjuvant(s).

Parenteral administration is preferably suitable for administration of the medicaments according to the invention. In the case of parenteral administration, intra-articular administration is particularly preferred.

The invention thus preferably also relates to the use of a pharmaceutical composition according to the invention for intra-articular administration in the treatment and/or prophylaxis of physiological and/or pathophysiological states selected from the group consisting of osteoarthritis, traumatic cartilage injuries, pain, allodynia or hyperalgesia.

Intra-articular administration has the advantage that the compound according to the invention can be administered directly into the synovial fluid in the vicinity of the joint cartilage and is also able to diffuse from there into the cartilage tissue. Pharmaceutical compositions according to the invention can thus also be injected directly into the joint gap and thus develop their action directly at the site of action as intended. The compounds according to the invention are also suitable for the preparation of medicaments to be administered parenterally having slow, sustained and/or controlled release of active ingredient. They are thus also suitable for the preparation of delayed-release formulations, which are advantageous for the patient since administration is only necessary at relatively large time intervals.

Particularly preferred is the use of a pharmaceutical composition according to the invention for intra-articular administration in the treatment and/or prophylaxis of physiological and/or pathophysiological states selected from the group consisting of osteoarthritis, rheumatoid arthritis, traumatic cartilage injuries, pain, allodynia, and hyperalgesia.

The medicaments adapted to parenteral administration include aqueous and non-aqueous sterile injection solutions comprising antioxidants, buffers, bacteriostatics and solutes, by means of which the formulation is rendered isotonic with the blood or synovial fluid of the recipient to be treated; as well as aqueous and non-aqueous sterile suspensions, which can comprise suspension media and thickeners. The formulations can be delivered in single-dose or multi-dose containers, for example sealed ampoules and vials, and stored in the freeze-dried (lyophilised) state, so that only the addition of the sterile carrier liquid, for example water for injection purposes, immediately before use is necessary. Injection solutions and suspensions prepared in accordance with the formulation can be prepared from sterile powders, granules and tablets.

The compounds according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention can also be coupled to soluble polymers as targeted medicament excipients. Such polymers can encompass polyvinylpyrrolidone, pyran copolymer, polyhydroxypropylmethacryl-amidophenol, polyhydroxyethylaspartamidophenol or polyethylene oxide polylysine, substituted by palmitoyl radicals. The compounds according to the invention can furthermore be coupled to a class of biodegradable polymers which are suitable for achieving slow release of a medicament, for example polylactic acid, poly-epsilon-caprolactone, polyhydroxybutyric acid, polyorthoesters, polyacetals, polydihydroxypyrans, polycyanoacrylates, polylactic-co-glycolic acid, polymers, such as conjugates between dextran and methacrylates, polyphosphoesters, various polysaccharides and polyamines and poly-ϵ-caprolactone, albumin, chitosan, collagen or modified gelatine and cross-linked or amphipathic block copolymers of hydrogels.

Suitable for enteral administration (oral or rectal) are, in particular, tablets, dragees, capsules, syrups, juices, drops or suppositories, and suitable for topical use are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Also particularly suitable for topical uses are liposomal compositions.

In the case of formulation to give an ointment, the active ingredient can be employed either with a paraffinic or a water-miscible cream base. Alternatively, the active ingredient can be formulated to a cream with an oil-in-water cream base or a water-in-oil base.

Medicaments adapted to transdermal administration can be delivered as independent plasters for extended, close contact with the epidermis of the recipient. Thus, for example, the active ingredient can be supplied from the plaster by means of iontophoresis, as described in general terms in Pharmaceutical Research, 3(6), 318 (1986).

It goes without saying that, besides the constituents particularly mentioned above, the medicaments according to the invention may also comprise other agents usual in the art with respect to the particular type of pharmaceutical formulation.

The invention also relates to a set (kit) consisting of separate packs of
a) an effective amount of a compound of the formula I and/or physiologically acceptable salts, derivatives, solvates, prodrugs and stereoisomers thereof, including mixtures thereof in all ratios, and
b) an effective amount of a further medicament active ingredient.

The set comprises suitable containers, such as boxes or cartons, individual bottles, bags or ampoules. The set may, for example, comprise separate ampoules each containing an effective amount of a compound of the formula I and/or pharmaceutically acceptable derivatives, solvates, prodrugs and stereoisomers thereof, including mixtures thereof in all ratios, and an effective amount of a further medicament active ingredient in dissolved or lyophilised form.

Furthermore, the medicaments according to the invention can be used in order to provide additive or synergistic effects in certain known therapies and/or can be used in order to restore the efficacy of certain existing therapies.

Besides the compounds according to the invention, the pharmaceutical compositions according to the invention may also comprise further medicament active ingredients, for example for use in the treatment of osteoarthritis other DDR2 inhibitors, cathepsin D inhibitors, ADAMTS5 inhibitors, NSAIDS, Cox-2 inhibitors, glucocorticoids, hyaluronic acid, azathioprine, methotrexate, anti-CAM antibodies, such as, for example, anti-ICAM-1 antibody, FGF-18. For the treatment of the other diseases mentioned, the pharmaceutical compositions according to the invention may also, besides the compounds according to the invention, comprise further medicament active ingredients which are known to the person skilled in the art in the treatment thereof.

Even without further comments, it is assumed that a person skilled in the art will be able to use the above description in the broadest scope. The preferred embodiments should therefore merely be regarded as descriptive disclosure which is absolutely not limiting in any way.

The following examples are thus intended to explain the invention without limiting it. Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

Rf values on silica gel; mass spectrometry: El (electron impact ionisation): M+, FAB (fast atom bombardment): (M+H)+, THF (tetrahydrofuran), NMP (N-methylpyrrolidone), DMSO (dimethyl sulfoxide), EA (ethyl acetate), MeOH (methanol), TLC (thin-layer chromatography).

The following substances have been synthesised and characterised. However, the preparation and characterisation of the substances can also be carried out by other methods by the person skilled in the art.

EXAMPLE 1

Illustrative Compounds of the Formula I

TABLE 1a

| No. | Compound (structure) | Compound (chemical name) | IC50 [ADAMTS5]M | MMP1 [nM] higher than | MMP14 [nM] higher than |
|---|---|---|---|---|---|
| 1 | | 4-[(Biphenyl-4-carbonyl)-amino]-2-methyl-4-(3,4,5-trimethoxy-benzylcarbamoyl)-butyric acid | 1.30E−08 | 3.00E−05 | 3.00E−05 |
| 2 | | (2S,4S)-4-[2-(4-Fluoro-phenyl)-1,1-dimethyl-ethylcarbamoyl]-4-{[5-(4-fluoro-phenyl)-thiazole-2-carbonyl]-amino}-2-methyl-butyric acid | 4.70E−08 | 1.00E−06 | 1.00E−06 |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 3 | | (2S,4S)-4-[(Biphenyl-4-carbonyl)-amino]-4-[(S)-2-(4-fluoro-phenyl)-1-methyl-ethylcarbamoyl]-2-methyl-butyric acid | 6.20E−08 | 3.00E−05 | 3.00E−05 |
| 4 | | (2S,4S)-4-[(Biphenyl-4-carbonyl)-amino]-4-(1,1-dimethyl-2-pyridin-3-yl-ethylcarbamoyl)-2-methyl-butyric acid | 6.60E−08 | 3.00E−05 | 3.00E−05 |
| 5 | | (2S,4S)-4-[(Biphenyl-4-carbonyl)-amino]-4-[2-(4-fluoro-phenyl)-1,1-dimethyl-ethylcarbamoyl]-2-methyl-butyric acid | 8.50E−08 | 3.00E−05 | 3.00E−05 |
| 6 | | (2S,4S)-2-Benzyl-4-[(biphenyl-4-carbonyl)-amino]-4-[2-(4-fluoro-phenyl)-1,1-dimethyl-ethylcarbamoyl]-butyric acid | 1.50E−07 | 3.00E−05 | 3.00E−05 |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 7 | | (2S,4S)-2-[(Biphenyl-4-carbonyl)-amino]-2-[2-(4-fluoro-phenyl)-1,1-dimethyl-ethylcarbamoyl]-ethyl}-pentanoic acid | 1.70E−07 | 3.00E−05 | 3.00E−05 |
| 8 | | (2S,4S)-4-[(Biphenyl-4-carbonyl)-amino]-4-[2-(4-fluoro-phenyl)-1,1-dimethyl-ethylcarbamoyl]-2-methoxymethyl-butyric acid | 1.70E−07 | 3.00E−05 | 3.00E−05 |
| 9 | | (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid | 1.80E−07 | | |
| 10 | | (2S,4S)-4-[2-(4-Fluoro-phenyl)-1,1-dimethyl-ethylcarbamoyl]-2-methyl-4-(4-pyridin-2-yl-benzoylamino)-butyric acid | 1.90E−07 | 3.00E−05 | 3.00E−05 |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 11 | | (2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid | 2.50E−07 | | |
| 12 | | (2S,4S)-4-[2-(4-Fluoro-phenyl)-1,1-dimethyl-ethylcarbamoyl]-4-{[1-(4-fluoro-phenyl)-piperidine-4-carbonyl]-amino}-2-methyl-butyric acid | 3.20E−07 | 3.00E−05 | 3.00E−05 |
| 13 | | 4-[2-(4-Fluoro-phenyl)-1,1-dimethyl-ethylcarbamoyl]-2-methyl-4-[(5-phenyl-pyridine-2-carbonyl)-amino]-butyric acid | 3.30E−07 | 3.00E−05 | 3.00E−05 |
| 14 | | (2S,4S)-4-[2-(4-Fluoro-phenyl)-1,1-dimethyl-ethylcarbamoyl]-2-methyl-4-[(6-phenyl-pyridine-3-carbonyl)-amino]-butyric acid | 3.50E−07 | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 15 | | (2S,4S)-4-[2-(4-Fluoro-phenyl)-1,1-dimethyl-ethylcarbamoyl]-2-methyl-4-[(4-phenyl-piperazine-1-carbonyl)-amino]-butyric acid | 3.60E−07 | | |
| 16 | | (2S,4S)-4-[2-(4-Fluoro-phenyl)-1,1-dimethyl-ethylcarbamoyl]-2-methyl-4-(4-pyridin-3-yl-benzoylamino)-butyric acid | 3.90E−07 | | |
| 17 | | (2S,4S)-4-[(Biphenyl-4-carbonyl)-amino]-4-[2-(4-fluoro-phenyl)-1-methyl-ethylcarbamoyl]-2-methyl-butyric acid | 5.30E−07 | 3.00E−05 | 3.00E−05 |
| 18 | | (2S,4S)-4-[2-(4-Fluoro-phenyl)-1,1-dimethyl-ethylcarbamoyl]-2-methyl-4-[(4-phenyl-piperidine-1-carbonyl)-amino]-butyric acid | 1.20E−06 | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 19 | | (2S,4S)-4-[2-(4-Fluoro-phenyl)-1,1-dimethyl-ethylcarbamoyl]-2-methyl-4-[4-(5-methyl-thiazol-2-yl)-benzoylamino]-butyric acid | 1.20E−06 | 1.00E−06 | 1.00E−06 |
| 20 | | (2S,4S)-4-[2-(4-Fluoro-phenyl)-1,1-dimethyl-ethylcarbamoyl]-4-{[2-(4-fluoro-phenyl)-thiazole-5-carbonyl]-amino}-2-methyl-butyric acid | 1.40E−06 | | |
| 21 | | (2S,4S)-4-[2-(4-Fluoro-phenyl)-1,1-dimethyl-ethylcarbamoyl]-2-methyl-4-(4-pyrazol-1-yl-benzoylamino)-butyric acid | | | |
| 22 | | (2S,4S)-4-Amino-4-[2-(4-fluoro-phenyl)-1,1-dimethyl-ethylcarbamoyl]-2-methyl-butyric acid methyl ester | | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 23 | | 2S,4S)-4-[2-(4-Fluoro-phenyl)-1,1-dimethyl-ethylcarbamoyl]-2-methyl-4-[(6-phenyl-pyridine-3-carbonyl)-amino]-butyric acid methyl ester | | | |
| 24 | | (2S,4S)-4-[2-(4-Fluoro-phenyl)-1,1-dimethyl-ethylcarbamoyl]-2-methyl-4-(4-pyridin-3-yl-benzoylamino)-butyric acid methyl ester | | | |
| 25 | | 2S,4S)-4-[2-(4-Fluoro-phenyl)-1,1-dimethyl-ethylcarbamoyl]-2-methyl-4-(4-pyridin-2-yl-benzoylamino)-butyric acid methyl ester | | | |
| 26 | | (2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid methyl ester | | | |

TABLE 1a-continued

| No. | Compound (structure) | Compound (chemical name) | IC50 [ADAM-NTS5]M | MMP1 [nM] higher than | MMP14 [nM] higher than |
|-----|----------------------|--------------------------|-------------------|----------------------|------------------------|
| 27  | | (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid methyl ester | | | |
| 28  | | (2S,4S)-4-[2-(4-Fluoro-phenyl)-1,1-dimethyl-ethylcarbamoyl]-4-{[5-(4-fluoro-phenyl)-thiazole-2-carbonyl]-amino}-2-methyl-butyric acid methyl ester | | | |
| 29  | | (2S,4S)-4-[2-(4-Fluoro-phenyl)-1,1-dimethyl-ethylcarbamoyl]-4-{[2-(4-fluoro-phenyl)-thiazole-5-carbonyl]-amino}-2-methyl-butyric acid methyl ester | | | |
| 30  | | (2S,4S)-4-[2-(4-Fluoro-phenyl)-1,1-dimethyl-ethylcarbamoyl]-2-methyl-4-[4-(5-methyl-thiazol-2-yl)-benzoylamino]-butyric acid methyl ester | | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 31 | | (2S,4S)-4-[2-(4-Fluoro-phenyl)-1,1-dimethyl-ethylcarbamoyl]-4-{[1-(4-fluoro-phenyl)-piperidine-4-carbonyl]-amino}-2-methyl-butyric acid methyl ester | | | |
| 32 | | (2S,4S)-4-[2-(4-Fluoro-phenyl)-1,1-dimethyl-ethylcarbamoyl]-2-methyl-4-(4-pyrazol-1-yl-benzoylamino)-butyric acid methyl ester | | | |
| 33 | | (2S,4S)-4-[2-(4-Fluoro-phenyl)-1,1-dimethyl-ethylcarbamoyl]-2-methyl-4-[(4-phenyl-piperidine-1-carbonyl)-amino]-butyric acid methyl ester | | | |
| 34 | | 2S,4S)-4-[2-(4-Fluoro-phenyl)-1,1-dimethyl-ethylcarbamoyl]-2-methyl-4-[(4-phenyl-piperazine-1-carbonyl)-amino]-butyric acid methyl ester | | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 35 | | (2S,4S)-4-[(Biphenyl-4-carbonyl)-amino]-2-methyl-4-(3,4,5-trimethoxy-benzylcarbamoyl)-butyric acid methyl ester | | | |
| 36 | | (2S,4S)-4-[(Biphenyl-4-carbonyl)-amino]-4-[2-(4-fluoro-phenyl)-1-methyl-ethylcarbamoyl]-2-methyl-butyric acid methyl ester | | | |
| 37 | | (2S,4S)-4-[(Biphenyl-4-carbonyl)-amino]-4-(1,1-dimethyl-2-pyridin-3-yl-ethylcarbamoyl)-2-methyl-butyric acid methyl ester | | | |
| 38 | | (2S,4S)-4-[2-(4-Fluoro-phenyl)-1,1-dimethyl-ethylcarbamoyl]-2-methyl-4-(4-pyrazin-2-yl-benzoylamino)-butyric acid | | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 39 | | (2S,4S)-4-[(Biphenyl-4-carbonyl)-amino]-2-methyl-4-(1,1,3-trimethyl-butylcarbamoyl)-butyric acid | | | |
| 40 | | (2S,4S)-4-[2-(4-Fluoro-phenyl)-1,1-dimethyl-ethylcarbamoyl]-2-methyl-4-[(5-phenyl-pyrazine-2-carbonyl)-amino]-butyric acid | | | |
| 41 | | (2S,4S)-4-[2-(4-Fluoro-phenyl)-1,1-dimethyl-ethylcarbamoyl]-2-methyl-4-(4-pyrazol-1-yl-benzoylamino)-butyric acid | | | |
| 42 | | (2S,4S)-4-[4-(1-Difluoromethyl-1H-pyrazol-4-yl)-benzoylamino]-4-[2-(4-fluoro-phenyl)-1,1-dimethyl-ethylcarbamoyl]-2-methyl-butyric acid | | | |

TABLE 1a-continued

| No. | Compound (structure) | Compound (chemical name) | IC50 [ADAM-NTS5]M | MMP1 [nM] higher than | MMP14 [nM] higher than |
|---|---|---|---|---|---|
| 43 | | (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid | | | |
| 44 | | (S)-4-[(Biphenyl-4-carbonyl)-amino]-4-[2-(4-fluoro-phenyl)-1,1-dimethyl-ethylcarbamoyl]-2,2-dimethyl-butyric acid | | | |
| 45 | | (2S,4S)-4-[(Biphenyl-4-carbonyl)-amino]-4-[3-(4-fluoro-benzyl)-oxetan-3-ylcarbamoyl]-2-methyl-butyric acid | | | |
| 46 | | (2S,4S)-4-[(Biphenyl-4-carbonyl)-amino]-4-(1,1-dimethyl-propylcarbamoyl)-2-methyl-butyric acid | | | |

In order to avoid any doubt, in all cases where the chemical name of a compound according to the invention and the depiction of the chemical structure of the compound mistakenly do not agree, the compound according to the invention is defined unambiguously by the depiction of the chemical structure.

TABLE 1b

| No. of compound of table 1a | MW | Microsomes human | Fraction unbound human | GAG-Assay | Solubility pH7.4 [mg/ml] | Mass (M + H) | Ret. Time [Min] |
|---|---|---|---|---|---|---|---|
| 1 | 520.574 | 0.85 | 10 | | 0.85 | 521.3 | 4.1 |
| 2 | 515.572 | 0.912 | 17 | | 0.912 | 516.3 | 5.19 |
| 3 | 476.539 | 0.159 | 18 | | 0.159 | | |
| 4 | 473.563 | | 10 | | | 474.2 | 3.48 |
| 5 | 490.566 | 0.677 | 39 | 1.80E−06 | 0.677 | 491.2 | 3.59 |
| 6 | 566.662 | 0.06 | 92 | | 0.06 | 567.2 | 2.27 |
| 7 | 518.619 | 0.157 | 67 | 1.00E−06 | 0.157 | 519.2 | 3.76 |
| 8 | 520.592 | 0.838 | 40 | 1.20E−06 | 0.838 | 521.2 | 3.57 |
| 9 | 494.558 | 0.798 | 10 | | 0.798 | 495.2 | 4.15 |
| 10 | 491.554 | 0.883 | 10 | | 0.883 | 492.3 | 4.34 |
| 11 | 508.556 | 0.648 | 31 | | 0.648 | 509.3 | 5.27 |
| 12 | 515.592 | 0.743 | 10 | | 0.743 | 516.3 | 3.61 |
| 13 | 491.554 | 0.855 | 10 | | 0.855 | 492.3 | 5.01 |
| 14 | 491.554 | 0.775 | 10 | | 0.775 | 490.3 | 4.73 |
| 15 | 498.59 | 0.924 | 10 | | 0.924 | 499.2 | 3.93 |
| 16 | 491.554 | 0.365 | 10 | | 0.365 | 490.3 | 4.34 |
| 17 | 476.539 | 0.303 | 21 | | 0.303 | | |
| 18 | 497.602 | 0.805 | 19 | | 0.805 | 498.3 | 4.91 |
| 19 | 511.608 | 0.637 | 10 | | 0.637 | 512.2 | 4.64 |
| 20 | 515.572 | 0.493 | 13 | | 0.493 | 516.3 | 5.19 |

EXAMPLE 2

Preparation of the Compounds According to the Invention

The claimed compounds are synthetically accessible by following synthesis sequences for those skilled in the art. The examples describe the synthesis, but do not limit it to the examples shown.

Synthetic Sequence:

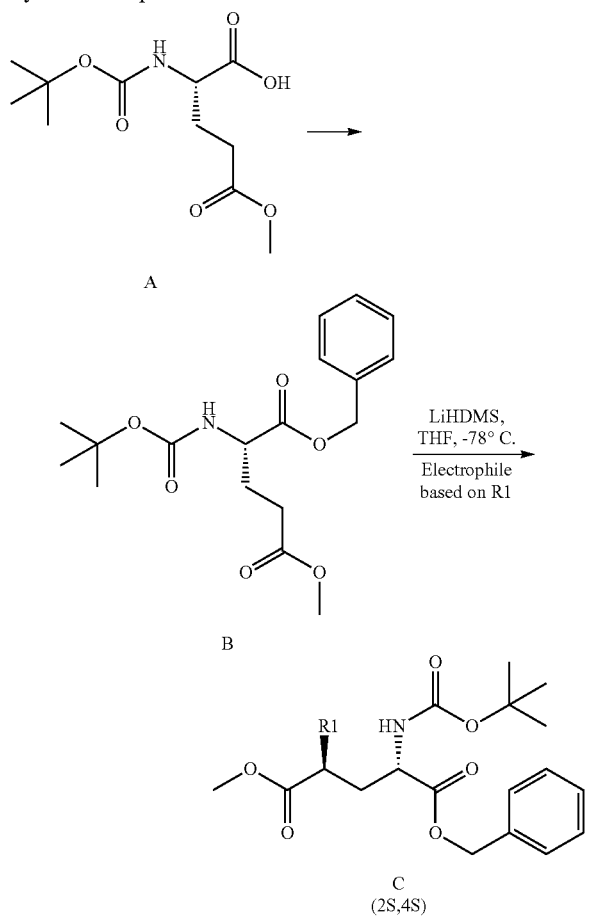

Based on glutamate derivative B, that is easily synthesized from commercially available building block A, deprotonation at low temperatures using strong bases like LiHDMS, followed by diastereoselective alkylation leads to intermediate C. Applying this method various reactive alkylation agents may be employed like alkyl-, allyl- or benzyl-halides (in particular iodides) or epoxides or other activated alkylation agents. These alkylation agents could also carry additional functional groups preferably in a protected form.

By a second deprotonation-alkylation sequence also dialkylated compounds like C1 are accessible:

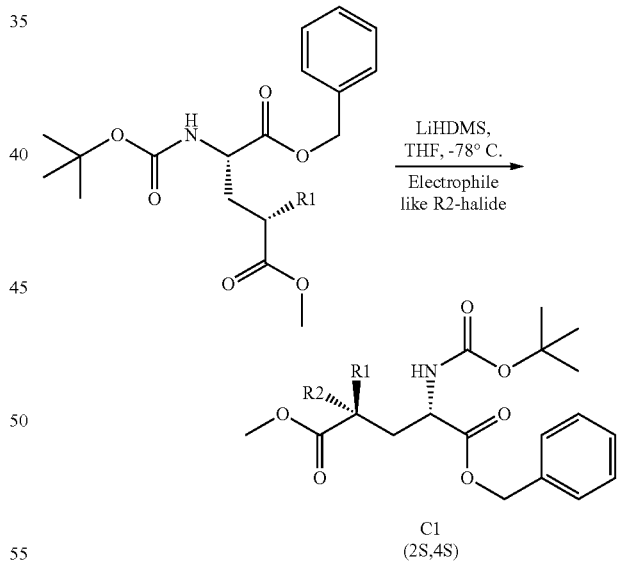

The following intermediates may be produced using this sequence without limiting it to the examples shown:

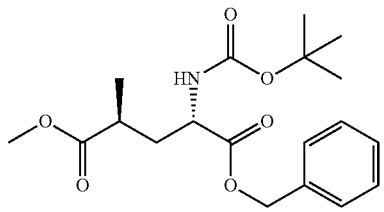

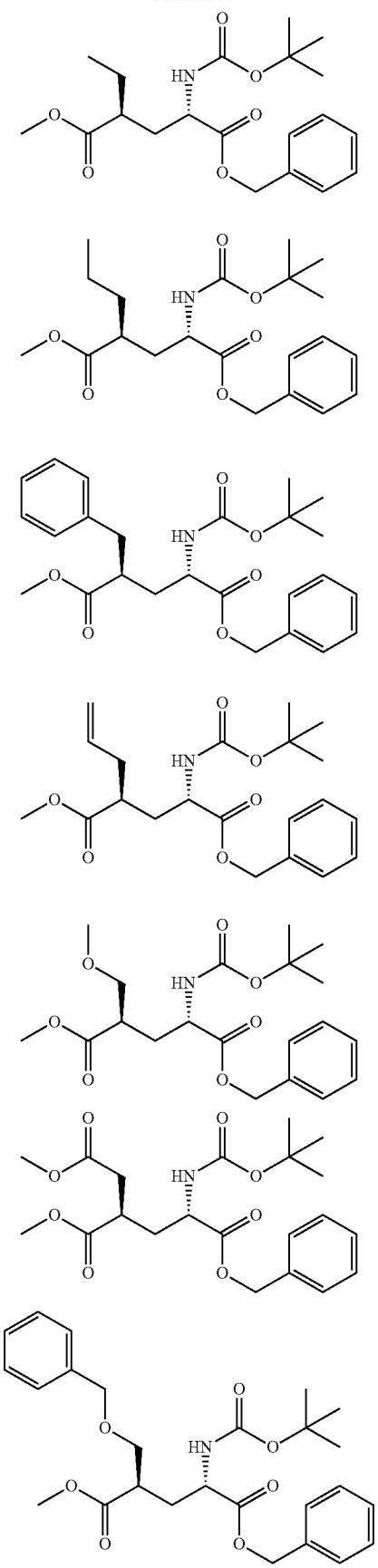
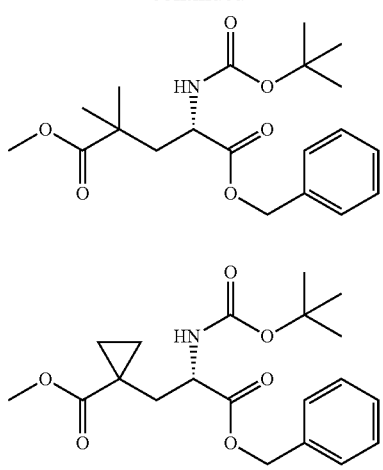
Access to compounds of formula I with D=-E-G-K or L and E being an aromatic, heteroaromatic, cycloaliphatic or cycloheteroaliphatic moiety is achieved by the following sequence:
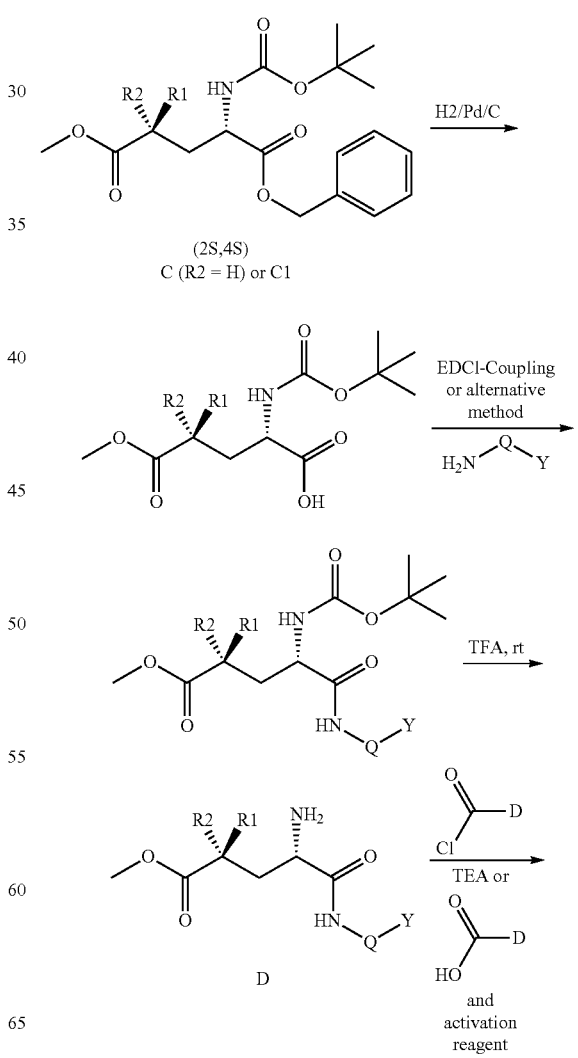

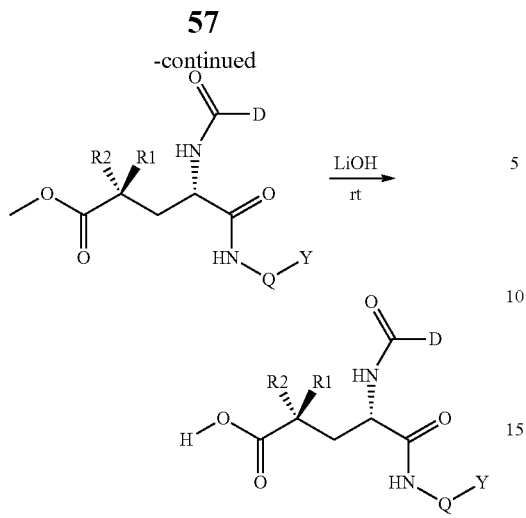

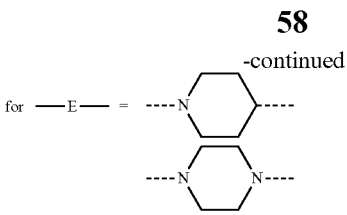

Hydrogenolytic cleavage of the benzylic ester, amide formation using standard coupling methods known to those skilled in the art (e.g. EDCl-coupling, or usage of isobutyl-chloroformate and NMM), BOC cleavage by under acidic conditions (e.g. TFA in DCM, or HCl in dioxane) provides intermediate D. Amide formation using acid chlorides D-COCl or applying other coupling methods using the corresponding acid and n activation reagent (e.g. T3P), followed by methyl ester cleavage under mild conditions (LiOH in water, methanol, THF or similar solvents or appropriate mixtures) in order to prevent racemisation leads to compounds of formula.

In case acids chlorides D-COCl required are required, they can be prepared from the corresponding acids which are either commercially available or are produced by various methods as shown in the examples. The same is true for the required amine building blocks $NH_2$-Q-Y.

Access to compounds of formula I with D=-E-G-K or L and E being a N-piperidinyl or a N-piperazinyl moiety is achieved by the following sequence:

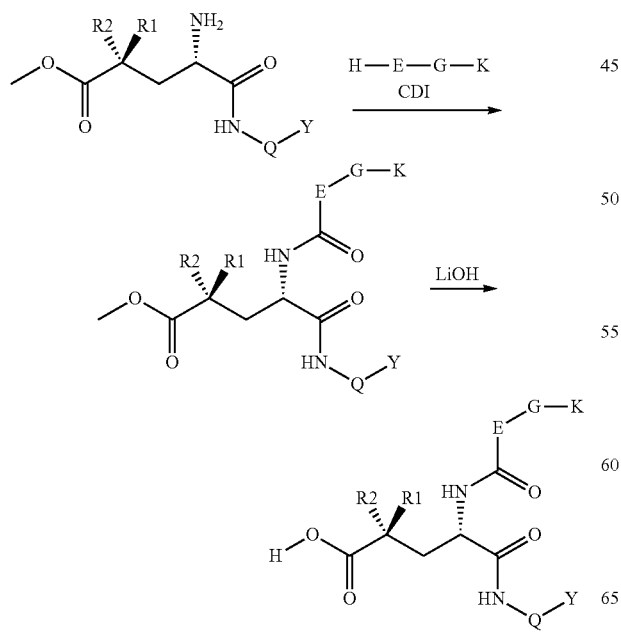

EXAMPLE 3

4-[2-(4-Fluoro-phenyl)-1,1-dimethyl-ethylcarbamoyl]-2-methyl-4-[(5-phenyl-pyridine-2-carbonyl)-amino]-butyric acid (table 1a, compound 13)

Step 1: (S)-2-tert-Butoxycarbonylamino-pentanedioic acid 1-benzyl ester 5-methyl ester

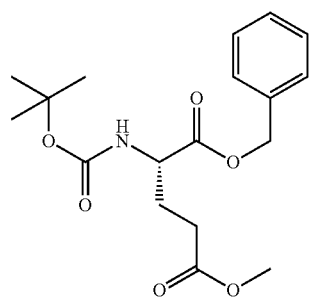 [SMILES: COC(=O)CC[C@H](NC(=O)OC(C)(C)C)C(=O)OCc1ccccc1]

(S)-2-tert-Butoxycarbonylamino-pentanedioic acid 1-benzyl ester (10 g, 29.63 mmol) was taken in anhydrous DMF (100 mL) along with dry potassium carbonate (6.13 g, 44.45 mmol) and cooled to 0° C. To this was added methyl iodide (2.02 mL, 32.60 mmol) dropwise and stirred for 3 h to get the reaction completed. Contents of the flask were filtered through a celite pad and concentrated to get a crude product which was purified by column chromatography (pet ether/ethyl acetate 25%) to get the titled product as an off white solid.

Yield: 9.5 g, (91%, off white solid).

LCMS: (Method C) 252.0 (M-BOC), Rt. 4.94 min, 98.2% (ADC1 A).

Step 2: (2S,4S)-2-tert-Butoxycarbonylamino-4-methyl-pentanedioic acid 1-benzyl ester 5-methyl ester

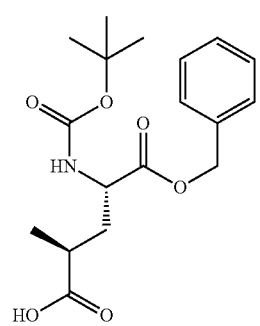 [SMILES: C[C@@H](C[C@H](NC(=O)OC(C)(C)C)C(=O)OCc1ccccc1)C(=O)O]

(S)-2-tert-Butoxycarbonylamino-pentanedioic acid 1-benzyl ester 5-methyl ester (5 g, 14.24 mmol) in dry THF (10 mL) was added to a stirring solution of Lithium bis(trimethylsilyl)amide (1M solution in THF) (29.9 mL, 29.9 mmol) at −78° C. and stirred for 1 h at the same temperature. Methyl iodide (2.64 mL, 42.72 mmol) was added drop wise in to the reaction mass and stirred for 1 h at −78° C. to get the reaction completed. Contents of the flask were quenched with a saturated solution of ammonium chloride and extracted with ethyl acetate, washed with water and brine respectively, dried over anhydrous sodium sulphate and concentrated to get the crude product which was purified by column chromatography (pet ether/ethyl acetate 15%).

Yield: 3.8 g, (73%, off white solid).
LCMS: (Method A) 266.0 (M-BOC), Rt. 5.13 min, 90.5% (max), 88.86% (220 nm).

Step 3: (2S,4S)-2-tert-Butoxycarbonylamino-4-methyl-pentanedioic acid 5-methyl ester

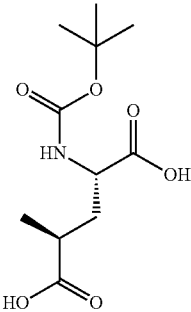 [SMILES: C[C@@H](C[C@H](NC(=O)OC(C)(C)C)C(=O)O)C(=O)O]

(2S,4S)-2-tert-Butoxycarbonylamino-4-methyl-pentanedioic acid 1-benzyl ester 5-methyl ester (2.5 g, 6.84 mmol) was taken in dry methanol (50 mL) and 10% Palladium on carbon (250 mg) was added to it and stirred under a hydrogen bladder for 1 h to get the reaction completed. Reaction mass was filtered through celite and concentrated to get the product as a colorless oil.

Yield: 1.6 g, (85%, colorless oil).
LCMS: (Method C) 176.0 (M-BOC), Rt. 3.33 min, 98.5% (ADC1 A).

Step 4: (2S,4S)-4-tert-Butoxycarbonylamino-4-[2-(4-fluoro-phenyl)-1,1-dimethyl-ethylcarbamoyl]-2-methyl-butyric acid methyl ester

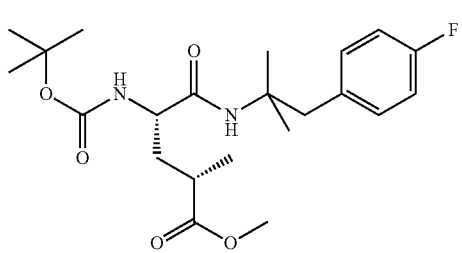 [SMILES: COC(=O)[C@@H](C)C[C@H](NC(=O)OC(C)(C)C)C(=O)NC(C)(C)Cc1ccc(F)cc1]

(2S,4S)-2-tert-Butoxycarbonylamino-4-methyl-pentanedioic acid 5-methyl ester (2 g, 7.26 mmol) and N-methyl morpholine (1 g, 10.89 mmol) were taken in toluene (25 mL) and 2-(4-fluorophenyl)1,1-dimethylethylamine (1.33 g, 7.90 mmol) and isobutylchloroformate (1.2 mL, 8.74 mmol) were added to it. Reaction mass was stirred at RT for 1 h to get the reaction completed. Reaction mass was quenched with water and the organic layer was separated and dried over anhydrous sodium sulphate, concentrated to get the crude product which was purified by column chromatography (pet ether/ethyl acetate 25%).

Yield: 2.75 g, (92%, colorless gum).
LCMS: (Method C) 425.2 (M+1), Rt. 5.35 min, 99.5% (ADC1 A).

Step 5: (2S,4S)-4-Amino-4-[2-(4-fluoro-phenyl)-1,1-dimethyl-ethylcarbamoyl]-2-methyl-butyric acid methyl ester TFA salt

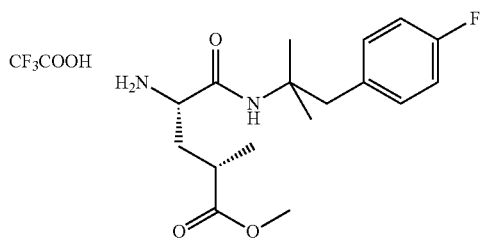 [SMILES: "CF3COOH" ; COC(=O)[C@@H](C)C[C@H](N)C(=O)NC(C)(C)Cc1ccc(F)cc1]

(2S,4S)-4-tert-Butoxycarbonylamino-4-[2-(4-fluoro-phenyl)-1,1-dimethyl-ethylcarbamoyl]-2-methyl-butyric acid methyl ester (2.75 g, 6.48 mmol) was taken dry DCM (20 mL) and trifluoroacetic acid (2 mL) was added drop wise in to it and stirred for 5 h to get the reaction completed. Reaction mass was concentrated and azeotroped with toluene twice to get the titled salt as a colorless oil.

Yield: 2 g, (72%, colorless oil).
LCMS: (Method C) 325.2 (M+1), Rt. 3.48 min, 98.7% (ADC1 A), 81.8 (220 nm).

Step 6: (2S,4S)-4-[2-(4-Fluoro-phenyl)-1,1-dimethyl-ethylcarbamoyl]-2-methyl-4-[(5-phenyl-pyridine-2-carbonyl)-amino]-butyric acid methyl ester

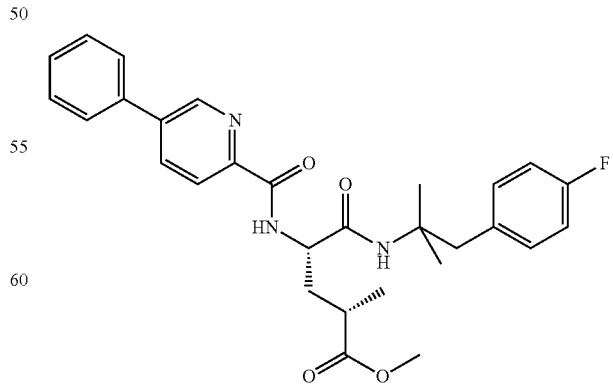

(2S,4S)-4-Amino-4-[2-(4-fluoro-phenyl)-1,1-dimethyl-ethylcarbamoyl]-2-methyl-butyric acid methyl ester TFA salt (0.43 g, 1 mmol) and 5-phenylpyridine-2-carboxylic acid (0.2 g, 1 mmol) were taken in dry DCM (10 mL) and triethylamine (0.42 mL, 3 mmol) was added to it. The contents of the flask were cooled to 0° C. and 50% solution of T3P in ethyl acetate (0.63 g, 2 mmol) were added drop wise in to it and stirred for 2 h to get the reaction completed. Reaction mass was washed with water, brine. Organic phase was dried over anhydrous sodium sulphate, concentrated to get the crude product which was purified by column chromatography (pet ether/ethyl acetate 15%) to get the titled product as an off white solid.

Yield: 0.2 g, (40%, off white solid.).

LCMS: (Method A) 506.2 (M+1), Rt. 5.75 min, 91.32% (max).

Step 7: (2S,4S)-4-[2-(4-Fluoro-phenyl)-1,1-dimethyl-ethylcarbamoyl]-2-methyl-4-[(5-phenyl-pyridine-2-carbonyl)-amino]-butyric acid

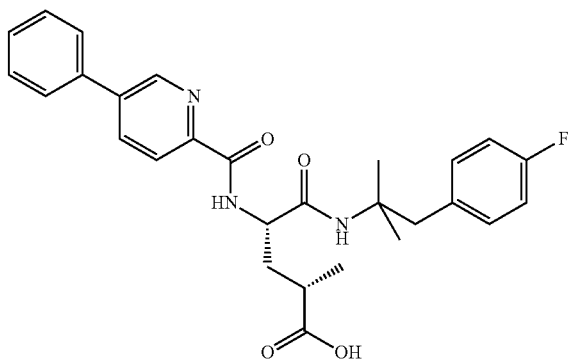 [SMILES: C[C@@H](C[C@H](NC(=O)c1ccc(-c2ccccc2)cn1)C(=O)NC(C)(C)Cc1ccc(F)cc1)C(=O)O]

(2S,4S)-4-[2-(4-Fluoro-phenyl)-1,1-dimethyl-ethylcarbamoyl]-2-methyl-4-[(5-phenyl-pyridine-2-carbonyl)-amino]-butyric acid methyl ester (0.2 g, 0.39 mmol) was taken in a mixture of solvents THF (3 mL), methanol (1 mL) and water (1 mL) and lithium hydroxide monohydrate (33 mg, 0.78 mmol) was added to it and stirred for 2 h to get the reaction completed. Contents of the flask were concentrated and the crude mass was quenched with dilute aqueous solution of HCl. The solid obtained was filtered and washed with water, suck dried to obtain the titled compound as an off white solid.

Yield: 0.17 g, (89%, off white solid.).

$^1$H NMR: 400 MHz, DMSO-d6: δ 12.12 (s, 1H), 9.00 (d, J=1.72 Hz, 1H), 8.65 (d, J=9.28 Hz, 1H), 8.30-8.32 (m, 1H), 8.13-8.15 (m, 1H), 7.81-7.83 (m, 2H), 7.68 (s, 1H), 7.53-7.57 (m, 2H), 7.46-7.50 (m, 1H), 7.07-7.11 (m, 2H), 6.92 (t, J=8.80 Hz, 2H), 4.55-4.61 (m, 1H), 3.01 (d, J=13.00 Hz, 1H), 2.91 (d, J=13.08 Hz, 1H), 2.27-2.32 (m, 1H), 2.04-2.09 (m, 1H), 1.63-1.69 (m, 1H), 1.23 (s, 3H), 1.18 (s, 3H), 1.10 (d, J=6.92 Hz, 3H).

LCMS: (Method B) 492.3 (M+1), Rt. 5.01 min, 95.1% (max), 94.3% (254 nm).

HPLC: (Method A) Rt. 4.96 min, 95.8% (max), 96.6% (254 nm).

Chiral purity: 95.75%

EXAMPLE 4

(2S,4S)-4-[2-(4-Fluoro-phenyl)-1,1-dimethyl-ethylcarbamoyl]-2-methyl-4-[(6-phenyl-pyridine-3-carbonyl)-amino]-butyric acid (table 1a, compound 14)

Step 1: (2S,4S)-4-[2-(4-Fluoro-phenyl)-1,1-dimethyl-ethylcarbamoyl]-2-methyl-4-[(6-phenyl-pyridine-3-carbonyl)-amino]-butyric acid methyl ester

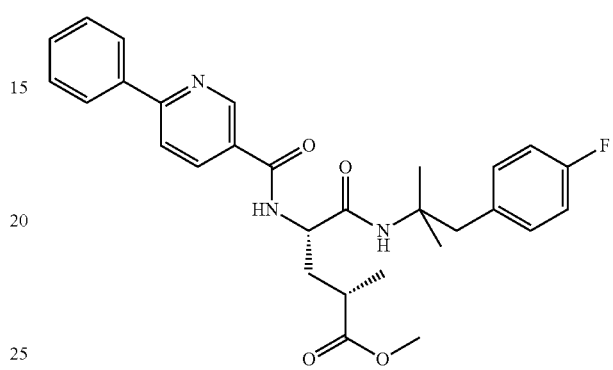

Synthesized using the protocol similar to example 1 step 6 using 6-phenylnicotinic acid (80 mg, 0.4 mmol) and (2S,4S)-4-Amino-4-[2-(4-fluoro-phenyl)-1,1-dimethyl-ethylcarbamoyl]-2-methyl-butyric acid methyl ester TFA salt (0.18 g, 0.4 mmol) to give the titled compound as an off white solid.

Yield: 0.12 g, (60%, off white solid.).

LCMS: (Method A) 506.2 (M+1), Rt. 4.87 min, 97.9% (max), 97.7% (254 nm).

Step 2: (2S,4S)-4-[2-(4-Fluoro-phenyl)-1,1-dimethyl-ethylcarbamoyl]-2-methyl-4-[(6-phenyl-pyridine-3-carbonyl)-amino]-butyric acid

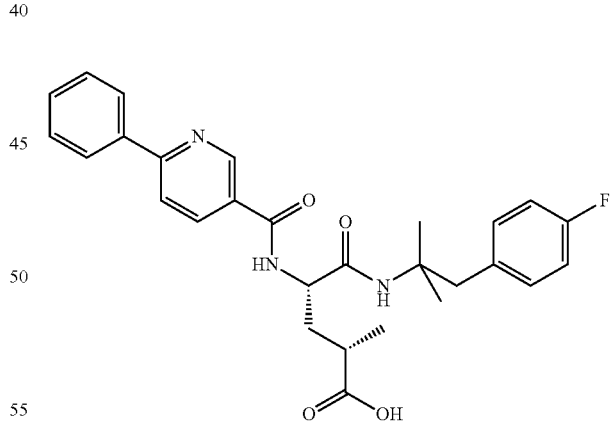

Synthesized using the protocol similar to example 1 step 7 using 4-[2-(4-Fluoro-phenyl)-1,1-dimethyl-ethylcarbamoyl]-2-methyl-4-[(6-phenyl-pyridine-3-carbonyl)-amino]-butyric acid methyl ester (0.1 g, 0.19 mmol) to get the titled compound as an off white solid.

Yield: 30 mg, (31%, off white solid.).

$^1$H NMR: 400 MHz, DMSO-d6: δ 12.21 (s, 1H), 9.11 (d, J=2.20 Hz, 1H), 8.66 (d, J=8.20 Hz, 1H), 8.31-8.34 (m, 1H), 8.15-8.17 (m, 2H), 8.10 (d, J=8.36 Hz, 1H), 7.46-7.55 (m, 3H), 7.40 (s, 1H), 7.10-7.14 (m, 2H), 6.96 (t, J=8.84 Hz, 2H), 4.49-4.55 (m, 1H), 3.05 (d, J=13.12 Hz, 1H), 2.88 (d,

J=12.56 Hz, 1H), 2.06-2.40 (m, 2H), 1.65-1.72 (m, 1H), 1.23 (s, 3H), 1.16 (s, 3H), 1.08 (d, J=7.04 Hz, 3H).

LCMS: (Method B) 490.3 (M−1), Rt. 4.73 min, 95.2% (max), 95.2% (254 nm).

HPLC: (Method A) Rt. 4.52 min, 96.1% (max), 95.6% (254 nm).

Chiral purity: 100%

EXAMPLE 5

(2S,4S)-4-[2-(4-Fluoro-phenyl)-1,1-dimethyl-ethyl-carbamoyl]-2-methyl-4-(4-pyridin-3-yl-benzoy-lamino)-butyric acid (table 1a, compound 16)

Step 1: (2S,4S)-4-[2-(4-Fluoro-phenyl)-1,1-dimethyl-ethylcarbamoyl]-2-methyl-4-(4-pyridin-3-yl-benzoylamino)-butyric acid methyl ester

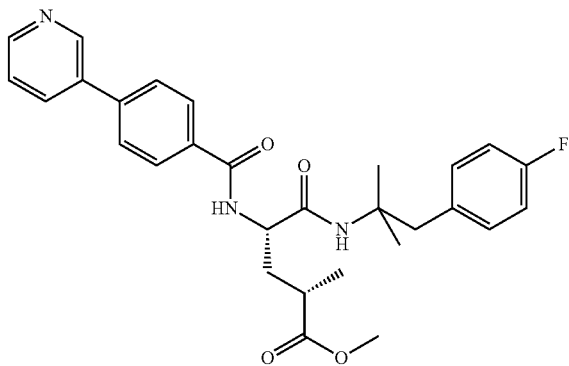 [SMILES: COC(=O)[C@@H](C)C[C@H](NC(=O)c1ccc(-c2cccnc2)cc1)C(=O)NC(C)(C)Cc1ccc(F)cc1]

Synthesised using the protocol similar to example 1 step 6 using 4-pyridin-3-ylbenzoic acid (120 mg, 0.6 mmol) and (2S,4S)-4-Amino-4-[2-(4-fluoro-phenyl)-1,1-dimethyl-ethylcarbamoyl]-2-methyl-butyric acid methyl ester TFA salt (0.26 g, 0.6 mmol) to give the titled compound as an off white solid. Yield: 130 mg, (39%, off white solid.).

LCMS: (Method A) 506.2 (M+1), Rt. 3.89 min, 99.3% (max), 98.2% (254 nm).

Step 2: (2S,4S)-4-[2-(4-Fluoro-phenyl)-1,1-dimethyl-ethylcarbamoyl]-2-methyl-4-(4-pyridin-3-yl-benzoylamino)-butyric acid

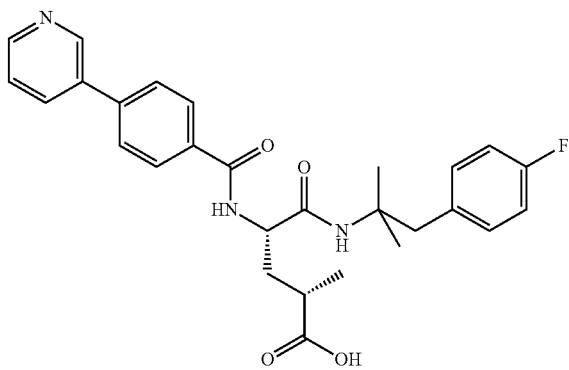 [SMILES: C[C@@H](C[C@H](NC(=O)c1ccc(-c2cccnc2)cc1)C(=O)NC(C)(C)Cc1ccc(F)cc1)C(=O)O]

Synthesized using the protocol similar to example 1 step 7 using (2S,4S)-4-[2-(4-Fluoro-phenyl)-1,1-dimethyl-ethyl-carbamoyl]-2-methyl-4-(4-pyridin-3-yl-benzoylamino)-butyric acid methyl ester (0.1 g, 0.19 mmol) to get the titled compound as an off white solid.

Yield: 40 mg, (46%, off white solid.).

$^1$H NMR: 400 MHz, DMSO-d6: δ 12.15 (s, 1H), 8.97 (s, 1H), 8.61 (d, J=4.68 Hz, 1H), 8.48 (d, J=8.64 Hz, 1H), 8.16 (d, J=9.24 Hz, 1H), 8.02 (d, J=8.08 Hz, 2H), 7.86 (d, J=7.84 Hz, 2H), 7.51-7.54 (m, 1H), 7.36 (s, 1H), 7.10-7.13 (m, 2H), 6.93-6.97 (m, 2H), 4.48-4.54 (m, 1H), 3.05 (d, J=12.92 Hz, 1H), 2.88 (d, J=13.04 Hz, 1H), 2.41-2.43 (m, 1H), 2.07-2.15 (m, 1H), 1.65-1.72 (m, 1H), 1.23 (s, 3H), 1.16 (s, 3H), 1.08 (d, J=6.92 Hz, 3H),.

LCMS: (Method B) 490.3 (M−1), Rt. 4.34 min, 99.7% (max), 99.3% (254 nm).

HPLC: (Method A) Rt. 3.49 min, 99.3% (max), 98.6% (254 nm).

Chiral purity: 100%

Applying the procedure described in example 3, step 6 using appropriate acids as coupling partners, the following esters have been prepared:

EXAMPLE 6

(2S,4S)-4-[2-(4-Fluoro-phenyl)-1,1-dimethyl-ethyl-carbamoyl]-2-methyl-4-(4-pyridin-2-yl-benzoy-lamino)-butyric acid methyl ester

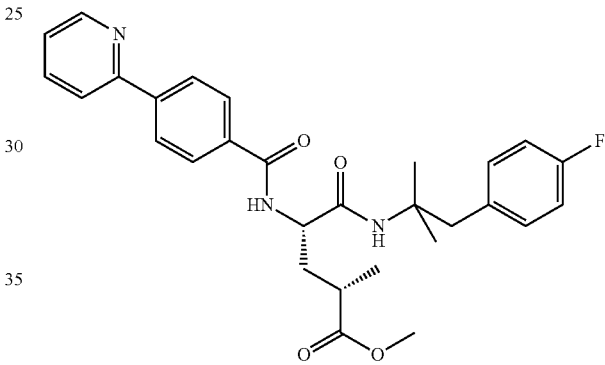

LCMS: (Method A) (M+1), 506.2, Rt. 3.94 min, 86.6% (max).

EXAMPLE 7

(2S,4S)-4-[(3-Fluoro-biphenyl-4-carbonyl)-amino]-4-[2-(4-fluoro-phenyl)-1,1-dimethyl-ethylcarbam-oyl]-2-methyl-butyric acid methyl ester

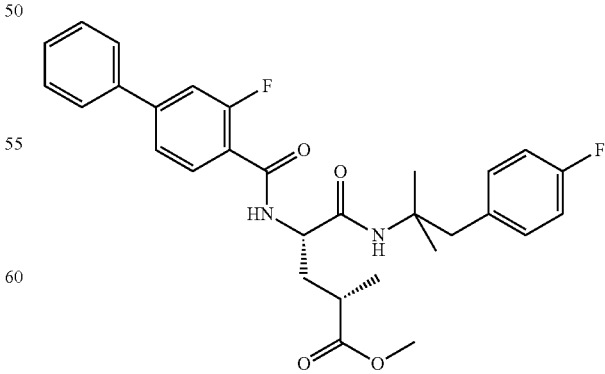

LCMS: (Method A) 523.3 (M+1), Rt. 5.82 min, 99.3% (max), 99.1% (254 nm).

EXAMPLE 8

(2S,4S)-4-[2-(4-Fluoro-phenyl)-1,1-dimethyl-ethyl-carbamoyl]-2-methyl-4-[4-(1-methyl-1H-pyrazol-3-yl)-benzoylamino]-butyric acid methyl ester

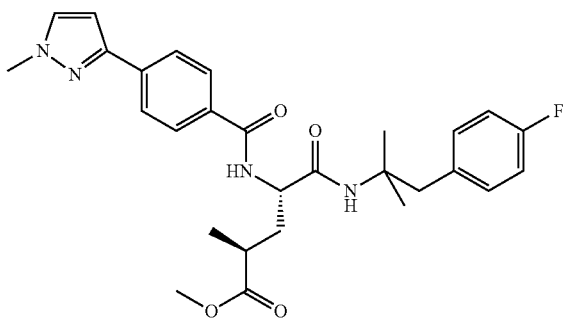 [SMILES: COC(=O)[C@@H](C)C[C@H](NC(=O)c1ccc(-c2ccn(C)n2)cc1)C(=O)NC(C)(C)Cc1ccc(F)cc1]

LCMS: (Method A) 509.2 (M+1), Rt. 4.64 min, 95.6% (max).

EXAMPLE 9

(2S,4S)-4-[2-(4-Fluoro-phenyl)-1,1-dimethyl-ethyl-carbamoyl]-4-{[5-(4-fluoro-phenyl)-thiazole-2-carbonyl]-amino}-2-methyl-butyric acid methyl ester

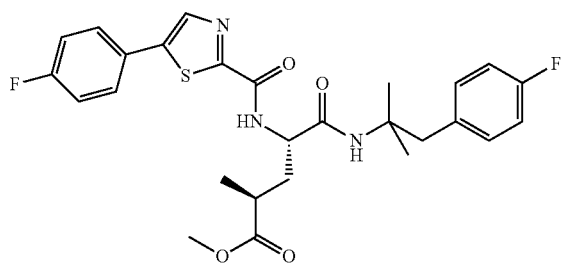 [SMILES: COC(=O)[C@@H](C)C[C@H](NC(=O)c1ncc(-c2ccc(F)cc2)s1)C(=O)NC(C)(C)Cc1ccc(F)cc1]

LCMS: (Method A) 530.2 (M+1), Rt. 5.70 min, 94.4% (max), 90.7% (220 nm).

EXAMPLE 10

(2S,4S)-4-[2-(4-Fluoro-phenyl)-1,1-dimethyl-ethyl-carbamoyl]-4-{[2-(4-fluoro-phenyl)-thiazole-5-carbonyl]-amino}-2-methyl-butyric acid methyl ester

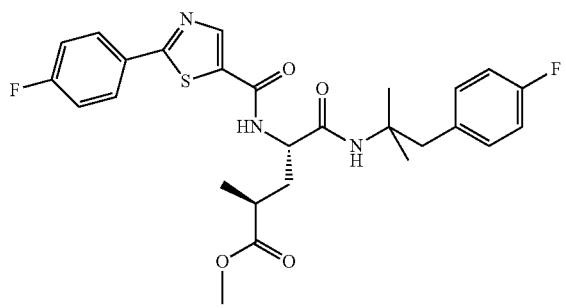 [SMILES: COC(=O)[C@@H](C)C[C@H](NC(=O)c1cnc(-c2ccc(F)cc2)s1)C(=O)NC(C)(C)Cc1ccc(F)cc1]

LCMS: (Method A) 530.2, (M+1), Rt. 5.39 min, 98.9% (max), 99.1% (220 nm).

EXAMPLE 11

(2S,4S)-4-[2-(4-Fluoro-phenyl)-1,1-dimethyl-ethyl-carbamoyl]-2-methyl-4-[4-(5-methyl-thiazol-2-yl)-benzoylamino]-butyric acid methyl ester

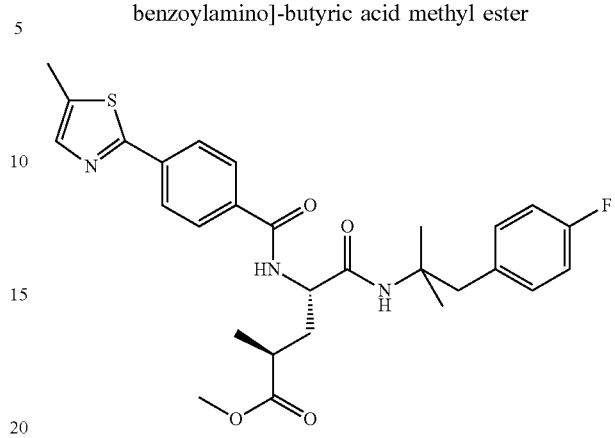

LCMS: (Method A) 526.2, (M+1), Rt. 5.15 min, 94.4% (max), 84.0% (254 nm).

EXAMPLE 12

(2S,4S)-4-[2-(4-Fluoro-phenyl)-1,1-dimethyl-ethyl-carbamoyl]-4-{[1-(4-fluoro-phenyl)-piperidine-4-carbonyl]-amino}-2-methyl-butyric acid methyl ester

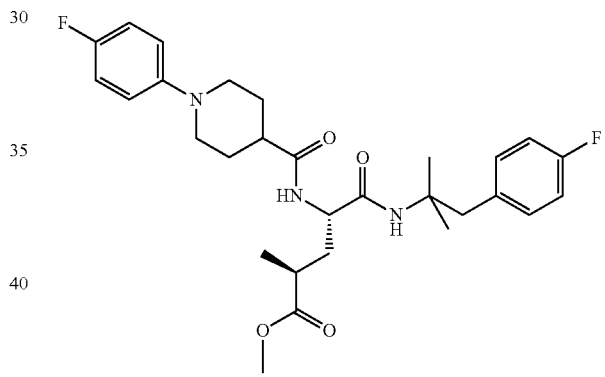

LCMS: (Method A) 530.2, (M+1), Rt. 4.03 min, 98.1% (max), 98.6% (220 nm).

EXAMPLE 13

(2S,4S)-4-[2-(4-Fluoro-phenyl)-1,1-dimethyl-ethyl-carbamoyl]-2-methyl-4-(4-pyrazol-1-yl-benzoylamino)-butyric acid methyl ester

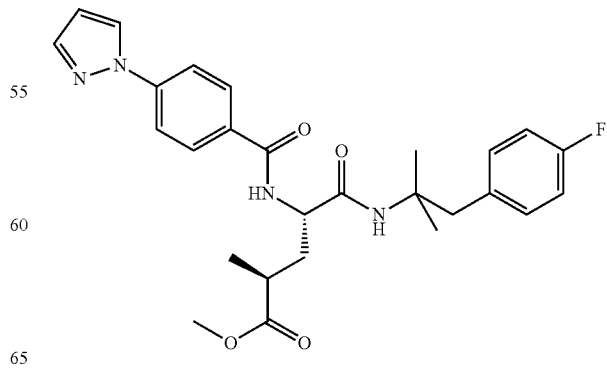

LCMS: (Method A) 495.2, (M+1), Rt. 4.90 min, 95.2% (max), 93.0% (220 nm).

EXAMPLE 14

(2S,4S)-4-[2-(4-Fluoro-phenyl)-1,1-dimethyl-ethyl-carbamoyl]-2-methyl-4-[(4-phenyl-piperidine-1-carbonyl)-amino]-butyric acid methyl ester

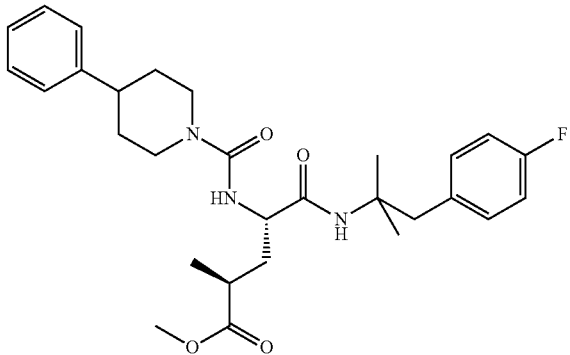 [SMILES: COC(=O)[C@@H](C)C[C@H](NC(=O)N1CCC(c2ccccc2)CC1)C(=O)NC(C)(C)Cc1ccc(F)cc1]

(2S,4S)-4-Amino-4-[2-(4-fluoro-phenyl)-1,1-dimethyl-ethylcarbamoyl]-2-methyl-butyric acid methyl ester TFA salt (200 mg, 0.89 mmol) and DIPEA (175 mg, 1.35 mmol) were taken in acetonitrile (10 mL) and cooled to 0° C. Disuccinimidylcarbonate (138 mg, 0.54 mmol) was added in to it and reaction mass was stirred for 1 h at RT. 4-phenyl piperidine (87 mg, 0.54 and 1,8-Diazabicycloundec-7-ene (82 mg, 0.54 mmol) were added to the reaction mass at 0° C. and stirred for 16 h at RT to get the reaction completed.

Reaction mass was quenched with an aqueous solution of sodium bicarbonate and extracted with ethyl acetate, dried over anhydrous sodium sulphate and concentrated to get the crude product which was purified by column chromatography to get the titled compound as a colorless oil.

Yield: 130 mg, (56%, colorless oil).

LCMS: (Method A) 512.2, (M+1), Rt. 5.46 min, 93.5% (max), 92.9% (220 nm).

Applying the procedure described in example 3, step 7 the following acids have been prepared from the corresponding esters:

EXAMPLE 15

(2S,4S)-4-[2-(4-Fluoro-phenyl)-1,1-dimethyl-ethyl-carbamoyl]-2-methyl-4-(4-pyridin-2-yl-benzoylamino)-butyric acid (table 1a, compound 10)

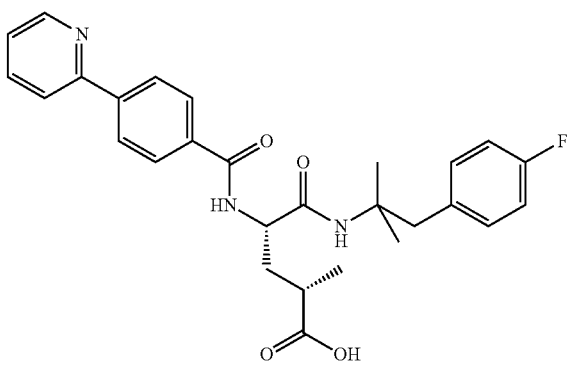 [SMILES: C[C@@H](C[C@H](NC(=O)c1ccc(-c2ccccn2)cc1)C(=O)NC(C)(C)Cc1ccc(F)cc1)C(=O)O]

$^1$H NMR: (400 MHz, DMSO-d6): δ 12.13 (s, 1H), 8.71 (d, J=3.88 Hz, 1H), 8.47 (d, J=8.64 Hz, 1H), 8.20 (d, J=8.44 Hz, 2H), 8.00-8.07 (m, 3H), 7.90-7.94 (m, 1H), 7.39-7.42 (m, 1H), 7.37 (s, 1H), 7.10-7.14 (m, 2H), 6.93-6.97 (m, 2H), 4.51-4.53 (m, 1H), 3.05 (d, J=12.88 Hz, 1H), 2.88 (d, J=13.00 Hz, 1H), 2.42-2.43 (m, 1H), 2.09-2.15 (m, 1H), 1.66-1.71 (m, 1H), 1.23 (s, 3H), 1.16 (s, 3H), 1.08 (d, J=7.00 Hz, 3H),.

LCMS: (Method A) 492.3 (M+1), Rt. 4.34 min, 96.9% (max), 98.8% (254 nm).

HPLC: (Method A) Rt. 3.53 min, 96.6% (max), 97.9% (254 nm).

Chiral purity: 99.7%

EXAMPLE 16

(2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid (table 1a, compound 11)

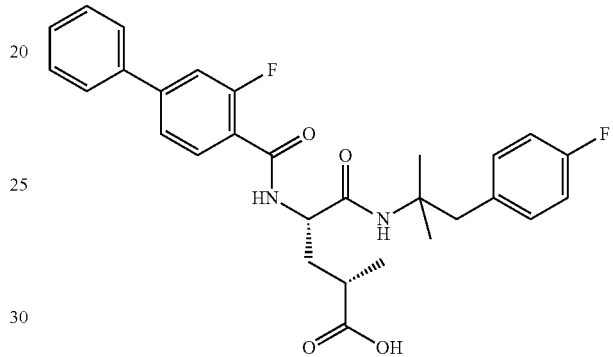

$^1$H NMR: (400 MHz, DMSO-d6): δ 12.31 (s, 1H), 8.30-8.33 (m, 1H), 7.71-7.77 (m, 3H), 7.61-7.63 (m, 2H), 7.48-7.52 (m, 3H), 7.41-7.45 (m, 1H), 7.18-7.15 (m, 2H), 6.97-7.01 (m, 2H), 4.48-4.54 (m, 1H), 3.09 (d, J=12.64 Hz, 1H), 2.87 (d, J=13.00 Hz, 1H), 2.37-2.42 (m, 1H), 1.97-2.05 (m, 1H), 1.61-1.67 (m, 1H), 1.37 (s, 3H), 1.34 (s, 3H), 1.09 (d, J=6.96 Hz, 3H),.

LCMS: (Method A) 509.3 (M+1), Rt. 5.27 min, 95.5% (max), 95.9% (254 nm).

HPLC: (Method A) Rt. 5.29 min, 95.8% (max), 95.1% (254 nm).

Chiral purity: 100%

EXAMPLE 17

(2S,4S)-4-[2-(4-Fluoro-phenyl)-1,1-dimethyl-ethyl-carbamoyl]-2-methyl-4-[4-(1-methyl-1H-pyrazol-3-yl)-benzoylamino]-butyric acid (table 1, compound 9)

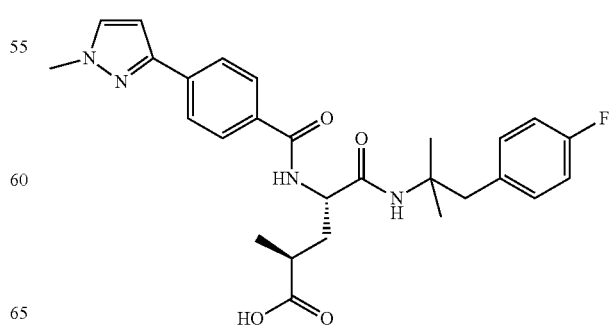

¹H NMR: (400 MHz, DMSO-d6): δ 12.15 (s, 1H), 8.31 (d, J=8.64 Hz, 1H), 8.25 (s, 1H), 7.87-7.96 (m, 2H), 7.66 (d, J=8.28 Hz, 2H), 7.33 (s, 1H), 6.91-7.12 (m, 4H), 4.47-4.51 (m, 1H), 3.87 (s, 3H), 3.03 (d, J=13.04 Hz, 1H), 2.87 (d, J=12.96 Hz, 1H), 2.37-2.41 (m, 1H), 2.06-2.09 (m, 1H), 1.63-1.69 (m, 1H), 1.34 (s, 3H), 1.22 (s, 3H), 1.05 (d, J=9.88 Hz, 3H),.

LCMS: (Method A) 495.2, (M+1), Rt. 4.15 min, 95.8% (max), 94.5% (254 nm).

HPLC: (Method A) Rt. 4.11 min, 96.2% (max), 93.1% (254 nm).

Chiral purity: 100%

EXAMPLE 18

(2S,4S)-4-[2-(4-Fluoro-phenyl)-1,1-dimethyl-ethyl-carbamoyl]-4-{[5-(4-fluoro-phenyl)-thiazole-2-carbonyl]-amino}-2-methyl-butyric acid (table 1a, compound 2)

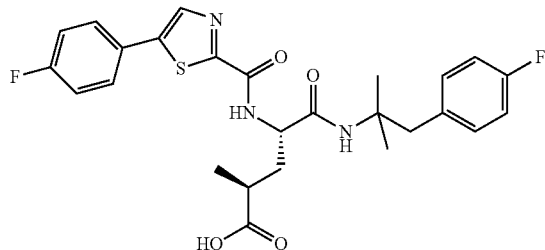 [SMILES: C[C@@H](C[C@H](NC(=O)c1ncc(-c2ccc(F)cc2)s1)C(=O)NC(C)(C)Cc1ccc(F)cc1)C(=O)O]

¹H NMR: (400 MHz, DMSO-d6): δ 9.71 (s, 1H), 8.57 (d, J=7.68 Hz, 1H), 8.39 (s, 1H), 7.82-7.86 (m, 2H), 7.31-7.35 (m, 2H), 7.15-7.19 (m, 2H), 7.01 (t, J=8.84 Hz, 2H), 4.41-4.47 (m, 1H), 3.06 (d, J=13.08 Hz, 1H), 2.91 (d, J=13.00 Hz, 1H), 1.50-1.91 (m, 3H), 1.22 (d, J=3.44 Hz, 6H), 0.84 (d, J=6.60 Hz, 3H).

LCMS: (Method A) 516.3, (M+1), Rt. 5.19 min, 98.9% (max), 98.4% (220 nm).

HPLC: (Method A) Rt. 5.21 min, 97.1% (max), 95.6% (220 nm).

Chiral purity: 100%

EXAMPLE 19

(2S,4S)-4-[2-(4-Fluoro-phenyl)-1,1-dimethyl-ethyl-carbamoyl]-4-{[2-(4-fluoro-phenyl)-thiazole-5-carbonyl]-amino}-2-methyl-butyric acid (table 1a, compound 20)

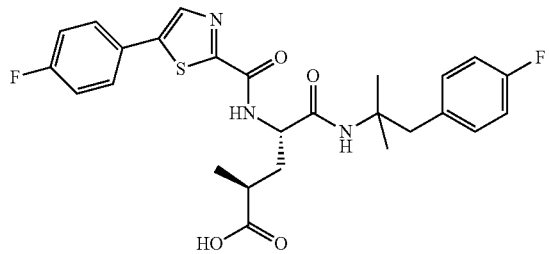 [SMILES: C[C@@H](C[C@H](NC(=O)c1ncc(-c2ccc(F)cc2)s1)C(=O)NC(C)(C)Cc1ccc(F)cc1)C(=O)O]

¹H NMR: (400 MHz, DMSO-d6): δ 12.18 (s, 1H), 8.74 (d, J=8.64 Hz, 1H), 8.59 (s, 1H), 8.04-8.08 (m, 2H), 7.44 (s, 1H), 7.37 (t, J=8.84 Hz, 2H), 7.09-7.13 (m, 2H), 6.96 (t, J=8.76 Hz, 2H), 4.44-4.50 (m, 1H), 3.06 (d, J=12.96 Hz, 1H), 2.86 (d, J=13.00 Hz, 1H), 2.39-2.40 (m, 1H), 2.07-2.08 (m, 1H), 1.65-1.71 (m, 1H), 1.24 (s, 3H), 1.15 (s, 3H), 1.06 (d, J=6.96 Hz, 3H).

LCMS: (Method A) 516.0, (M+1), Rt. 5.19 min, 96.3% (max), 94.2% (254 nm).

HPLC: (Method A) Rt. 4.93 min, 96.9% (max), 94.7% (254 nm).

Chiral purity: 94.2%

EXAMPLE 20

(2S,4S)-4-[2-(4-Fluoro-phenyl)-1,1-dimethyl-ethyl-carbamoyl]-2-methyl-4-[4-(5-methyl-thiazol-2-yl)-benzoylamino]-butyric acid (table 1a, compound 19)

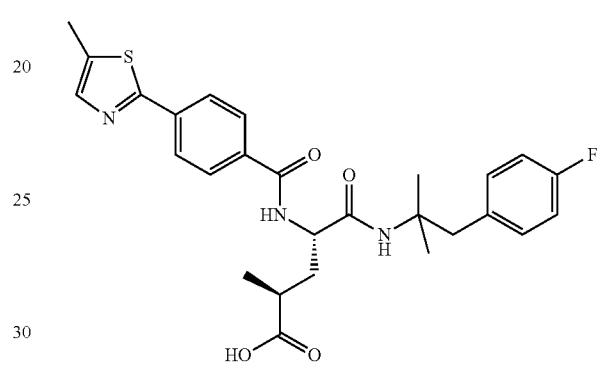

¹H NMR: (400 MHz, DMSO-d6): δ 12.19 (s, 1H), 8.49 (d, J=8.64 Hz, 1H), 7.95-8.01 (m, 4H), 7.67 (d, J=1.20 Hz, 1H), 7.36 (s, 1H), 7.09-7.13 (m, 2H), 6.95 (t, J=8.84 Hz, 2H), 4.47-4.52 (m, 1H), 3.05 (d, J=12.96 Hz, 1H), 2.87 (d, J=13.04 Hz, 1H), 2.38-2.51 (m, 4H), 2.06-2.12 (m, 1H), 1.65-1.70 (m, 1H), 1.23 (s, 3H), 1.15 (s, 3H), 1.07 (d, J=7.04 Hz, 3H),.

LCMS: (Method A) 512.2, (M+1), Rt. 4.64 min, 98.8% (max), 97.7% (220 nm).

HPLC: (Method A) Rt. 4.67 min, 98.7% (max), 97.5% (220 nm).

Chiral purity: 99.6%

EXAMPLE 21

(2S,4S)-4-[2-(4-Fluoro-phenyl)-1,1-dimethyl-ethyl-carbamoyl]-2-methyl-4-(4-pyrazol-1-yl-benzoylamino)-butyric acid

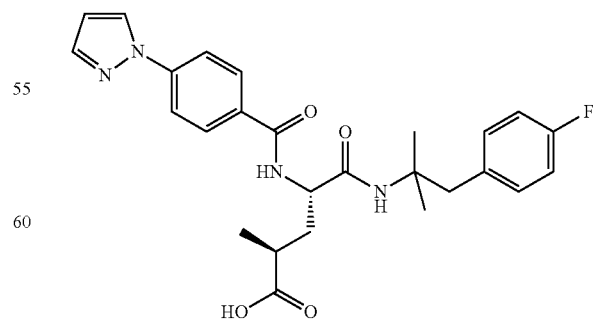

¹H NMR: (400 MHz, DMSO-d6): δ 12.21 (s, 1H), 8.63 (d, J=2.52 Hz, 1H), 8.46 (d, J=8.40 Hz, 1H), 8.02-8.04 (m, 2H), 7.95-7.97 (m, 2H), 7.80 (d, J=1.60 Hz, 1H), 7.38 (s, 1H), 7.10-7.13 (m, 2H), 6.95 (t, J=8.80 Hz, 2H), 6.59-6.60 (m, 1H), 4.47-4.53 (m, 1H), 3.04 (d, J=13.00 Hz, 1H), 2.87 (d, J=13.00 Hz, 1H), 2.38-2.44 (m, 1H), 2.06-2.14 (m, 1H), 1.64-1.70 (m, 1H), 1.23 (s, 3H), 1.16 (s, 3H), 1.07 (d, J=7.04 Hz, 3H),.

LCMS: (Method A) 481.0, (M+1), Rt. 4.33 min, 97.2% (max), 94.9% (254 nm).

HPLC: (Method A) Rt. 4.36 min, 97.9% (max), 95.5% (254 nm).

Chiral purity: 99.6%

EXAMPLE 22

(2S,4S)-4-[2-(4-Fluoro-phenyl)-1,1-dimethyl-ethyl-carbamoyl]-4-{[1-(4-fluoro-phenyl)-piperidine-4-carbonyl]-amino}-2-methyl-butyric acid (table 1a, compound 12)

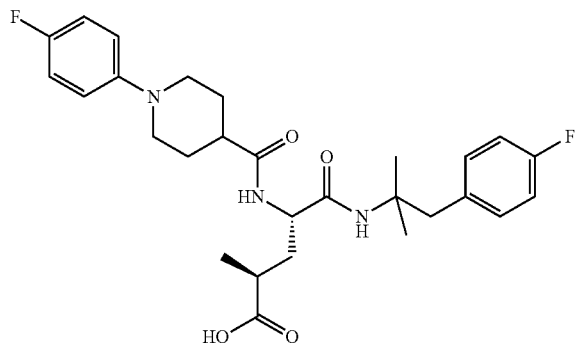 [SMILES: C[C@@H](C[C@H](NC(=O)C1CCN(c2ccc(F)cc2)CC1)C(=O)NC(C)(C)Cc1ccc(F)cc1)C(=O)O]

¹H NMR: (400 MHz, DMSO-d6): δ 12.12 (s, 1H), 7.93 (d, J=9.20 Hz, 1H), 7.27 (s, 1H), 6.98-7.11 (m, 8H), 4.25-4.31 (m, 1H), 3.59-3.62 (m, 2H), 3.10 (d, J=12.84 Hz, 1H), 2.81 (d, J=12.92 Hz, 1H), 2.44-2.48 (m, 1H), 1.73-1.91 (m, 6H), 1.52-1.58 (m, 1H), 1.22 (s, 3H), 1.11 (s, 3H), 1.02 (d, J=7.00 Hz, 3H),.

LCMS: (Method A) 516.3, (M+1), Rt. 3,6^13.61 min, 98.3% (max), 97.8% (220 nm),.

HPLC: (Method A) Rt. 3.64 min, 99.1% (max), 99.1% (220 nm).

Chiral purity: 100%

EXAMPLE 23

(2S,4S)-4-[2-(4-Fluoro-phenyl)-1,1-dimethyl-ethyl-carbamoyl]-2-methyl-4-[(4-phenyl-piperidine-1-carbonyl)-amino]-butyric acid (table 1a, compound 18)

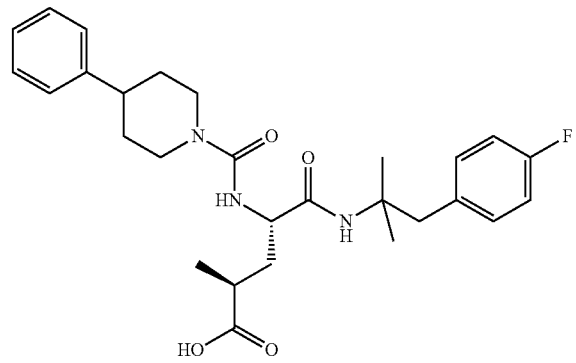 [SMILES: C[C@@H](C[C@H](NC(=O)N1CCC(c2ccccc2)CC1)C(=O)NC(C)(C)Cc1ccc(F)cc1)C(=O)O]

¹H NMR: (400 MHz, DMSO-d6): δ 12.19 (s, 1H), 7.26-7.29 (m, 2H), 7.11-7.20 (m, 6H), 7.01 (t, J=8.76 Hz, 2H), 6.37 (d, J=8.80 Hz, 1H), 4.10 (d, J=12.96 Hz, 3H), 3.02 (d, J=13.00 Hz, 1H), 2.89 (d, J=13.00 Hz, 1H), 2.65-2.88 (m, 3H), 2.35-2.40 (m, 1H), 1.89-1.91 (m, 1H), 1.70-1.73 (m, 2H), 1.56-1.61 (m, 1H), 1.42-1.48 (m, 2H), 1.22 (s, 3H), 1.19 (s, 3H), 1.05 (d, J=7.00 Hz, 3H),.

LCMS: (Method B) 498.3, (M+1), Rt. 4.91 min, 95.0% (max), 94.4% (220 nm).

HPLC: (Method B) Rt. 4.94 min, 94.7% (max), 90.9% (220 nm).

Chiral purity: 100%

EXAMPLE 24

(2S,4S)-4-[2-(4-Fluoro-phenyl)-1,1-dimethyl-ethyl-carbamoyl]-2-methyl-4-[(4-phenyl-piperazine-1-carbonyl)-amino]-butyric acid methyl ester

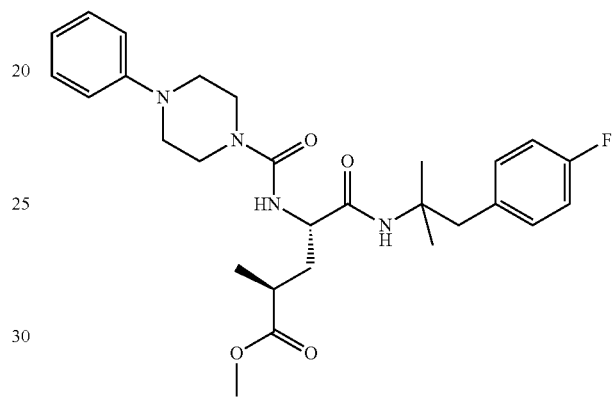

Synthesized using the protocol similar to example 13 using 4-Amino-4-[2-(4-fluoro-phenyl)-1,1-dimethyl-ethyl-carbamoyl]-2-methyl-butyric acid methyl ester TFA salt (200 mg, 0.89 mmol) and 4-phenyl piperazine (144 mg, 0.89 mmol) to get the titled compound as a colourless oil.

Yield: 120 mg, (54%, colourless oil.).

LCMS: (Method A) 513.3, (M+1), Rt. 4.38 min, 95.9% (max).

EXAMPLE 25

(2S,4S)-4-[2-(4-Fluoro-phenyl)-1,1-dimethyl-ethyl-carbamoyl]-2-methyl-4-[(4-phenyl-piperazine-1-carbonyl)-amino]-butyric acid (table 1a, compound 15)

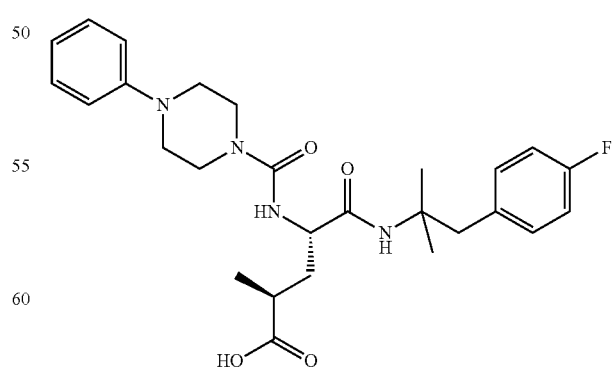

¹H NMR: (400 MHz, DMSO-d6): δ 12.13 (s, 1H), 7.19-7.25 (m, 3H), 7.10-7.13 (m, 2H), 6.97-7.02 (m, 4H), 6.81 (t, J=7.24 Hz, 1H), 6.49 (d, J=8.64 Hz, 1H), 4.08-4.14 (m, 1H), 3.46-3.47 (m, 4H), 3.09-3.10 (m, 4H), 3.02 (d, J=13.04 Hz,

1H), 2.87 (d, J=13.00 Hz, 1H), 2.34-2.39 (m, 1H), 1.88-1.94 (m, 1H), 1.55-1.60 (m, 1H), 1.17 (s, 3H), 1.13 (s, 3H), 1.04 (d, J=6.80 Hz, 3H),.

LCMS: (Method A) 499.2, (M+1), Rt. 3.93 min, 96.8% (max), 96.2% (254 nm).

HPLC: (Method A) Rt. 3.91 min, 94.4% (max), 96.1% (254 nm).

Chiral purity: 100%

EXAMPLE 26

4-[(Biphenyl-4-carbonyl)-amino]-2-methyl-4-(3,4,5-trimethoxy-benzylcarbamoyl)-butyric acid (table 1a, compound 1)

Step 1: (2S,4S)-4-tert-Butoxycarbonylamino-2-methyl-4-(3,4,5-trimethoxy-benzylcarbamoyl)-butyric acid methyl ester

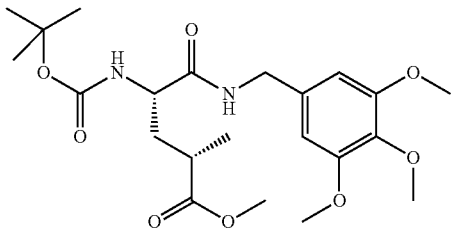 [SMILES: COC(=O)[C@@H](C)C[C@H](NC(=O)OC(C)(C)C)C(=O)NCc1cc(OC)c(OC)c(OC)c1]

Synthesized using the protocol similar to example 1, step 4 using (2S,4S)-2-tert-Butoxycarbonylamino-4-methyl-pentanedioic acid 5-methyl ester (400 mg, 1.4 mmol) and 3,4,5-trimethoxy benzylamine (310 mg, 1.5 mmol) to get the titled compound as a colourless gum.

Yield: 0.3 g, (48%, colourless gum).

LCMS: (Method A) 455.3, (M+1), Rt. 3.97 min, 98.5% (max), 98.7% (220 nm).

Step 2: (2S,4S)-4-Amino-2-methyl-4-(3,4,5-trimethoxy-benzylcarbamoyl)-butyric acid methyl ester TFA salt

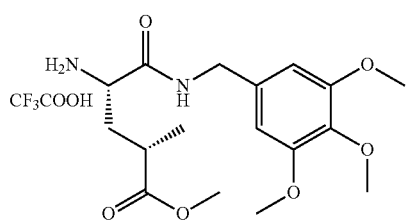 [SMILES: "CF3COOH" ; COC(=O)[C@@H](C)C[C@H](N)C(=O)NCc1cc(OC)c(OC)c(OC)c1]

Synthesized using the protocol similar to example 1, step 5 using (2S,4S)-4-tert-Butoxycarbonylamino-2-methyl-4-(3,4,5-trimethoxy-benzylcarbamoyl)-butyric acid methyl ester (300 mg, 0.66 mmol) and TFA (2 mL) to get the titled compound as a TFA salt.

Yield: 0.25 g, (83%, colourless gum).

LCMS: (Method A) 355.2, (M+1), Rt. 2.39 min, 93.8% (max), 93.7% (220 nm).

Step 3: (2S,4S)-4-[(Biphenyl-4-carbonyl)-amino]-2-methyl-4-(3,4,5-trimethoxy-benzylcarbamoyl)-butyric acid methyl ester

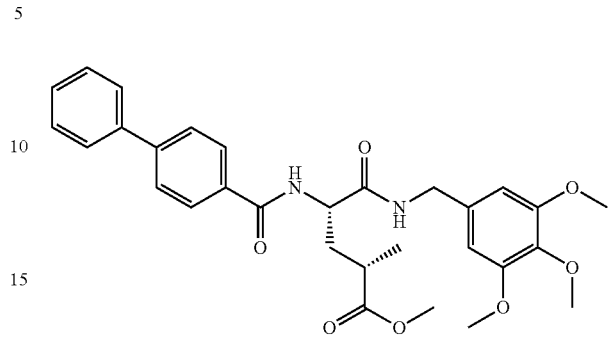

Synthesized using the protocol similar to example 1, step 6 using (2S,4S)-4-Amino-2-methyl-4-(3,4,5-trimethoxy-benzylcarbamoyl)-butyric acid methyl ester TFA salt (250 mg, 0.53 mmol) and biphenyl-4-carboxylic acid (105 mg, 0.53 mmol) to get the titled compound as an off white solid.

Yield: 110 mg, (38%, off white solid).

LCMS: (Method A) 535.2, (M+1), Rt. 4.72 min, 95.5% (max).

Step 4: (2S,4S)-4-[(Biphenyl-4-carbonyl)-amino]-2-methyl-4-(3,4,5-trimethoxy-benzylcarbamoyl)-butyric acid

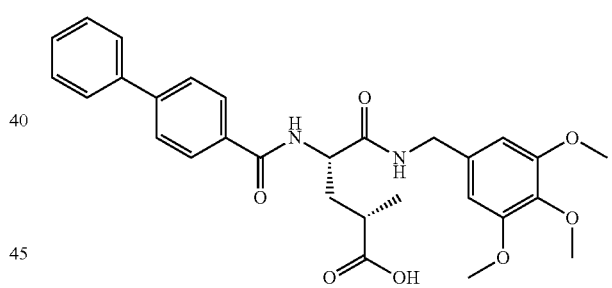

Synthesized using the protocol similar to example 1, step 7 using (2S,4S)-4-[(Biphenyl-4-carbonyl)-amino]-2-methyl-4-(3,4,5-trimethoxy-benzylcarbamoyl)-butyric acid methyl ester (100 mg, 0.19 mmol) to get the titled compound as an off white solid.

Yield: 60 mg, (62%, Off white solid.).

$^1$H NMR: (400 MHz, DMSO-d6): δ 12.61 (s, 1H), 8.28-8.61 (m, 2H), 7.95-8.02 (m, 2H), 7.72-7.80 (m, 4H), 7.47-7.51 (m, 2H), 7.38-7.42 (m, 1H), 6.54 (d, J=8.60 Hz, 2H), 4.41-4.54 (m, 1H), 4.17-4.25 (m, 2H), 3.71-3.73 (m, 6H), 3.58-3.60 (m, 3H), 2.06-2.20 (m, 1H), 1.73-1.92 (m, 1H), 1.04 (d, J=6.80 Hz, 3H),.

LCMS: (Method A) 521.3, (M+1), Rt. 4.10 and 4.21 min, (48.8 and 50.1) % (max), (49.3 and 50.1) % (254 nm).

HPLC: (Method A) Rt. 4.13 and 4.25 min, (49.6 and 49.1) % (max), (49.2 and 49.3) % (254 nm).

Chiral purity: partial racemisation of stereocenter at C2.

EXAMPLE 27 AND 28

Step 1: (2S,4S)-4-tert-Butoxycarbonylamino-4-[2-(4-fluoro-phenyl)-1-methyl-ethylcarbamoyl]-2-methyl-butyric acid methyl ester

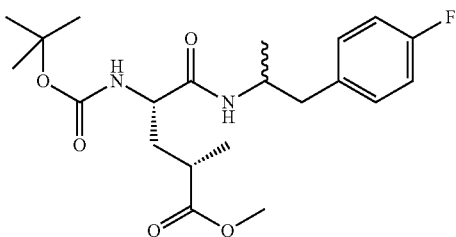 [SMILES: COC(=O)[C@@H](C)C[C@H](NC(=O)OC(C)(C)C)C(=O)NC(C)Cc1ccc(F)cc1]

Synthesized using the protocol similar to example, step 4 using (2S,4S)-2-tert-Butoxycarbonylamino-4-methyl-pentanedioic acid 5-methyl ester (1.5 g, 5.45 mmol) and 1-(4-fluorophenylpropane-2-amine hydrochloride (1.12 g, 5.99 mmol) to get the titled compound as a colourless gum).

Yield: 0.9 g, (40%, colourless gum).
LCMS: (Method A) 411.2, (M+1), Rt. 4.74 min, 81.2% (max).

Step 2: (2S,4S)-4-Amino-4-[2-(4-fluoro-phenyl)-1-methyl-ethylcarbamoyl]-2-methyl-butyric acid methyl ester TFA salt

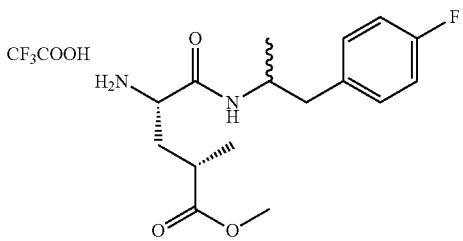 [SMILES: "CF3COOH" ; COC(=O)[C@@H](C)C[C@H](N)C(=O)NC(C)Cc1ccc(F)cc1]

Synthesized using the protocol similar to example 1, step 5 using (2S,4S)-4-tert-Butoxycarbonylamino-4-[2-(4-fluoro-phenyl)-1-methyl-ethylcarbamoyl]-2-methyl-butyric acid methyl ester (900 mg, 2.19 mmol) and TFA (2 mL) to get the titled compound as a TFA salt.

Yield: 0.6 g, (65%, colourless gum).
¹H NMR: 400 MHz, CDCl3-d6: δ 8.21 (s, 2H), 7.64-7.66 (m, 1H), 7.12-7.27 (m, 3H), 6.93-6.98 (m, 2H), 3.65-4.11 (m, 6H), 2.54-2.78 (m, 2H), 1.91-2.23 (m, 2H), 0.93-1.20 (m, 6H).

Step 3: (2S,4S)-4-[(Biphenyl-4-carbonyl)-amino]-4-[2-(4-fluoro-phenyl)-1-methyl-ethylcarbamoyl]-2-methyl-butyric acid methyl ester

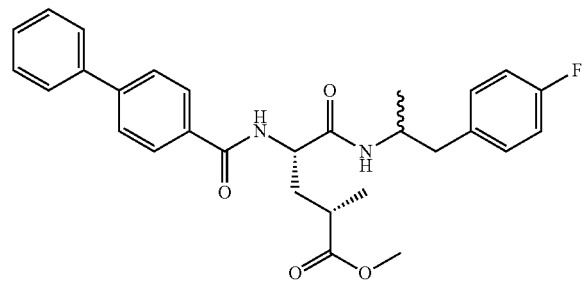 [SMILES: COC(=O)[C@@H](C)C[C@H](NC(=O)c1ccc(-c2ccccc2)cc1)C(=O)NC(C)Cc1ccc(F)cc1]

Synthesized using the protocol similar to example 1, step 6 using (2S,4S)-4-Amino-4-[2-(4-fluoro-phenyl)-1-methyl-ethylcarbamoyl]-2-methyl-butyric acid methyl ester TFA salt (600 mg, 1.43 mmol) and biphenyl-4-carboxylic acid (284 mg, 1.43 mmol) to get the titled compound as an off white solid which showed two isomers in chiral purity which were separated by chiral prep and the two isomers obtained showed the following data.

Isomer A
Yield: 80 mg, (12%, off white solid).
¹H NMR: 400 MHz, CDCl₃: δ 7.84-7.86 (m, 2H), 7.41-7.71 (m, 7H), 7.06-7.10 (m, 2H), 6.79-6.84 (m, 3H), 6.41-6.53 (m, 1H), 4.57-4.58 (m, 1H), 4.20-4.24 (m, 1H), 3.64 (s, 3H), 2.71-2.74 (m, 2H), 1.97-2.61 (m, 3H), 1.17-1.25 (m, 6H),.
LCMS: (Method A) 491.2, (M+1), Rt. 5.26 min, 96.9% (max), 93.9% (254 nm).

Isomer B
Yield: 90 mg, (13%, off white solid).
¹H NMR: 400 MHz, CDCl₃δ 7.86-7.88 (m, 2H), 7.62-7.69 (m, 2H), 7.40-7.50 (m, 2H), 7.15-7.19 (m, 3H), 6.93-6.98 (m, 5H), 6.47-6.51 (m, 1H), 4.54-4.56 (m, 1H), 4.25-4.29 (m, 1H), 3.67 (s, 3H), 2.78-2.81 (m, 2H), 1.81-2.12 (m, 3H), 1.16-1.18 (m, 6H),
LCMS: (Method A) 491.2, (M+1), Rt. 5.28 min, 98.8% (max), 97.2% (254 nm).

Step 4: (2S,4S)-4-[(Biphenyl-4-carbonyl)-amino]-4-[2-(4-fluoro-phenyl)-1-methyl-ethylcarbamoyl]-2-methyl-butyric acid

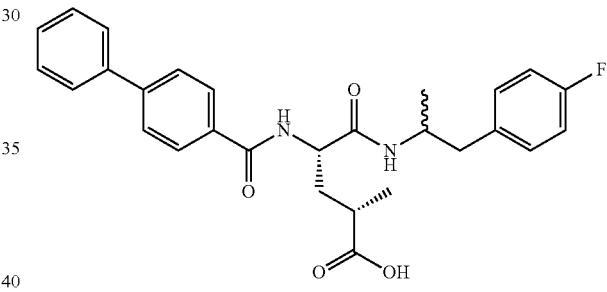

Table 1a, Compound 17:
Synthesized using the protocol similar to example 1, step 7 (2S,4S)-4-[(Biphenyl-4-carbonyl)-amino]-4-[2-(4-fluoro-phenyl)-1-methyl-ethylcarbamoyl]-2-methyl-butyric acid methyl ester (Isomer A) (80 mg, 0.16 (mmol) to get the titled compound as an off white solid.
Yield: 50 mg, (65%, Off white solid.).
¹H NMR: 400 MHz, DMSO-d6: δ 12.22 (s, 1H), 8.41 (d, J=8.44 Hz, 1H), 7.98 (d, J=8.40 Hz, 2H), 7.85 (d, J=8.12 Hz, 1H), 7.72-7.79 (m, 4H), 7.49 (t, J=7.80 Hz, 2H), 7.39-7.42 (m, 1H), 7.19-7.23 (m, 2H), 6.99 (t, J=8.84 Hz, 2H), 4.45-4.50 (m, 1H), 3.92-3.95 (m, 1H), 2.65-2.74 (m, 3H), 2.31-2.50 (m, 1H), 2.01-2.07 (m, 1H), 1.62-1.69 (m, 1H), 1.07 (d, J=7.04 Hz, 3H), 1.00 (d, J=6.64 Hz, 3H).
LCMS: (Method A) 477.2, (M+1), Rt. 4.79 min, 98.7% (max), 98.5% (254 nm).
HPLC: (Method A) Rt. 4.81 min, 98.7% (max), 98.4% (254 nm).
Chiral purity: 90.72%

Table 1a, Compound 3:
Synthesized using the protocol similar to example 1, step 7 (2S,4S)-4-[(Biphenyl-4-carbonyl)-amino]-4-[2-(4-fluoro-phenyl)-1-methyl-ethylcarbamoyl]-2-methyl-butyric acid methyl ester (Isomer B) (90 mg, 0.18 mmol) to get the titled compound as an off white solid.
Yield: 55 mg, (63%, Off white solid.).
¹H NMR: 400 MHz, DMSO-d6: δ 12.21 (s, 1H), 8.39 (d, J=8.48 Hz, 1H), 7.98 (d, J=8.36 Hz, 2H), 7.88 (d, J=8.20 Hz, 1H), 7.72-7.78 (m, 4H), 7.49 (t, J=7.80 Hz, 2H), 7.38-7.42 (m, 1H), 7.17-7.21 (m, 2H), 6.98 (t, J=8.84 Hz, 2H), 4.42-4.48 (m, 1H), 3.92-3.96 (m, 1H), 2.66 (d, J=6.80 Hz, 2H), 2.32-2.34 (m, 1H), 1.92-1.99 (m, 1H), 1.53-1.59 (m, 1H), 1.06 (d, J=6.64 Hz, 6H).

LCMS: (Method A) 477.2, (M+1), Rt. 4.74 min, 97.7% (max), 98.0% (254 nm).

HPLC: (Method A) Rt. 4.77 min, 98.9% (max), 97.7% (254 nm).

Chiral purity: 99.02%

EXAMPLE 29

(2S,4S)-4-[(Biphenyl-4-carbonyl)-amino]-4-(1,1-dimethyl-2-pyridin-3-yl-ethylcarbamoyl)-2-methyl-butyric acid Step 1: (2S,4S)-4-tert-Butoxycarbonylamino-4-(1,1-dimethyl-2-pyridin-3-yl-ethylcarbamoyl)-2-methyl-butyric acid methyl ester

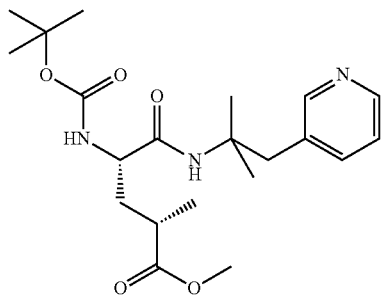 [SMILES: COC(=O)[C@@H](C)C[C@H](NC(=O)OC(C)(C)C)C(=O)NC(C)(C)Cc1cccnc1]

Synthesized using the protocol similar to example 1, step 4 using (2S,4S)-2-tert-Butoxycarbonylamino-4-methyl-pentanedioic acid 5-methyl ester (0.37 g, 1.34 mmol) and (1,1-dimethyl-2-pyridin-3-ylethyl)amine (0.2 g, 1.34 mmol) to get the titled compound as a colorless gum.

Yield: 0.12 g, (23%, colourless gum).

LCMS: (Method C) 408.3, (M+1), Rt. 4.87 min, 94.0% (ADC1 A).

Step 2: (2S,4S)-4-Amino-4-(1,1-dimethyl-2-pyridin-3-yl-ethylcarbamoyl)-2-methyl-butyric acid methyl ester TFA salt

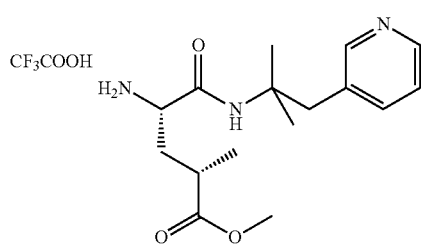 [SMILES: "CF3COOH" ; COC(=O)[C@@H](C)C[C@H](N)C(=O)NC(C)(C)Cc1cccnc1]

Synthesized using the protocol similar to example 1, step 5 using (2S,4S)-4-tert-Butoxycarbonylamino-4-(1,1-dimethyl-2-pyridin-3-yl-ethylcarbamoyl)-2-methyl-butyric acid methyl ester (110 mg, 0.27 mmol) and TFA (2 mL) to get the titled compound as a TFA salt which was used as such for the next step (confirmed by TLC only).

Yield: 50 mg, (44%, colorless gum).

Step 3: (2S,4S)-4-[(Biphenyl-4-carbonyl)-amino]-4-(1,1-dimethyl-2-pyridin-3-yl-ethylcarbamoyl)-2-methyl-butyric acid methyl ester

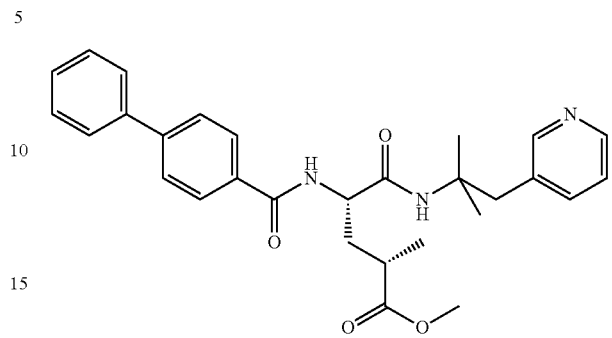

Synthesized using the protocol similar to example 1, step 6 using (2S,4S)-4-Amino-4-(1,1-dimethyl-2-pyridin-3-yl-ethylcarbamoyl)-2-methyl-butyric acid methyl ester TFA salt (50 mg, 0.12 mmol) and biphenyl-4-carboxylic acid (24 mg, 0.12 mmol) to get the titled compound as an off white solid.

Yield: 20 mg, (20 mg, off white solid)

LCMS: (Method A) 488.3, (M+1), Rt. 3.87 min, 36.1% (max).

Step 4: (2S,4S)-4-[(Biphenyl-4-carbonyl)-amino]-4-(1,1-dimethyl-2-pyridin-3-yl-ethylcarbamoyl)-2-methyl-butyric acid (table 1a, compound 4)

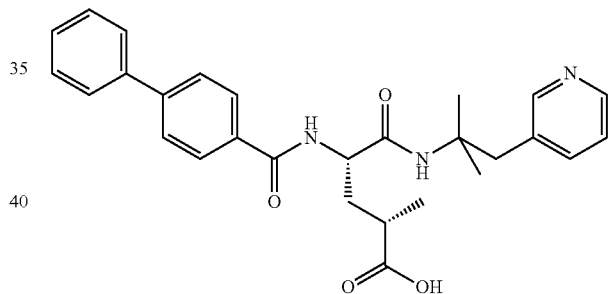

Synthesized using the protocol similar to example 1, step 7 using (2S,4S)-4-[(Biphenyl-4-carbonyl)-amino]-4-(1,1-dimethyl-2-pyridin-3-yl-ethylcarbamoyl)-2-methyl-butyric acid methyl ester (20 mg, 0.04 mmol) to get the titled compound as its TFA salt (after prep).

Yield: 10 mg, (41%, Yellow gummy solid.).

$^1$H NMR: (400 MHz, DMSO-d6): δ 12.11 (s, 1H), 8.45-8.54 (m, 3H), 8.01 (d, J=8.20 Hz, 2H), 7.73-7.79 (m, 5H), 7.39-7.52 (m, 5H), 4.43-4.48 (m, 1H), 3.25 (d, J=12.92 Hz, 1H), 2.96 (d, J=13.16 Hz, 1H), 1.98-2.48 (m, 3H), 1.29 (s, 3H), 1.23 (s, 3H), 1.08 (d, J=7.00 Hz, 3H).

LCMS: (Method A) 474.2, (M-TFA), Rt. 3.48 min, 92.9% (max), 90.2% (254 nm).

HPLC: (Method A) Rt. 3.46 min, 91.5% (max), 93.8% (254 nm).

EXAMPLE 30

(2S,4S)-2-[(Biphenyl-4-carbonyl)-amino]-2-[2-(4-fluoro-phenyl)-1,1-dimethyl-ethylcarbamoyl]-ethyl}-pentanoic acid (table 1a, compound 7)

Applying the procedures described for example 1, steps 2-7, but using allyl bromide in step 2 as alkylating agent, followed by hydrogenation of the double bond, and using Biphenyl-4-carboxylic acid in step 6, led to the titled compound.

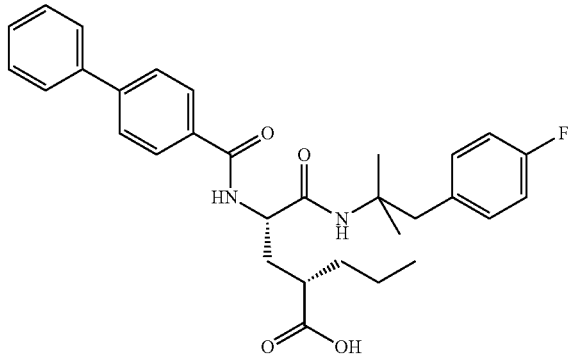 [SMILES: CCC[C@@H](C[C@H](NC(=O)c1ccc(-c2ccccc2)cc1)C(=O)NC(C)(C)Cc1ccc(F)cc1)C(=O)O]

$^1$H NMR: (300 MHz, CDCl3) δ=7.88 (d, J=8.5 Hz, 2H), 7.64-7.57 (m, 4H), 7.44-7.30 (m, 4H), 7.04-7.01 (m, 3H), 6.82 (t, J=8.7 Hz, 2H), 4.66 (q, J=8.1 Hz, 1H), 3.18 (d, J=13.5 Hz, 1H), 2.86 (d, J=13.5 Hz, 1H), 2.34-2.26 (m, 1H), 2.16-2.00 (m, 2H), 1.80-1.60 (m, 1H), 1.51-1.35 (m, 4H), 1.35-1.15 (m, 5H), 0.89 (t, J=7.2 Hz, 3H).

LCMS: 519,2 (M+1), Rt. 3.76 min., (Method: Column: Waters XBridge (C18, 50×2.1 mm, 3.5 micron) valve: 0, Flow: 0.8 ml/min Column temp: 35° C., Eluent A: 0.1% Formic acid in acetonitrile, Eluent B: 0.1% Formic acid in water, Lin. Gradient: t=0 min 5% A, t=3.5 min 98% A, t=6 min 98% A, Detection: DAD (220-320 nm), Detection: MSD (ESI pos/neg) mass range: 100-800.)

EXAMPLE 31

(2S,4S)-2-Benzyl-4-[(biphenyl-4-carbonyl)-amino]-4-[2-(4-fluoro-phenyl)-1,1-dimethyl-ethylcarbamoyl]-butyric acid (table 1a, compound 6)

Applying the procedures described for example 1, steps 2-7, but using benzyl bromide in step 2 as alkylating agent and using Biphenyl-4-carboxylic acid in step 6, led to the titled compound.

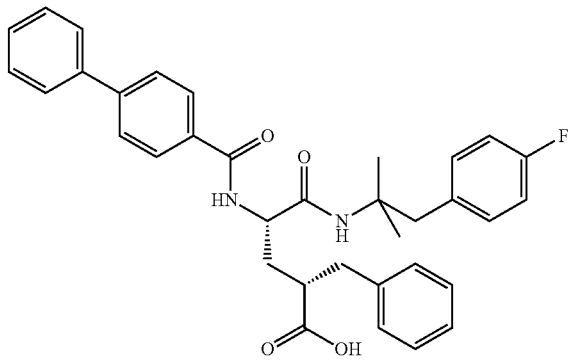 [SMILES: CC(C)(Cc1ccc(F)cc1)NC(=O)[C@H](C[C@H](Cc1ccccc1)C(=O)O)NC(=O)c1ccc(-c2ccccc2)cc1]

$^1$H NMR (300 MHz, CDCl$_3$) δ=7.85 (d, J=8.5 Hz, 2H), 7.61-7.55 (m, 5H), 7.43-7.36 (m, 3H), 7.25-7.11 (m, 5H), 6.99-6.89 (m, 3H), 6.77 (t, J=8.5 Hz, 2H), 4.67 (q, J=8.7 Hz, 1H), 3.11-3.01 (m, 2H), 2.81-2.70 (m, 3H), 2.25-2.00 (m, 2H), 1.29 (s, 3H), 1.11 (s, 3H).

LCMS: 567,2 (M+1), Rt. 2.27 min., (Method: Column: Waters XBridge (C18, 30×2.1 mm, 3.5 micron) valve: 6, Flow: 1 ml/min Column temp: 35° C., Eluent A: 0.1% Formic acid in acetonitrile, Eluent B: 0.1% Formic acid in water, Lin. Gradient: t=0 min 5% A, t=1.6 min 98% A, t=3 min 98% A, Detection: DAD (220-320 nm), Detection: MSD (ESI pos/neg) mass range: 100-800.)

EXAMPLE 32

(2S,4S)-4-[(Biphenyl-4-carbonyl)-amino]-4-[2-(4-fluoro-phenyl)-1,1-dimethyl-ethylcarbamoyl]-2-methoxymethyl-butyric acid (table 1a, compound 8)

Applying the procedures described for example 1, steps 2-7, but using methoxymethyl bromide in step 2 as alkylating agent and using Biphenyl-4-carboxylic acid in step 6 led to the titled compound.

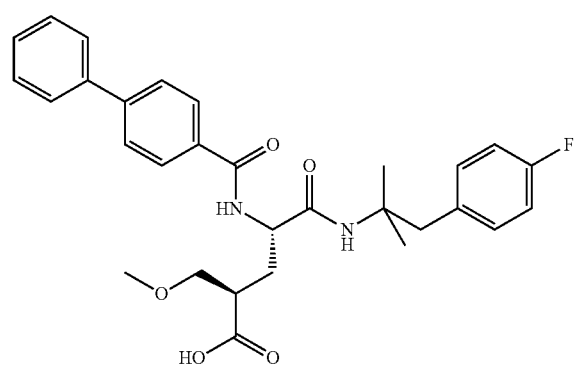 [SMILES: COC[C@@H](C[C@H](NC(=O)c1ccc(-c2ccccc2)cc1)C(=O)NC(C)(C)Cc1ccc(F)cc1)C(=O)O]

$^1$H NMR (300 MHz, DMSO-d$_6$) δ=12.29 (s, 1H), 8.45 (d, J=8.5 Hz, 1H), 7.99-7.94 (m, 2H), 7.80-7.73 (m, 4H), 7.51 (t, J=7.2 Hz, 2H), 7.42 (t, J=7.2 Hz, 1H), 7.39-7.26 (m, 1H), 7.14-7.10 (m, 2H), 6.93 (t, J=8.5 Hz, 2H), 4.55-4.40 (m, 1H), 3.50-3.48 (m, 2H), 3.22 (s, 3H), 3.06 (d, J=13.5 Hz, 1H), 2.87 (d, J=13.5 Hz, 1H), 2.65-2.55 (m, 1H), 2.10-1.95 (m, 1H), 1.95-1.80 (m, 1H), 1.24 (s, 3H), 1.17 (s, 3H).

LCMS: 521,2 (M+1), Rt. 2.27 min., (Method: Column: Waters XBridge (C18, 50×2.1 mm, 3.5 micron) valve: 0, Flow: 0.8 ml/min Column temp: 35° C., Eluent A: 0.1% Formic acid in acetonitrile, Eluent B: 0.1% Formic acid in water, Lin. Gradient: t=0 min 5% A, t=3.5 min 98% A, t=6 min 98% A, Detection: DAD (220-320 nm), Detection: MSD (ESI pos/neg) mass range: 100-800.)

EXAMPLE 33

(2S,4S)-4-[(Biphenyl-4-carbonyl)-amino]-4-[2-(4-fluoro-phenyl)-1,1-dimethyl-ethylcarbamoyl]-2-methyl-butyric acid (table 1a, compound 5)

Applying the procedures described for example 1, steps 2-7, and using Biphenyl-4-carboxylic acid in step 6, led to the titled compound.

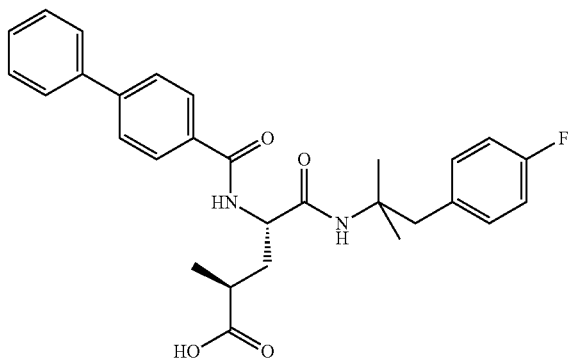 [SMILES: C[C@@H](C[C@H](NC(=O)c1ccc(-c2ccccc2)cc1)C(=O)NC(C)(C)Cc1ccc(F)cc1)C(=O)O]

¹H NMR (300 MHz, CDCl₃) δ=7.88 (d, J=8.5 Hz, 2H), 7.64-7.56 (m, 4H), 7.48-7.37 (m, 4H), 7.06-7.01 (m, 2H), 6.86-6.80 (m, 3H), 4.70 (q, J=8.5 Hz, 1H), 3.12 (d, J=13.5 Hz, 1H), 2.91 (d, J=13.5 Hz, 1H), 2.46-2.38 (m, 1H), 2.23-2.13 (m, 1H), 1.99-1.90 (m, 1H), 1.37 (s, 3H), 1.37-1.22 (m, 6H).

LCMS: 491,2 (M+1), Rt. 3.59 min., (Method: Column: Waters XBridge (C18, 50×2.1 mm, 3.5 micron) valve: 0, Flow: 0.8 ml/min Column temp: 35° C., Eluent A: 0.1% Formic acid in acetonitrile, Eluent B: 0.1% Formic acid in water, Lin. Gradient: t=0 min 5% A, t=3.5 min 98% A, t=6 min 98% A, Detection: DAD (220-320 nm), Detection: MSD (ESI pos/neg) mass range: 100-800.)

1HNMR:
Bruker 400 MHz
LCMS:
Method A
  Method: A-0.1% TFA in H₂O, B-0.1% TFA in ACN: Flow—2.0 mL/min.
  Column: XBridge C8 (50×4.6 mm, 3.5μ), +ve Mode
Method B
  A: 10 mM NH4HCO3, B:ACN; Flow Rate: 1.0 ml/min
  COLUMN:XBridge C8 (50×4.6 mm, 3.5μ), +ve Mode
Method C (ELSD)
  A: 0.1% TFA IN H₂O, B:0.1% TFA IN ACN; Flow Rate:2.0 ml/min
  COLUMN:XBridge C8 (50×4.6 mm, 3.5 A), +ve mode
HPLC:
Method A
  Method: A-0.1% TFA in H₂O, B-0.1% TFA in ACN: Flow—2.0 mL/min.
  Column: XBridge C8 (50×4.6 mm, 3.5 μm).
  Method B: A:10 mM NH4HCO3 in H2O, B:ACN; Flow Rate:0.8 ml/min
  COLUMN: XBridge C8(150×4.6)mm, 3.5 μm
Chiral Purity:
  Method info: MOBILE PHASE:0.1% DEA IN HEXANE:IPA::80:20
  COLUMN:CHIRALCEL OJ-H(250×4.6)mm, 5 μm
  Flow rate:1.0 ml/min

EXAMPLE 34

Biochemical Activity Testing of ADAMTS-5: Aggrecan Peptide Cleavage Assay

ADAMTS-5 is a metallo protease with glutamyl-endoprotease activity and cleaves aggrecan core protein at E373-A374 in the interglobular domain. To fully analyse the inhibitory potential of compounds on AdamTS-5 activity an Alphascreen® assay with a biotinylated 43mer aggrecan oligopeptide as substrate was performed. Cleavage by ADAMTS-5 caused production of a neoepitop N-terminus ARGS at the C-terminal fragment. The detection of this product is performed with streptavidin-AlphaScreen® donor beads binding to the biotin label and an anti-neoepitop ("ARGSV") antibody that anchors anti-mouse IgG-coated AlphaLisa® acceptor beads to the other end of the generated fragment. Thereby, donor and acceptor beads get in proximity and a luminescence Alphascreen® signal is generated via the release of singlet oxygen. The cleavage activity was detectable directly by the increase in Alphascreen® signal.

The aggrecan peptide cleavage assay was performed as 384 well AlphaScreen® (Perkin Elmer) assay format in Perkin Elmer 384 AlphaPlate (proxiplate) shallow well microtiter plates and was used for high throughput screen in a total assay volume of 10 μl. 4.5 nM human recombinant AdamTS-5 (R&D systems, Wiesbaden, Germany) and 30 nM biotinylated peptide ITVQTVTWPDMELPLPRNI-TEGEARGSVILTVKPIFEVSPSPL-K(bio) (custom-made, Biosynthan, Berlin, Germany) as substrate were incubated in a total volume of 6 μl (100 mM Tris/HCl, 150 mM NaCl, 10 mM CaCl₂, 0.05% Brij®-35, 1% DMSO, 0.084% BSA, pH 7.5) in the absence or presence of the test compound (10 dilution concentrations) for 180 min at 37° C. The reaction was stopped and the first detection step performed by the addition of 2 μl detection solution 1 (48 mM EDTA, 8 nM aggrecan antibody N-term neoepitope ARG, mouse monoclonal BC3 antibody (MDBioproducts, Egg, Switzerland), 100 μg/ml Streptavidin Alphascreen® donor beads (Perkin Elmer, Rodgau, Germany) in 100 mM Tris/HCl, 150 mM NaCl, 0.05% Brij®-35, 0.1% BSA, pH 7.5). After an one-hour incubation at 37° C. 2 μl of the second detection solution (25 μg/ml anti-mouse AlphaLisa® acceptor beads (Perkin Elmer, Rodgau, Germany) in 100 mM Tris/HCl, 150 mM NaCl, 0.05% Brij®-35, 0.1% BSA, pH 7.5 were added. The plates were incubated for 2 at 37° C. in the dark.

The AlphaScreen signal was measured with an Envision multimode reader (Perkin Elmer LAS Germany GmbH) with the Alphascreen protocol from Perkin Elmer (laser mode) emission wavelength 570 nm. The full value used was the inhibitor-free reaction. For the zero value a pharmacological reference was used. The inhibitory values (IC50) for the compounds were determined using either the program Symyx Assay Explorer® or Condosseo® from GeneData.

EXAMPLE 35

Biochemical Activity Testing of MMP1 & MMP14: Quenched Peptide Protease Assay To determine the modulation of MMP-1 respectively MMP-14 protease activity a continuous enzymatic test with a synthetic peptide substrate, that was labeled with the fluorophore MCA ((7-methoxycoumarin-4-yl)acetyl) quenched by the second label Dnp (2,4 dinitrophenyl) on the peptide was performed in 384 well Greiner low volume non binding microtiter plates and was used for high throughput screen. The cleavage of the peptide substrate by MMP-1/14 produces an increase in fluorescence intensity. To measure the inhibitory activity of compounds the time dependent (kinetic measurement) increase in fluorescence intensity was determined that is correlated directly with the conversion of substrate.

10 nM human recombinant MMP-1 catalytic domain (Enzo Life Sciences, Lôrach, Germany) respectively 2.3 nM human recombinant MMP-14 catalytic domain (Enzo Life Sciences, Lôrach, Germany) were mixed with 7.5 µM peptide substrate MCA-Pro-Leu-Gly-Leu-Dap(DNP)-Ala-Arg-NH$_2$ (Enzo Life Sciences, Lôrach, Germany) in a total volume of 10 µl (25 mM Hepes, 100 NaCl, 10 mM CaCl$_2$, 0.02% Brij®-35, 1% DMSO, pH 7.6) in the absence or presence of the test compound (10 dilution concentrations). After addition of the substrate a first fluorescence intensity measurement (time point 1) was performed with an Envision multimode reader (Perkin Elmer LAS Germany GmbH) at excitation wavelength 340 nm and emission wavelength 450 nm. After the incubation of the reaction for 150 min at room temperature the second measurement was performed with the same parameters as described above. To analyse the activity of the MMPs the differences in fluorescence intensities were calculated. The full value used was the inhibitor-free reaction. The pharmacological zero value used was GM6001 (Sigma-Aldrich, Taufkirchen, Germany) in a final concentration of 340 respectively 160 nM. The inhibitory values (IC50) were determined using either the program Symyx Assay Explorer® or Condosseo® from GeneData.

EXAMPLE 36

IL-1 Induced Cartilage Breakdown Assay for Testing of ADAMTS-5 Inhibitors

The assay is based on bovine cartilage explants from the metacarpal joint (MCP) with a diameter of 4 mm and a thickness of 1-2 mm. Explants are freshly harvested at the day of slaughter. Before the start of the experiment, explants are incubated in DMEM medium+10% serum+30 µg/ml ascorbic acid for 48 h (200 µl). The pre-incubation is performed to enlarge the assay window. Explants are incubated at 37° C. and 7.5% CO2. The number of replicates for all groups is n=4.

Induction of cartilage degradation is induced by treatment of the explants with IL-1 alpha (10 ng/ml) in serum-free medium for 5 days. As negative control, explants are left untreated in serum-free DMEM medium. This control is not part of the baseline calculation but an internal control for the degree of degradation which is strictly dependent on the IL1-alpha quality. IL-1 alpha induces the activity of proteases such as ADAMTS-5 and MMPs which in turn degrade the matrix. Degradation products of the matrix (GAG: glycosaminoglycan) can be measured in the supernatant. The level of GAG release induced by IL1-alpha is defined as the 0% effect level. As a positive control for the inhibition of ADAMTS-5, which is reflected in a decrease of GAG release to the medium, the compound ((S)-4-[(Biphenyl-4-carbonyl)-amino]-4-[2-(4-fluoro-phenyl)-1,1-dimethyl-ethylcarbamoyl]-butyric acid of the WO2007008994 (21 µM) is used. This is regarded as the 100% effect level. Potential ADAMTS-5 inhibitors are first tested at a concentration of 1 µM. Compounds which decrease GAG release up to 50% are re-tested with a concentration of 0.1 µM. Compounds with an effect >50% on GAG release are then selected for a full dose-response (30 µM, 10 µM, 3 µM, 1 µM, 0.3 µM, 0.1 µM, 0.03 µM, 0.01 µM). This DRC is the basis for the IC50 calculation.

IL-1 alpha and the ADAMTS-5 inhibitors are incubated for 5 days, then GAG is measured in the supernatant. The explants are digested with papain to determine the amount of GAG in the explants.

EXAMPLE 37

Cartilage Explant Assay

In order to investigate the effect of potential cathepsin D inhibitors on cartilage degradation, a pH-induced model based on bovine explants is used. The pH of the medium in which the explants are cultivated is matched here to the pathophysiological pH of an arthritic knee. This pH is pH 5.5. In this ex vivo model, potential cathepsin D inhibitors are subsequently investigated for their action with respect to stopping of the cartilage degradation process. If the cartilage is destroyed, glycosaminoglycans (GAGs) are released into the cell culture supernatant. The amount of GAGs liberated can be determined quantitatively with the aid of DMMB (dimethylmethylene blue hydrochloride). If sulfated GAGs are detected using dimethylmethylene blue hydrochloride, the decrease in the absorption at 633 nm is utilised. Since work can also be carried out at very low GAG concentrations, a dye/GAG complex does not precipitate out even after extended incubation of DMMB with GAG, which sometimes happens after only a short time in other measurement methods. In order to determine the concentration, a calibration line is also recorded using chondroitin sulfate. The GAG values can be used to calculate an $IC_{50}$ value, i.e. a concentration at which a substance exhibits 50% of its action.

Solutions:
Incubation Medium, pH 7.4:
DMEM without FBS, addition of 1% of Pen/Strep and 30 µg/ml of ascorbic acid, the medium is not stored.
Incubation Medium, pH 5.5:
DMEM without FBS, the pH is adjusted by addition of MES and monitored using a pH meter, addition of 1% of Pen/Strep and 30 µg/ml of ascorbic acid.
Solutions for the GAG Measurement:
DMMB Colouring Solution (V=500 ml):
Dissolve 8 mg of DMMB (dimethylmethylene blue) in 2.5 ml of ethanol+1 g of sodium formate+1 ml of formic acid, make up to 500 ml with bidistilled water.
Incubation Medium: FBS (Medium without FBS)
Chondroitin Sulfate Solutions (Standard Curve)
Preparation of standard solutions with the following concentrations: 50 µg/ml; 25 µg/ml; 12.5 µg/ml; 6.25 µg/ml; 3.125 µg/ml; 1.56 µg/ml; 0.78 µg/ml and a blank control of the medium. The preparation of the standard solution is carried out in the medium with which the experiment was also carried out.

1.) Procedure: pH-induced Cartilage Degradation of Bovine Explants

The bovine explants are firstly prepared. The induction of the cartilage degradation is carried out in 96-well plates. One explant is cultivated per well. In each case, 200 µl of DMEM (incubation medium pH 5.5) without FBS+30 µg/ml of ascorbic acid are added. As negative control, explants (n=4) are incubated at pH 7.4 (without FBS). This control is not included in the calculation of the data, but instead ensures that the pH change has the desired effect on the liberation of GAG. At this point, the substances to be tested are added. No pre-incubation of the explants is carried out. The explants are cultivated with the corresponding substances for 3 days in the incubator at 37° C. and 7.5% $CO_2$.

2.) Incubation Procedure

In order to investigate the effect of cathepsin D inhibitors on the liberation of GAG (glycosaminoglycan), the substances are employed in the desired concentration and cultivated for 3 days. The compounds to be tested are tested in a first experiment in a concentration of 1 µM and 1% of DMSO. Substances which have an effect of >50% on the liberation of GAG (this corresponds to <50% of the control in the Assay Explorer) are tested in the next experiment at 100 nM and 1% of DMSO. Substances which have an effect of >50% on the liberation of GAG under these conditions (this corresponds to <50% of the control in the Assay Explorer) are tested in a concentration/effect relationship. The compounds here are investigated in the following concentrations: 30 µM, 10 µM, 3 µM, 1 µM, 0.3 µM, 0.1 µM, 0.03 µM, 0.01 µM.

The positive control used is pepstatin A with a concentration of 0.01 µM. The assay window is defined by the control (pH 5.5), defined as 0% effect, and the control pH 5.5+0.01 µM pepstatin A, defined as 100% effect. After incubation for 3 days, the cell culture supernatants are collected and stored at −20° C. or measured directly. The amount of liberated GAG is measured photometrically.

The effect (1 value) of the respective substance in % based on the positive control (pH 5.5+0.01 µM pepstatin A) and the negative control (pH 5.5) is reported for concentrations of 1 µM and 100 nM. The value represents the average of 4 replicants. In the determination of a concentration/effect relationship, an $IC_{50}$ value is reported to the database (Assay Explorer).

4.) Measurement

The cell culture supernatants (200 µl) are either measured directly or stored at −20° C. In order to ensure an accurate determination of the concentration (µg/ml of GAG in the supernatant) of GAG, the measurement values must be located in the linear region of the standard curve. In order to ensure this, various dilutions are routinely introduced (1/5, 1/10, 1/20, 1/40). The dilutions are prepared with medium and introduced automatically (Hamilton) into a 384-well plate (15 µl). 60 µl of DMMB solution are likewise added automatically (or using a multichannel pipette). A rapid colour reaction occurs, which is subsequently measured at 633 nm using a plate reader (for example Envision).

Depending on the amount of sample present, at least one double determination is carried out.

The data are provided by the MTP reader as csv or xls files and stored as raw data based on this format (xls) or used for the calculation of the percentage effect of the particular compound.

5.) Quality Controls

As control for the induction of the pH-induced cartilage degradation, 4 are incubated at pH 7.4. This corresponds to the physiological pH of the cartilage, and no effect on the liberation of GAG is thus expected here. These GAG values (µg/ml of supernatant) are thus always significantly lower than the GAG values for incubation at pH 5.5.

A further control, which both serves for checking of the experiment, but is also important for the definition of the assay window, is the pepstatin control (pH 5.5+0.01 µM pepstatin A). This substance non-specifically blocks the activity of most proteases and thus determines the maximum possible effect of a compound.

(1) Klompmakers, A. & Hendriks, T. (1986) Anal. Biochem. 153, 80-84, Spectrophotometric Determination of Sulfated Glycosaminoglycans.

(2) Groves, P. J. et al. (1997) Anal. Biochem. 245, 247-248 Polyvinyl alcohol-stabilised binding of sulfated GAGs to dimethylmethylene blue.

6.) Results $IC_{50}$ values were determined for some compounds from the table in Example 1 using this assay and are shown in the table in Example 1.

EXAMPLE 38

Investigation of the Anti-Hyperalgesic Effect in Animals

In order to induce an inflammation reaction, a carrageenan solution (CAR, 1%, 50 µl) was injected intra-articularly on one side into a rat knee joint. The uninjected side was used for control purposes. Six animals per group were used. The threshold was determined by means of a micrometer screw (medial-lateral on the knee joint), and the thermal hyperalgesia was determined by means of a directed infrared light source by the Hargreaves method (Hargreaves et al., 1988) on the sole of the foot. Since the site of inflammation (knee joint) is different from the site of measurement (paw sole), use is made here of the term secondary thermal hyperalgesia, the mechanism of which is of importance for the discovery of effective analge-sics.

Experimental description of thermal hyperalgesia (Hargreaves test): the experimental animal is placed in a plastic chamber on a quartz sheet. Before testing, the experimental animal is firstly given about 5-15 minutes time to familiarise itself with the environment. As soon as the experimental animal no longer moves so frequently after the familiarisation phase (end of the exploration phase), the infrared light source, whose focus is in the plane of the glass bottom, is positioned directly beneath the rear paw to be stimula-ted. An experiment run is then started by pressing the button: infrared light results in an increase in the skin temperature of the rear paw. The experiment is terminated either by the experimental animal raising the rear paw (as an expression of the pain threshold being reached) or by automatic switching-off of the infrared light source when a prespecified maximum temperature has been reached. Light reflected by the paw is recorded as long as the experimental animal sits still. Withdrawal of the paw interrupts this reflection, after which the infrared light source is switched off and the time from switching on to switching off is recorded. The instrument is calibrated in such a way that the infrared light source increases the skin temperature to about 45 degrees Celsius in 10 s (Hargreaves et al. 1988). An instrument produced by Ugo Basile for this purpose is used for the testing.

CAR was purchased from Sigma-Aldrich. Administration of the specific cathepsin D inhibitor, compound no. 23 (from Example 1, Table 1, (S)-2-[(2S,3S)-2-((3S,4S)-3-amino-4-{(S)-3-methyl-2-[(S)-4-methyl-2-(3-methyl-butyrylamino)pentanoylamino]butyrylamino}-5-phenylpentanoylamino)-3-methylpentanoylamino]-3-methylbutyric acid), was carried out intra-articularly 30 minutes before the CAR. Triamcinolone (TAC) in an amount of 10 µg/joint was used as positive control, and the solvent (vehicle) was used as negative control. The hyperalgesia is quoted as the difference in the withdrawal times between the inflamed and non-inflamed paw.

Result: TAC was capable of reducing the CAR-induced swelling, but the specific DDR2 inhibitor was not. In contrast, the specific DDR2 inhibitor was able to reduce the extent of thermal hyperalgesia as a function of the dose. Assessment: it has been shown that the compounds of the present invention exert an anti-hyperalgesic action. This can be postulated, since the compounds of the present invention exhibited no influence on inflammatory swelling and thus on the hyperalgesia trigger. It can thus be assumed that the compounds of the present invention develop a pain-reducing action in humans.

EXAMPLE 39

Stability of the Compounds According to the Invention in Bovine Synovial Fluid

Extraction of Bovine Synovial Fluid:

In the preparation of bovine explants (for the diffusion chamber or other assays), either cow hoof (metacarpal joints) or cow knee is used. The synovial fluid can be obtained from both joints. To this end, the synovial fluid is carefully removed from the open joint using a 10 ml syringe and a cannula and transferred into prepared 2 ml Eppendorf vessels. The Eppendorf vessels are labelled depending on the animal (cow passport is available). It must be ensured here that blood does not enter the joint gap during preparation of the joints. If this is the case, the synovial fluid will become a reddish colour and must consequently be discarded. The synovial fluid is basically highly viscous and clear to yellowish in colour. The removal together with a macroscopic analysis of the synovial fluid is documented.

Batch for Stability Testing of Substances in SF:

In order to check the stability of individual compounds, a pool of four different bovine synovial fluids is mixed. To this end, about 1 ml per SF is used. The mixture is prepared directly in a 5 ml glass vessel. The SFs are mixed thoroughly, but carefully. No air bubbles or foam should form. To this end, a vortex unit is used at the lowest speed. The compounds to be tested are tested in an initial concentration (unless required otherwise) of 1 µM. After addition of the substance, the batch is again mixed thoroughly and carefully. For visual monitoring, all SF batches are photographed, and the pictures are filed in the eLabBio file for the corresponding experiment. FIG. 1 shows photodocumentation of this type by way of example. The batches are incubated in the incubator for 48 h at 37° C. and 7.5% $CO_2$.

Sampling:

The sampling is carried out after the pre-agreed times (unless required otherwise, see below). 200 µl of the SF are removed from the mixture per time and transferred directly into a 0.5 ml "low-binding" Eppendorf vessel. "Low-binding" Eppendorf vessels are used in order to minimise interaction of the substances with the plastic of the vessels. 200 µl of acetonitrile have already been introduced into the Eppendorf vessel, so that a 1+1 mixture of the SF forms thereafter. This simplifies the subsequent analysis, but precipitation of protein may occur immediately after addition of the SF. This should be noted on the protocol. The 0 h sample is taken immediately after addition of the substance. This corresponds to the 100% value in the stability calculation. Ideally, the concentration employed should be retrieved here. The samples can be frozen at −20° C.

0 h
6 h
24 h
48 h

The negative control used is SF without substance. The positive control used is SF with 1 µM of substance. This corresponds to the 0 h value and thus 100% stability.

The samples are stored in "low-binding" Eppendorf vessels at −20° C. The samples are subsequently measured quantitatively.

Data Processing:

The concentrations measured (ng/ml) are plotted against the time in a graph (GraphPad Prism®). The percentage stability of the substance is determined here. The 100% value used is the initial value in the SF at time 0 h. The data are stored in eLabBio under the respective experiment number and reported in the MSR database (as percent stability after the corresponding incubation times).

Results:

All compounds measured remained stable (see tables in Example 1). Compound stability is defined as >80% compound recovery after 48 h.

EXAMPLE 40

Injection Vials

A solution of 100 g of a compound of the formula I and 5 g of disodium hydrogenphosphate in 3 l of bidistilled water is adjusted to pH 6.5 using 2 N hydrochloric acid, filtered under sterile conditions, transferred into injection vials, lyophilised under sterile conditions and sealed under sterile conditions. Each injection vial contains 5 mg of a compound of the formula I.

EXAMPLE 41

Solution

A solution is prepared from 1 g of a compound of the formula I, 9.38 g of $NaH_2PO_4$ 2 $H_2O$, 28.48 g of $Na_2HPO_4$. 12 $H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE 42

Ointment 500 mg of a compound of the formula I are mixed with 99.5 g of Vaseline under aseptic conditions.

EXAMPLE 43

Ampoules

A solution of 1 kg of a compound of the formula I in 60 l of bidistilled water is filtered under sterile conditions, transferred into ampoules, lyophilised under sterile conditions and sealed under sterile conditions. Each ampoule contains 10 mg of a compound of the formula I.

The invention claimed is:

1. A compound of formula I,

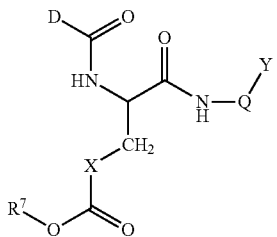

wherein

X is $CHR^1$ or $CR^1R^2$, wherein optionally $R^1$ and $R^2$ with the C-atom they are bound to form a cycloalkyl or heterocyclyl containing 3 to 7 C-atoms wherein optionally 1 to 3 $CH_2$-groups are substituted by —O—, —S—, —SO—, —$SO_2$—, —NR'—, —OCO—, —NRCONR'—, —NRCO—, —$NRSO_2$R'—, —COO—, —CONR'— or —CH═CH— and wherein optionally 1 to 11 H-atoms are substituted by F or Cl, D is -E-G-K or -L, E, K are independently from one another a saturated, unsaturated or aromatic hydrocarboncycle which is unsubstituted or 1 to 4 times substituted by $R^1$ or $R^2$, or a monocylic saturated, unsaturated or aromatic heterocycle with 1 to 4 heteroatoms selected from N, O and S which is unsubstituted or mono-, di- or trisubstituted by $R^1$, $R^2$, ═S, ═$NR^1$ or ═O, G is a single bond, L is -E-G-K, wherein E and K in addition to the single bond G are linked via an additional alkyl linker containing 1 to 3 C-atoms wherein optionally one $CH_2$-group is substituted by —$CR^1R^2$—, —O—, —S—, —SO—, —SO₂—, —NR¹—, —OCO—, —NR¹CONR²—, —NR¹CO—, —NR¹SO₂R²—, —COO—, —CONR¹— or —CH=CH—, Y is H, R¹ or a saturated, unsaturated or aromatic hydrocarboncycle which is unsubstituted or 1 to 4 times substituted by R¹ or a monocylic saturated, unsaturated or aromatic heterocycle with 1 to 4 heteroatoms selected from N, O and S which is unsubstituted or mono-, di- or trisubstituted by R¹, =S, =NR¹ or =O, Q is a single bond or a linear, branched or mono- or bicyclic alkyl linker containing 1 to 10 C-atoms wherein optionally 1 to 5 CH₂-groups are substituted by —CR³R⁴—, —S—, —SO—, —SO₂—, —NR³—, —OCO—, —NR³CONR⁴—, —NR³CO—, —NR³SO₂R⁴'—, —COO— or —CONR³— and wherein optionally 1 to 20 H-atoms are substituted by F or Cl, wherein R³ and R⁴ with the atoms they are bound to optionally form a cycloalkyl or heterocyclyl containing 3 to 7 C-atoms wherein optionally 1 to 3 CH₂-groups are substituted by —O—, —S—, —SO—, —SO₂—, —NR—, —OCO—, —NRCONR'— —NRCO—, —NRSO₂R'—, —COO— or CONR' and —CH=CH— and wherein optionally 1 to 11 H-atoms are substituted by F or Cl, R¹, R², R³, R⁴ are independently from one another selected from the group consisting of Hal, OR, NRR, SOR, SO₂R, SO₂NRR, CN, COOR, CONRR, NRCONRR, NRSO₂R, NRCOR, a linear or branched alkyl containing 1 to 10 C-atoms which is unsubstituted or mono-, di- or trisubstituted by =S, =NR, =O, E, OR, NRR, SOR, SO₂R, SO₂NRR, CN, COOR, CONRR, NRCONRR, NRSO₂R or NRCOR, wherein optionally 1 to 3 CH₂-groups are substituted by —O—, —S—, —SO—, —SO₂—, —NR—, —OCO—, —NRCONR'—, —NRCO—, —NRSO₂R'—, —COO—, —CONR'—, —C≡C— or —CH=CH— and wherein optionally 1 to 20 H-atoms are substituted by F or Cl, and a cycloalkyl or heterocyclyl containing 3 to 7 C-atoms which is unsubstituted or mono-, di- or trisubstituted by =S, =NR, =O, E, OR, NRR, SOR, SO₂R, SO₂NRR, CN, COOR, CONRR, NRCONRR, NRSO₂R or NRCOR, wherein optionally 1 to 3 CH₂-groups are substituted by —O—, —S—, —SO—, —SO₂—, —NR—, —OCO—, —NRCONR'—, —NRCO—, —NRSO₂R'—, —COO—, —CONR'— and —CH=CH— and wherein optionally 1 to 11 H-atoms are substituted by F or Cl, R is H, Hal, R⁵, OR⁵, NR⁵, SO₂R⁵, SO₂NR⁵R⁶, CN, COOR⁵, CONR⁵R⁶, NR⁵CONR⁵R⁶, NR⁵SO₂R⁶, NR⁵COR⁶, a linear or branched alkyl containing 1 to 10 C-atoms which is unsubstituted or mono-, di- or trisubstituted by =S, =NR⁵, =O, Hal, E, R⁵, OR⁵, NR⁵, SO₂R⁵, SO₂NR⁵R6, CN, COOR⁵, CONR⁵R⁶, NR⁵CONR⁵R⁶, NR⁵SO₂R⁶ or NR⁵COR⁶, wherein optionally 1 to 3 CH₂-groups are substituted by —O—, —S—, —SO—, —SO₂—, —NR⁵—, —OCO—, —NR⁵CONR⁶—, —NR⁵CO—, —NR⁵SO₂R⁶—, —COO—, —CONR⁵—, —C≡C— or —CH=CH— and wherein optionally 1 to 20 H-atoms are substituted by F or Cl, and a cycloalkyl or heterocyclyl containing 3 to 7 C-atoms which is unsubstituted or mono-, di- or trisubstituted by =S, =NR⁵, =O, Hal, R⁵, OR⁵, NR⁵, SO₂R⁵, SO₂NR⁵R⁶, CN, COOR⁵, CONR⁵R⁶, NR⁵CONR⁵R⁶, NR⁵SO₂R⁶ or NR⁵COR⁶, wherein optionally 1 to 3 CH₂-groups are substituted by —O—, —S—, —SO—, —SO₂—, —NR⁵—, —OCO—, —NR⁵CONR⁶—, —NR⁵CO—, —NR⁵SO₂R⁶—, —COO—, —CONR⁵— or —CH=CH— and wherein optionally 1 to 11 H-atoms are substituted by F or Cl, R⁵, R⁶ independently from one another are H, alkyl or a mono- or bicyclic saturated, unsaturated or aromatic hydrocarboncycle or heterocyle with 1 to 4 heteroatoms selected from N, O and S R⁷ is H or alkyl containing 1 to 7 C-atoms, and Hal F, Cl, Br or I, R' is E, or linear or branched alkylene containing 1 to 10 C-atoms which is unsubstituted or mono-, di- or trisubstituted by =S, =NR⁵, =O, Hal, E, R⁵, OR⁵, NR⁵, SO₂R⁵, SO₂NR⁵R6, CN, COOR⁵, CONR⁵R⁶, NR⁵CONR⁵R⁶, NR⁵SO₂R⁶ or NR⁵COR⁶, wherein optionally 1 to 3 CH₂-groups are substituted by —O—, —S—, —SO—, —SO₂—, —NR⁵—, —OCO—, —NR⁵CONR⁶—, —NR⁵CO—, —NR⁵SO₂R⁶—, —COO—, —CONR⁵—, —C≡C— or —CH=CH— and wherein optionally 1 to 20 H-atoms are substituted by F or Cl, and a cycloalkyl or heterocyclyl containing 3 to 7 C-atoms which is unsubstituted or mono-, di- or trisubstituted by =S, =NR⁵, =O, Hal, R⁵, OR⁵, NR⁵, SO₂R⁵, SO₂NR⁵R⁶, CN, COOR⁵, CONR⁵R⁶, NR⁵CONR⁵R⁶, NR⁵SO₂R⁶ or NR⁵COR⁶, wherein optionally 1 to 3 CH₂-groups are substituted by —O—, —S—, —SO—, —SO₂—, —NR⁵—, —OCO—, —NR⁵CONR⁶—, —NR⁵CO—, —NR⁵SO₂R⁶—, —COO—, —CONR⁵— or —CH=CH— and wherein optionally 1 to 11 H-atoms are substituted by F or Cl, R⁴' is E, or linear branched alkylene containing 1 to 10 C-atoms which is unsubstituted or mono-, di- or trisubstituted by =S, =NR, =O, E, OR, NRR, SOR, SO₂R, SO₂NRR, CN, COOR, CONRR, NRCONRR, NRSO₂R or NRCOR, wherein optionally 1 to 3 CH₂-groups are substituted by —O—, —S—, —SO—, —SO₂—, —NR'—, —OCO—, —NRCONR'—, —NRCO—, —NRSO₂R'—, —COO—, —CONR—, —C≡C— or —CH=CH— and wherein optionally 1 to 20 H-atoms are substituted by F or Cl, and a cycloalkyl or heterocyclyl containing 3 to 7 C-atoms which is unsubstituted or mono-, di- or trisubstituted by =S, =NR, =O, E, OR, NRR, SOR, SO₂R, SO₂NRR, CN, COOR, CONRR, NRCONRR, NRSO₂R or NRCOR, wherein optionally 1 to 3 CH₂-groups are substituted by —O—, —S—, —SO—, —SO₂—, NR'—, —OCO—,—NRCONR'— —NRCO—, —NRSO₂R'—, —COO—, —CONR'— and —CH=CH— and wherein optionally 1 to 11 H-atoms are substituted by F or Cl, or a physiologically acceptable salt, solvate or stereoisomer thereof, including mixtures thereof in all ratios.

2. The compound according to claim 1 in which E is

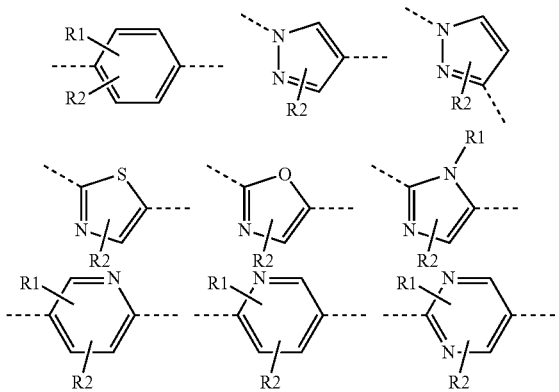

-continued
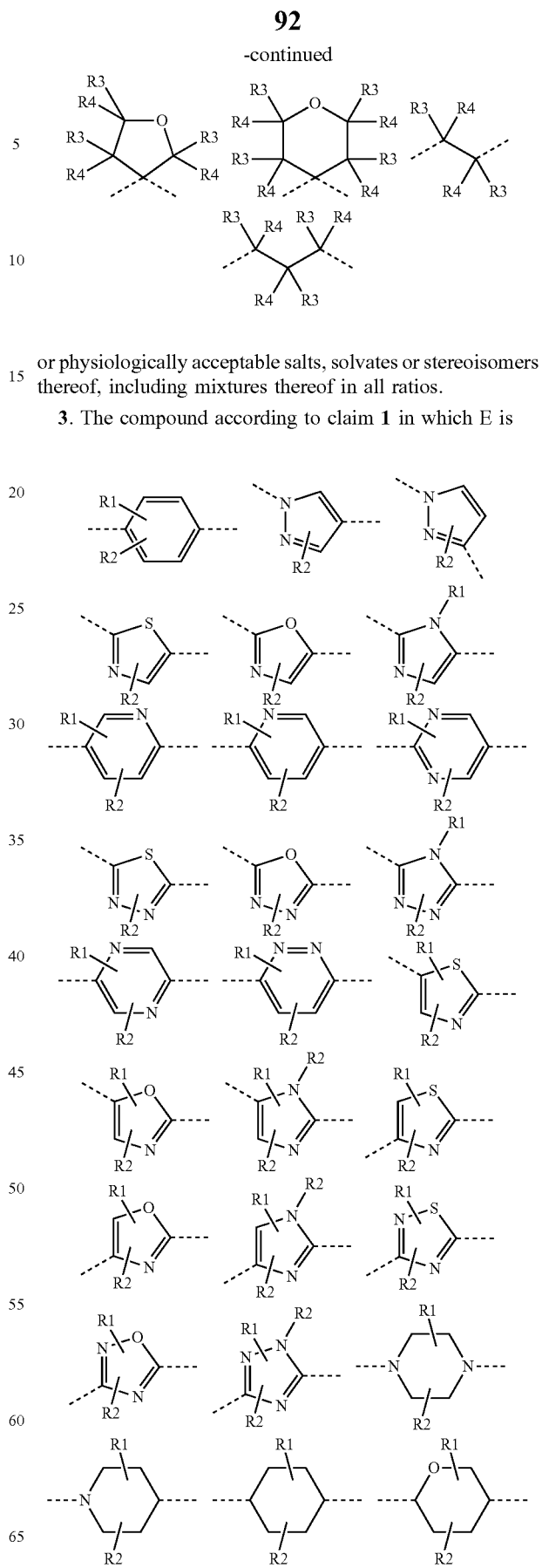
or physiologically acceptable salts, solvates or stereoisomers thereof, including mixtures thereof in all ratios.
3. The compound according to claim 1 in which E is
-continued
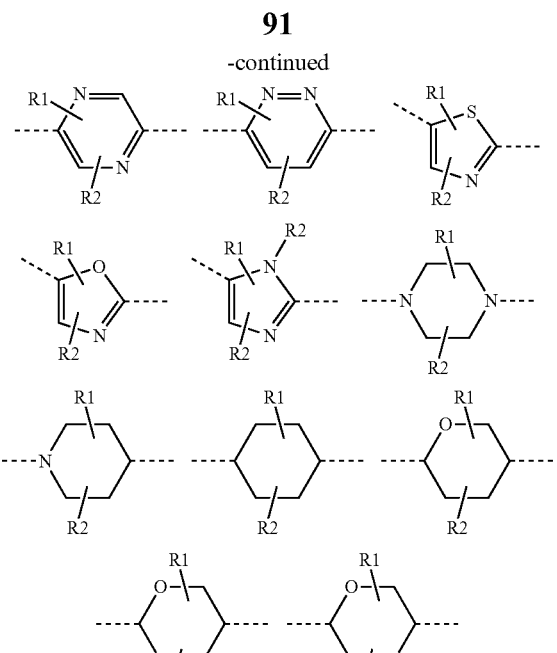
K is
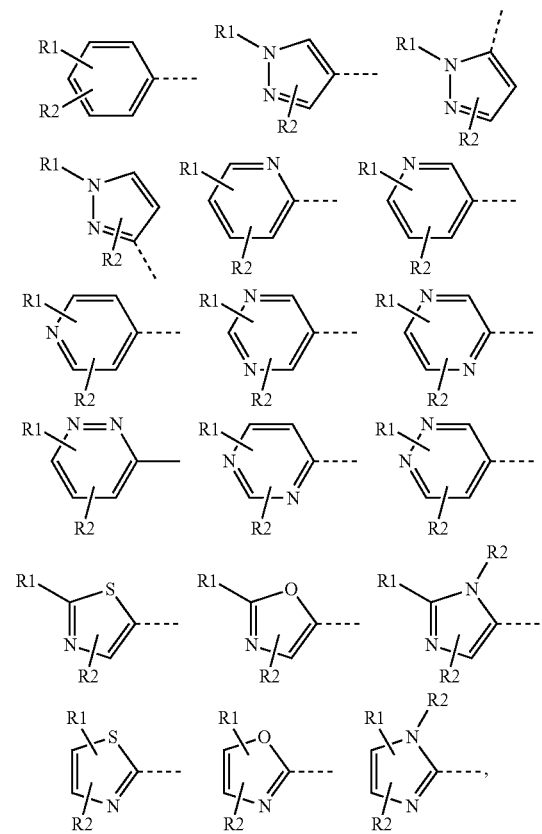
Q is
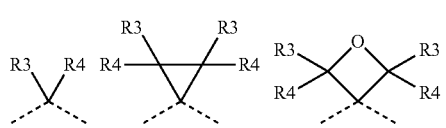

-continued

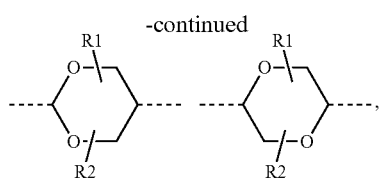

K is

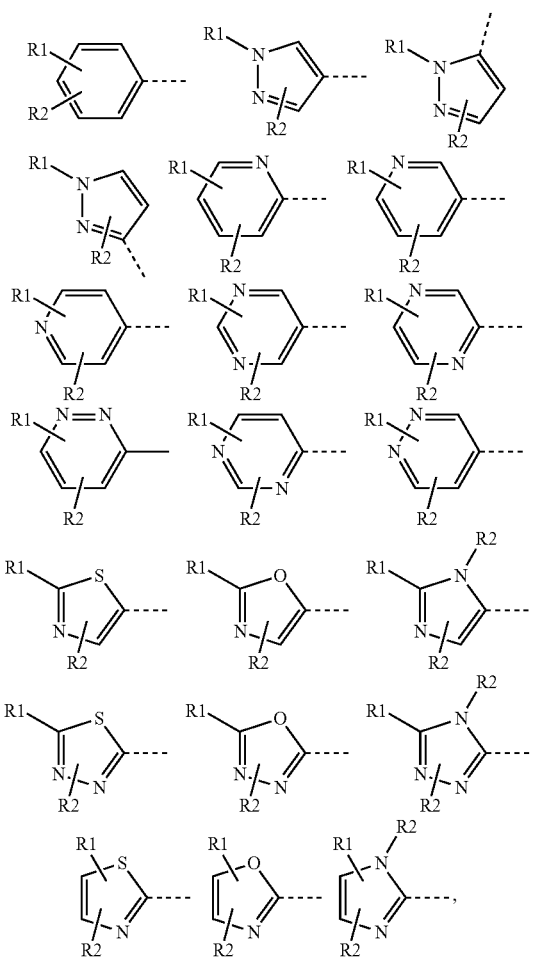

Q is

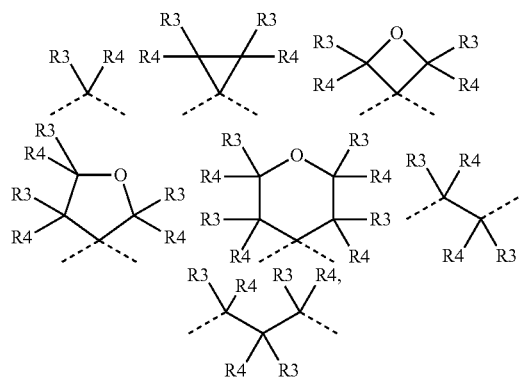

R¹,R² are independently from one another a linear or branched alkyl containing 1 to 5 C-atoms which is unsubstituted or mono-, di- or trisubstituted by E, OR, NRR, COOR, CONRR, NRCOR or NRCONRR, wherein optionally 1 to 3 CH$_2$-groups are substituted by —O—, —NR'—, —OCO—, —NRCONR'—, —NRCO—, —COO— or —CONR'— and wherein optionally 1 to 10 H-atoms are substituted by F, or a cycloalkyl containing 3 to 6 C-atoms which is unsubstituted or mono-, di- or trisubstituted by E, OR, NRR, COOR, CONRR, NRCOR or NRCONRR, wherein optionally 1 to 3 CH$_2$-groups are substituted by —O—, —NR'— —OCO—, —NRCONR'—, —NRCO—, —COO— or —CONR'— and wherein optionally 1 to 10 H-atoms are substituted by F, or physiologically acceptable salts, solvates or stereoisomers thereof, including mixtures thereof in all ratios.

4. The compounds according to claim 1 in which E is

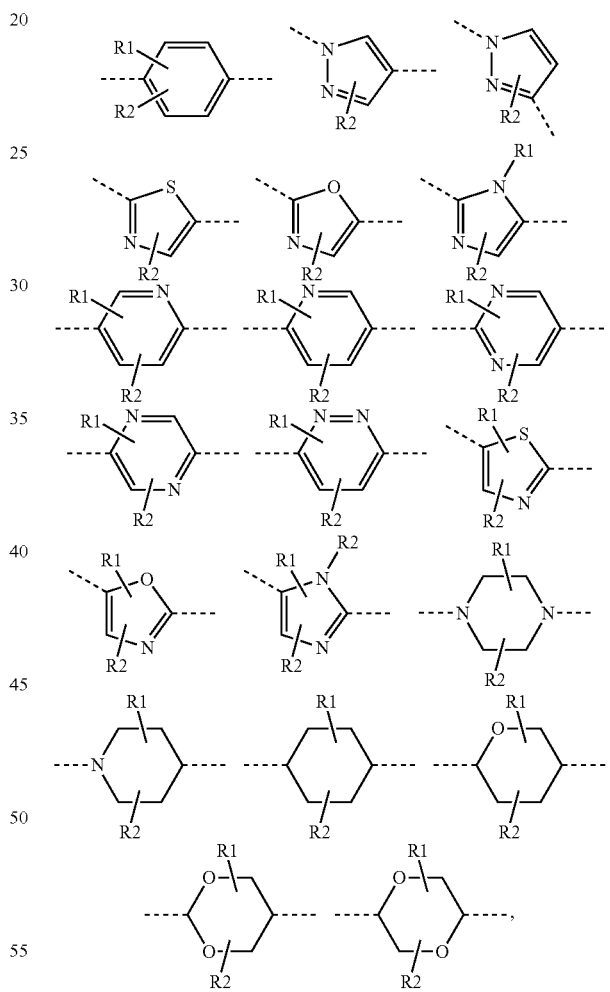

K is

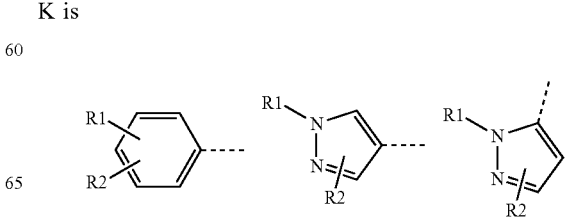

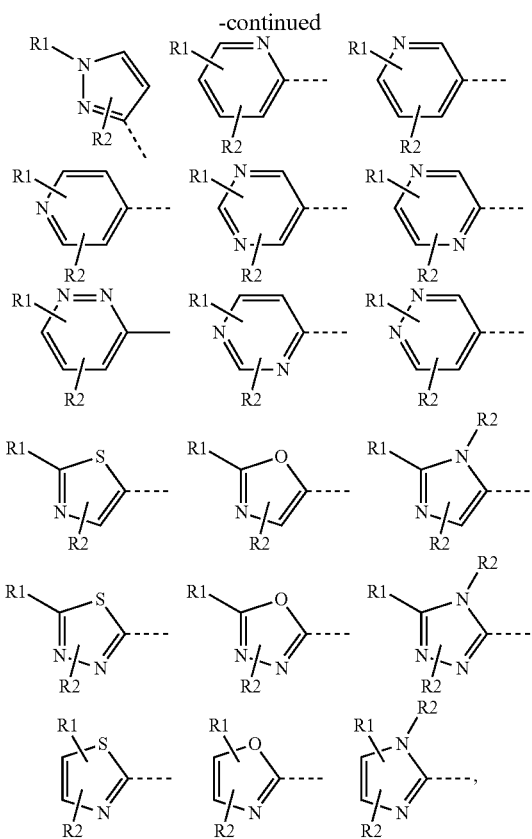

Q is

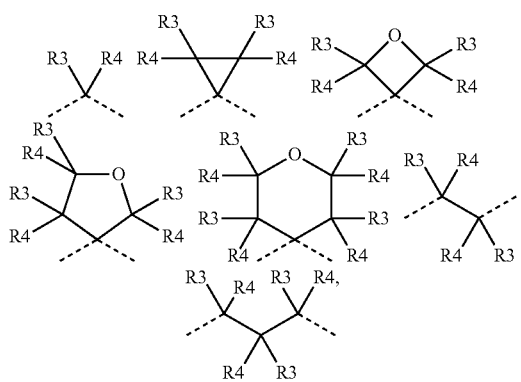

$R^1, R^2$ are independently from one another methyl, ethyl, propyl, cyclopropyl, isopropyl, butyl, isobutyl, 2-butyl, tert-butyl, cyclobutyl, OH or OR, which is unsubstituted or mono-, di- or trisubstituted by E or OR and wherein optionally 1 to 3 CH$_2$-groups are substituted by —O— or —NR— and wherein optionally 1 to 10 H-atoms are substituted by F, or physiologically acceptable salts, solvates or stereoisomers thereof, including mixtures thereof in all ratios.

5. The compound of formula
a) 4-[(Biphenyl-4-carbonyl)-amino]-2-methyl-4-(3,4,5-trimethoxy-benzylcarbamoyl)-butyric acid
b) (2S,4S)-4-[2-(4-Fluoro-phenyl)-1,1-dimethyl-ethylcarbamoyl]-4-{[5-(4-fluoro-phenyl)-thiazole-2-carbonyl]-amino}-2-methyl-butyric acid
c) (2S,4S)-4-[(Biphenyl-4-carbonyl)-amino]-4-[(S)-2-(4-fluoro-phenyl)-1-methyl-ethylcarbamoyl]-2-methyl-butyric acid
d) (2S,4S)-4-[(Biphenyl-4-carbonyl)-amino]-4-(1,1-dimethyl-2-pyridin-3-yl-ethylcarbamoyl)-2-methyl-butyric acid
e) (2S,4S)-4-[(Biphenyl-4-carbonyl)-amino]-4-[2-(4-fluoro-phenyl)-1,1-dimethyl-ethylcarbamoyl]-2-methyl-butyric acid
f) (2S,4S)-2-Benzyl-4-[(biphenyl-4-carbonyl)-amino]-4-[2-(4-fluoro-phenyl)-1,1-dimethyl-ethylcarbamoyl]-butyric acid
g) (2S,4S)-2-[(Biphenyl-4-carbonyl)-amino]-2-[2-(4-fluoro-phenyl)-1,1-dimethyl-ethylcarbamoyl]-ethyl}-pentanoic acid
h) (2S,4S)-4-[(Biphenyl-4-carbonyl)-amino]-4-[2-(4-fluoro-phenyl)-1,1-dimethyl-ethylcarbamoyl]-2-methoxymethyl-butyric acid
i) (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid
j) (2S,4S)-4-[2-(4-Fluoro-phenyl)-1,1-dimethyl-ethylcarbamoyl]-2-methyl-4-(4-pyridin-2-yl-benzoylamino)-butyric acid
k) (2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid
l) (2S,4S)-4-[2-(4-Fluoro-phenyl)-1,1-dimethyl-ethylcarbamoyl]-4-{[1-(4-fluoro-phenyl)-piperidine-4-carbonyl]-amino}-2-methyl-butyric acid
m) 4-[2-(4-Fluoro-phenyl)-1,1-dimethyl-ethylcarbamoyl]-2-methyl-4-[(5-phenyl-pyridine-2-carbonyl)-amino]-butyric acid
n) (2S,4S)-4-[2-(4-Fluoro-phenyl)-1,1-dimethyl-ethylcarbamoyl]-2-methyl-4-[(6-phenyl-pyridine-3-carbonyl)-amino]-butyric acid
o) (2S,4S)-4-[2-(4-Fluoro-phenyl)-1,1-dimethyl-ethylcarbamoyl]-2-methyl-4-[(4-phenyl-piperazine-1-carbonyl)-amino]-butyric acid
p) (2S,4S)-4-[2-(4-Fluoro-phenyl)-1,1-dimethyl-ethylcarbamoyl]-2-methyl-4-(4-pyridin-3-yl-benzoylamino)-butyric acid
q) (2S,4S)-4-[2-(4-Fluoro-phenyl)-1,1-dimethyl-ethylcarbamoyl]-2-methyl-4-[4-(5-methyl-thiazol-2-yl)-benzoylamino]-butyric acid
r) (2S,4S)-4-[2-(4-Fluoro-phenyl)-1,1-dimethyl-ethylcarbamoyl]-4-{[2-(4-fluoro-phenyl)-thiazole-5-carbonyl]-amino}-2-methyl-butyric acid
s) (2S,4S)-4-[2-(4-Fluoro-phenyl)-1,1-dimethyl-ethylcarbamoyl]-2-methyl-4-(4-pyrazol-1-yl-benzoylamino)-butyric acid
t) (2S,4S)-4-Amino-4-[2-(4-fluoro-phenyl)-1,1-dimethyl-ethylcarbamoyl]-2-methyl-butyric acid methyl ester
u) (2S,4S)-4-[2-(4-Fluoro-phenyl)-1,1-dimethyl-ethylcarbamoyl]-2-methyl-4-[(6-phenyl-pyridine-3-carbonyl)-amino]-butyric acid methyl ester
v) (2S,4S)-4-[2-(4-Fluoro-phenyl)-1,1-dimethyl-ethylcarbamoyl]-2-methyl-4-(4-pyridin-3-yl-benzoylamino)-butyric acid methyl ester
w) (2S,4S)-4-[2-(4-Fluoro-phenyl)-1,1-dimethyl-ethylcarbamoyl]-2-methyl-4-(4-pyridin-2-yl-benzoylamino)-butyric acid methyl ester
x) (2S,4S)-4-[(3-Fluoro-biphenyl-4-carbonyl)-amino]-4-[2-(4-fluoro-phenyl)-1,1-dimethyl-ethylcarbamoyl]-2-methyl-butyric acid methyl ester y) (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid methyl ester
z) (2S,4S)-4-[2-(4-Fluoro-phenyl)-1,1-dimethyl-ethylcarbamoyl]-4-{[5-(4-fluoro-phenyl)-thiazole-2-carbonyl]-amino}-2-methyl-butyric acid methyl ester
aa) (2S,4S)-4-[2-(4-Fluoro-phenyl)-1,1-dimethyl-ethylcarbamoyl]-4-{[2-(4-fluoro-phenyl)-thiazole-5-carbonyl]-amino}-2-methyl-butyric acid methyl ester
bb) (2S,4S)-4-[2-(4-Fluoro-phenyl)-1,1-dimethyl-ethylcarbamoyl]-2-methyl-4-[4-(5-methyl-thiazol-2-yl)-benzoylamino]-butyric acid methyl ester
cc) (2S,4S)-4-[2-(4-Fluoro-phenyl)-1,1-dimethyl-ethylcarbamoyl]-4-{[1-(4-fluoro-phenyl)-piperidine-4-carbonyl]amino}-2-methyl-butyric acid methyl ester
dd) (2S,4S)-4-[2-(4-Fluoro-phenyl)-1,1-dimethyl-ethylcarbamoyl]-2-methyl-4-(4-pyrazol-1-yl-benzoylamino)-butyric acid methyl ester
ee) (2S,4S)-4-[2-(4-Fluoro-phenyl)-1,1-dimethyl-ethylcarbamoyl]-2-methyl-4-[(4-phenyl-piperidine-1-carbonyl)-amino]-butyric acid methyl ester
ff) (2S,4S)-4-[2-(4-Fluoro-phenyl)-1,1-dimethyl-ethylcarbamoyl]-2-methyl-4-[(4-phenyl-piperazine-1-carbonyl)-amino]-butyric acid methyl ester
gg) (2S,4S)-4-[(Biphenyl-4-carbonyl)-amino]-2-methyl-4-(3,4,5-trimethoxy-benzylcarbamoyl)-butyric acid methyl ester
hh) (2S,4S)-4-[(Biphenyl-4-carbonyl)-amino]-4-[2-(4-fluoro-phenyl)-1-methyl-ethylcarbamoyl]-2-methyl-butyric acid methyl ester
ii) (2S,4S)-4-[(Biphenyl-4-carbonyl)-amino]-4-(1,1-dimethyl-2-pyridin-3-yl-ethylcarbamoyl)-2-methyl-butyric acid methyl ester
jj) (2S,4S)-4-[2-(4-Fluoro-phenyl)-1,1-dimethyl-ethylcarbamoyl]-2-methyl-4-(4-pyrazin-2-yl-benzoylamino)-butyric acid
kk) (2S,4S)-4-[(Biphenyl-4-carbonyl)-amino]-2-methyl-4-(1,1,3-trimethyl-butylcarbamoyl)-butyric acid
ll) (2S,4S)-4-[2-(4-Fluoro-phenyl)-1,1-dimethyl-ethylcarbamoyl]-2-methyl-4-[(5-phenyl-pyrazine-2-carbonyl)-amino]-butyric acid
mm) (2S,4S)-4-[2-(4-Fluoro-phenyl)-1,1-dimethyl-ethylcarbamoyl]-2-methyl-4-(4-pyrazol-1-yl-benzoylamino)-butyric acid
nn) (2S,4S)-4-[4-(1-Difluoromethyl-1H-pyrazol-4-yl)-benzoylamino]-4-[2-(4-fluoro-phenyl)-1,1-dimethyl-ethylcarbamoyl]-2-methyl-butyric acid
oo) (2S,4S)-4-[2-(4-Fluoro-phenyl)-1,1-dimethyl-ethylcarbamoyl]-2-methyl-4-[4-(1-methyl-1H-pyrazol-3-yl)-benzoylamino]-butyric acid
pp) (S)-4-[(Biphenyl-4-carbonyl)-amino]-4-[2-(4-fluoro-phenyl)-1,1-dimethyl-ethylcarbamoyl]-2,2-dimethyl-butyric acid
qq) (2S,4S)-4-[(Biphenyl-4-carbonyl)-amino]-4-[3-(4-fluoro-benzyl)-oxetan-3-ylcarbamoyl]-2-methyl-butyric acid
rr) (2S,4S)-4-[(Biphenyl-4-carbonyl)-amino]-4-(1,1-dimethyl-propylcarbamoyl)-2-methyl-butyric acid or physiologically acceptable salts, solvates or stereoisomers thereof, including mixtures thereof in all ratios.

6. The compound according to claim 1 or physiologically acceptable salts, solvates or stereoisomers thereof, including mixtures thereof in all ratios, capable of functioning as ADAMTS5 inhibitors.

7. A pharmaceutical composition comprising a pharmaceutically acceptable carrier and at least one compound according to claim 1 or physiologically acceptable salts, solvates or stereoisomers thereof, including mixtures thereof in all ratios.

8. A pharmaceutical composition comprising at least one compound according to claim 1 or physiologically acceptable salts, solvates or stereoisomers thereof, including mixtures thereof in all ratios, and at least one further medicament active ingredient.

9. A process for the preparation of a pharmaceutical composition, comprising bringing a compound according to claim 1 or one of its physiologically acceptable salts, solvates or stereoisomers, including mixtures thereof in all ratios, into a suitable dosage form together with a solid, liquid or semi-liquid excipient or adjuvant.

10. A method for treatment of osteoarthritis, rheumatoid arthritis, traumatic cartilage injuries, pain, allodynia, or hyperalgesia, comprising administering to a host in need thereof an effective amount of a compound according to claim 1, or a salt or solvate thereof.

11. A kit comprising separate packs of
a) an effective amount of a compound according to claim 1 or physiologically acceptable salts, derivatives, solvates or stereoisomers thereof, including mixtures thereof in all ratios, and
b) an effective amount of a further medicament active ingredient.

* * * * *